US010272233B2

(12) United States Patent
Kang et al.

(10) Patent No.: US 10,272,233 B2
(45) Date of Patent: Apr. 30, 2019

(54) METHOD TO FABRICATE POLYMERIC MICRONEEDLES

(71) Applicant: National University of Singapore, Singapore (SG)

(72) Inventors: Lifeng Kang, Singapore (SG); Sui Yung Chan, Singapore (SG); Jaspreet Singh Kochhar, Singapore (SG); Wei Jiang Goh, Singapore (SG)

(73) Assignee: National University of Singapore, Singapore (SG)

( * ) Notice: Subject to any disclaimer, the term of this patent is extended or adjusted under 35 U.S.C. 154(b) by 407 days.

(21) Appl. No.: 14/385,236

(22) PCT Filed: Mar. 15, 2013

(86) PCT No.: PCT/SG2013/000108
§ 371 (c)(1),
(2) Date: Sep. 15, 2014

(87) PCT Pub. No.: WO2013/137831
PCT Pub. Date: Sep. 19, 2013

(65) Prior Publication Data
US 2015/0080802 A1 Mar. 19, 2015

Related U.S. Application Data

(60) Provisional application No. 61/611,603, filed on Mar. 16, 2012.

(51) Int. Cl.
A61M 37/00 (2006.01)
G03F 7/20 (2006.01)

(52) U.S. Cl.
CPC ....... *A61M 37/0015* (2013.01); *G03F 7/2002* (2013.01); *A61M 2037/0053* (2013.01)

(58) Field of Classification Search
CPC .......... G03F 7/00; C03C 25/00; A61M 37/00; A61M 5/32; A61M 5/20; A61M 5/14; B05D 5/00
(Continued)

(56) References Cited

U.S. PATENT DOCUMENTS 7,132,054 B1 * 11/2006 Kravitz ............ A61M 37/0015
216/11
7,763,203 B2 7/2010 Arias et al.
(Continued)

OTHER PUBLICATIONS

Park et al., Tapered Conical Polymer Microneedles Fabricated Using an Integrated Lens Technique for transdermal Drug Delivery, 2007, IEEE Transactions on Biomedical Engineering, vol. 54, No. 5, pp. 903-913.*
(Continued)

Primary Examiner — Andrew J Bowman
(74) Attorney, Agent, or Firm — Hamilton, Brook, Smith & Reynolds, P.C.

(57) ABSTRACT

The present disclosure relates generally to microneedle devices and methods for fabricating microneedles from a biocompatible polymer using photolithography. More particularly, aspects of the present disclosure are directed to the fabrication of microneedle devices using a biocompatible polymer (biopolymer) by way of biocompatible, essentially biocompatible, or substantially biocompatible fabrication techniques.

17 Claims, 29 Drawing Sheets

(58) Field of Classification Search
USPC .......... 427/2.3; 514/15.2; 216/11; 430/313; 604/506, 140, 136, 131
See application file for complete search history.

(56) References Cited

U.S. PATENT DOCUMENTS

| | | | | |
|---|---|---|---|---|
| 2004/0072105 | A1* | 4/2004 | Yeshurun | A61M 37/0015 430/313 |
| 2007/0023386 | A1 | 2/2007 | Kravitz | |
| 2007/0161964 | A1 | 7/2007 | Yuzhakov | |
| 2008/0213461 | A1* | 9/2008 | Gill | A61K 9/0021 427/2.3 |
| 2008/0269685 | A1 | 10/2008 | Singh et al. | |
| 2009/0043279 | A1 | 2/2009 | Kaspar et al. | |
| 2009/0143762 | A1* | 6/2009 | Stinchcomb | A61K 9/0021 604/506 |
| 2010/0256064 | A1* | 10/2010 | Woolfson | A61B 17/205 514/15.2 |
| 2012/0123387 | A1* | 5/2012 | Gonzalez | A61M 37/0015 604/506 |

OTHER PUBLICATIONS

Unknown, SU-8 photoresist, 2017, Wikipedia, https://en.wikipedia.org/wiki/SU-8_photoresist.*

Chandrasekeran, S., et al., "Surface Micromachined Metallic Microneedles", *Journal of Microelectromechanical Systems*, 12(3): 281-288 (Jun. 2003).

Donnelly, R.F., et al., "Microneedle Arrays Allow Lower Microbial Penetration Than Hypodermic Needles in vitro," *Pharm. Res.*, 26(11):2513-2522 (2009).

Donnelly, R.F., et al., "Microneedle-Based Drug Delivery Systems: Microfabrication, Drug Delivery, and Safety," *Drug Deliv.*, 17(4):187-207 (2010).

Donnelly, R.F., et al., Processing difficulties and Instability of Carbohydrate Microneedle Arrays., *Drug Dev. Ind. Pharm.*, 35(10):1242-1254 (2009).

Faraji-Dana S, et al., "UV-curable pressure sensitive adhesive films: effects of biocompatible plasticizers on mechanical and adhesion properties," *Soft Matter*, 9: 6270-6281(2013).

Gill, H.S. and Prausnitz, M.R. "Pocketed Microneedles for Drug Delivery to the Skin," *Journal of Physics and Chemistry of Solids*, 69(5-6)1537-1541 (2008).

Gill, H.S. and Prausnitz, M.R., "Coated Microneedles for Transdermal Delivery," *J. Control Release*, 117(2):227-237 (2007).

Henry, S., et al., "Microfabricated Microneedles: a Novel Approach to Transdermal Drug Delivery," *J. Pharm. Sci.*, 87(8): 922-925(1998).

Ito, Y., et al., "Evaluation of Self Dissolving Needles Containing Low Molecular Weight Heparin (LMWH) in Rats," *Int. J. Pharm.*, 349(1-2):124-129 (2008).

Ito, Y., et al., "Feasibility of Microneedles for Percutaneous Absorption of Insulin," *Eur. J. Pharm. Sci.*, 29(1):82-88 (2006).

Jung, P.G., et al., "Nickel Microneedles Fabricated by Sequential Copper and Nickel Electroless Plating and Copper Chemical Wet Etching," *Sens. Mater.*, 20(1):45-53 (2008).

Kang, L, et al., "Cell Confinement in Patterned Nanoliter Droplets in a Microwell Array by Wiping," *J. Biomed. Mater. Res.*, 93(2):547-557 (2010).

Kang, L., et al., "Formulation Development of Transdermal Dosage Forms: Quantitative Structure Activity Relationship Model for Predicting Activities of Terpenes that Enhance Drug Penetration through Human Skin.," *J. Control Release.*, 120(3): 211-219 (2007).

Kaushik, S., et al., "Lack of Pain Associated with Micro Fabricated Microneedles," *Anesth. Analg.*, 92(2): 502-504 (2001).

Kindernay, J., et al., "Effect of UV Light Source Intensity and Spectral Distribution on the Photopolymerisation Reactions of a Multifunctional Acrylated Monomer," *Journal of Photochemistry and Photobiology: Chemistry*, 151(1-3):229-236 (2007).

Kochhar, J.S., et al., "A Simple Method of Microneedle Array Fabrication for Transdermal Drug Delivery," *Drug Development and Industrial Pharmacy*, 39:299-309 (2013).

Kochhar, J.S., et al., "Direct Microneedle Array Fabrication Off a Photomask to Deliver Collagen Through Skin," *Pharmaceutical Research*, 31(7):1724-1734 (2014).

Kochhar, J.S., et al., "Effect of Microneedle Geometry and Supporting Substrate on Microneedle Array Penetration Into Skin," *Journal of Pharmaceutical Science*, 102(11):4100-4108 (2013).

Kochhar, J.S., et al., "Microneedle integrated transdermal patch for fast onset and sustained delivery of lidocaine," *Molecular Pharmaceutics*, 10 (11): 4272-4280 (2013).

Kolli, C.S., and Banga, A.K., "Characterization of Solid Maltose Microneedles and Their Use for Transdermal Delivery," *Pharm. Res.*, 25(1):104-113 (2008).

Kolomijtseva, G., et al., "Effect of UV-light on the structure of soluble deoxyribonucleoprotein-200," *A. Biokhimiia*, 44(7): 1256-1263 (1979). (English Abstract).

Koutsonanos, D.G., et al., "Transdermal Influenza Immunization With Vaccine-Coated Microneedle Arrays," PLoS One 4(3):e4773 (2009).

Lee, J.W., et al., "Dissolving in Microneedles for Transdermal Drug Delivery," *Biomaterials* 29(13):2113-2124 (2008).

Li, G., et al., "In vitro Transdermal Delivery of Therapeutic Antibodies Using Maltose Microneedles," *International Journal of Pharmaceutics*, 368(1-2):109-115 (2009).

Martanto, W., et al., "Transdermal Delivery of Insulin Using Microneedles in vivo.," *Pharm. Res.*, 21(6): 947-952 (2004).

McGrath, M.G., et al., "Determination of Parameters for Successful Spray Coating of Silicon Microneedle Arrays," *Int. J. Pharm*, 415(1-2):140-149 (2011).

McGrath, M.G., et al., "Spray Coating of Silicon Microneedle Patches for Intradermal Drug Delivery," *Journal of Pharmacy and Pharmacology*, 62(6):798-798 (2010).

Miyano, T., et al., "Sugar Micro Needles as Transdermic Drug Delivery System," *Biomedical Microdevices*, 7(3):185-188 (2005).

Paik, S.J., et al., "In-Plane Single-Crystal-Silicon Microneedles for Minimally Invasive Microfluid Systems," *Sens. Actuator A-Phys.* 114(2-3): 276-284 (2004).

Pan, J., et al., "Fabrication of a 3D hair follicle-like Hydrogel by soft lithography", *Journal of Biomed Mater. Res.*, Part A 101(11): 3159-3169 (2013).

Park, J.H., et al., "Biodegradable Polymer Microneedles: Fabrication, Mechanics and Transdermal Drug Delivery.," *J. Control Release*, 104(1):51-66 (2005).

Park, J.H., et al., "Polymer Microneedles for Controlledrelease Drug Delivery," *Pharm. Res.* 23(5):1008-1019 (2006).

Parker, E.R., et al., "Bulk Micromachined Titanium Microneedles," Journal of Microelectromechanical Systems, 16(2): 289-295 (2007).

Prausnitz, M.R. and Langer, R., "Transdermal Drug Delivery," *Nat. Biotechnol.*, 26(11):1261-1268 (2008).

Prausnitz, M.R., et al., "Current Status and Future Potential of Transdermal Drug Delivery," *Nat Rev Drug Discov.*, 3(2): 115-124 (2004).

Shikida, M., et al., "Fabrication of a Hollow Needle Structure by Dicing, Wet Etching and Metal Deposition," *J. Micromech. Microeng.* 16(10):2230-2239 (2006).

Shikida, M., et al., "Non-photolithographic pattern transfer for fabricating arrayed three-dimensional microstructures by chemical anisotropic etching," *Sensors and Actuators A: Physical*, 116(2):264-271 (2004).

Sullivan, S.P., et al., "Dissolving Polymer Micro Needle Patches for Influenza Vaccination," *Nat Med.*, 16(8): 915-920 (2010).

Sullivan, S.P., et al., "Minimally Invasive Protein Delivery with Rapidly Dissolving Polymer Microneedles," *Adv. Mater.*, 20(5): 933-938 (2008).

Wei-Ze, L., et al., "Super-Short Solid Silicon Microneedles for Transdermal Drug Delivery Applications," *International Journal of Pharmaceutics*, 389(1-2):122-129 (2010).

Wermeling, D.P., et al., "Microneedles Permit Transdermal Delivery of a Skin-Impermeant Medication to Humans," *Proc Natl Acad Sci, USA*, 105(6): 2058-2063 (2008).

(56) References Cited

OTHER PUBLICATIONS

Wilke, N., et al., "Process Optimization and Characterization of Silicon Microneedles Fabricated by Wet Etch Technology," *Microelectronics Journal*, 36(7):650-656 (2005).

International Search Report and the Written Opinion of the International Searching Authority dated May 7, 2013 for International Application No. PCT/SG2013/000108 filed Mar. 15, 2013, entitled "A Novel Method to Fabricate Polymeric Microneedles".

International Preliminary Report on Patentability dated Sep. 16, 2014 for International Application No. PCT/SG2013/000108 entitled "A Novel Method to Fabricate Polymeric Microneedles".

* cited by examiner

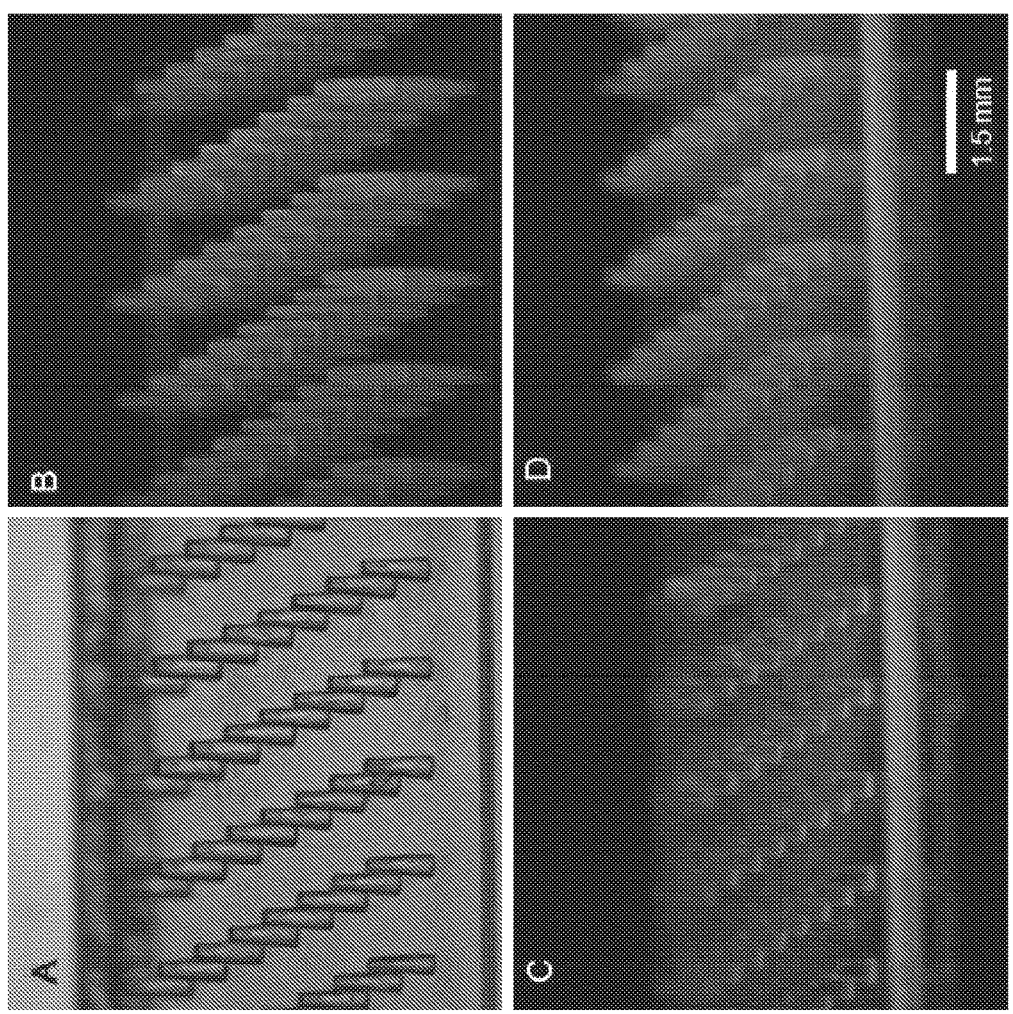
FIG 3A-D

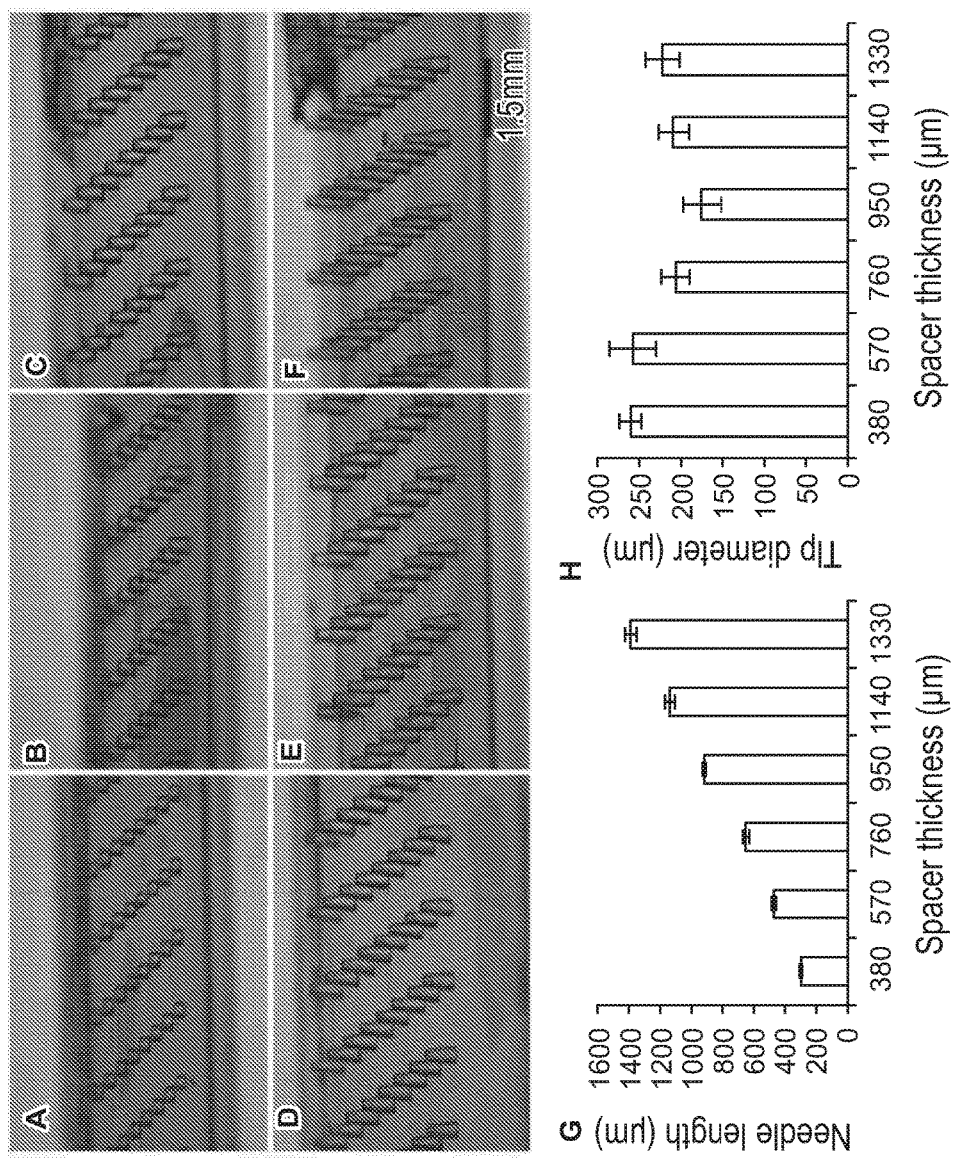
FIG. 6A – H

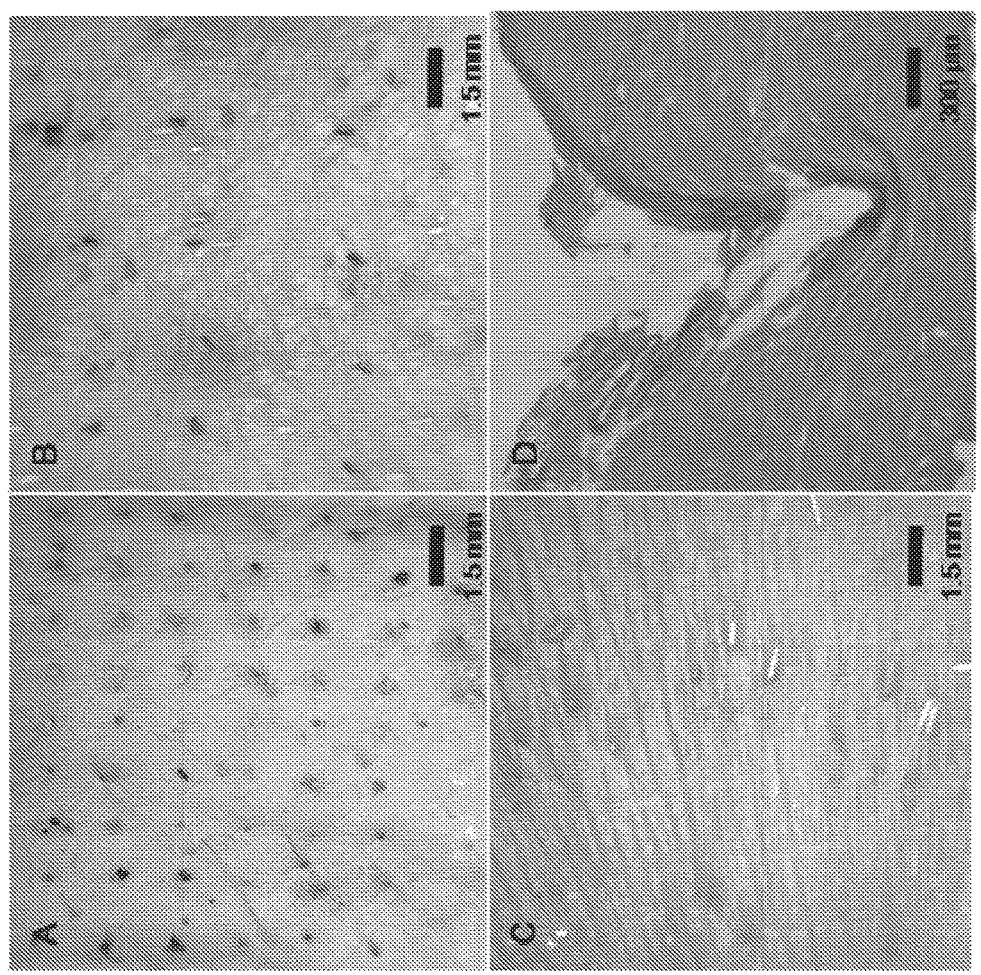
FIG 7A-D

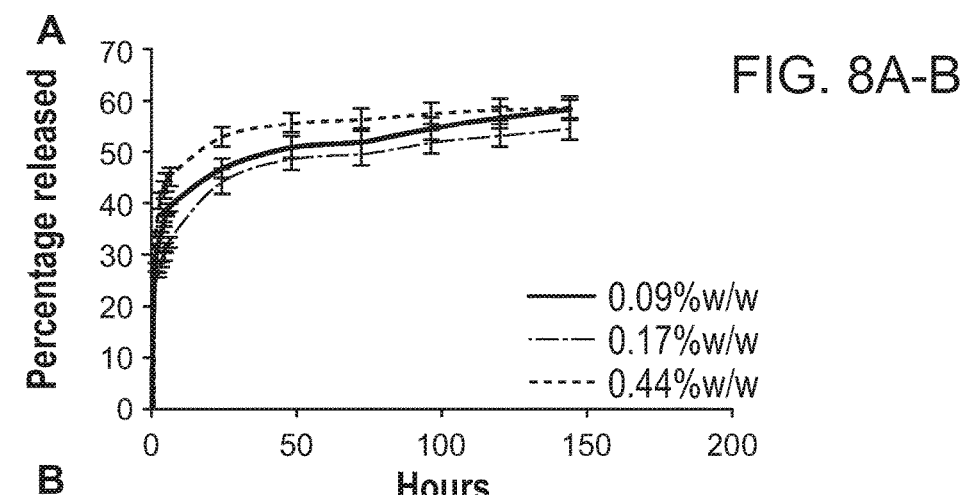
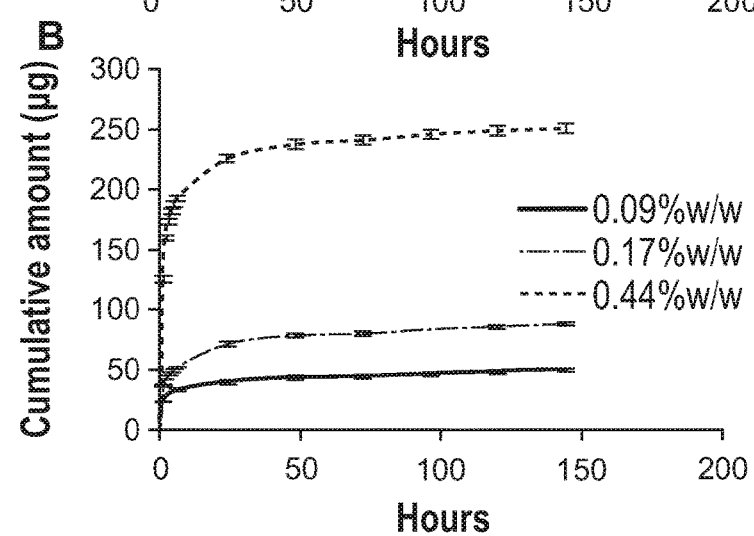
FIG. 8A-B
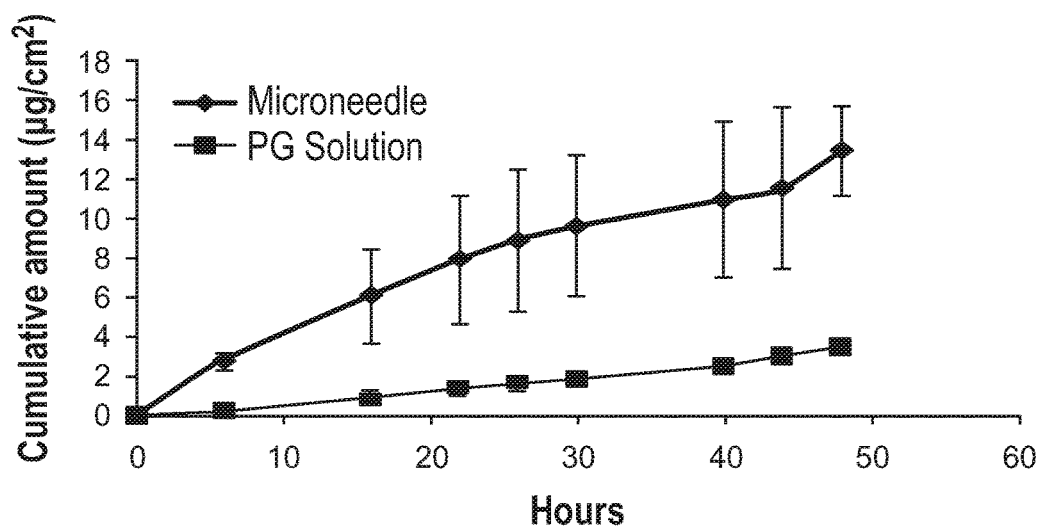
FIG. 9

FIG. 10A-F

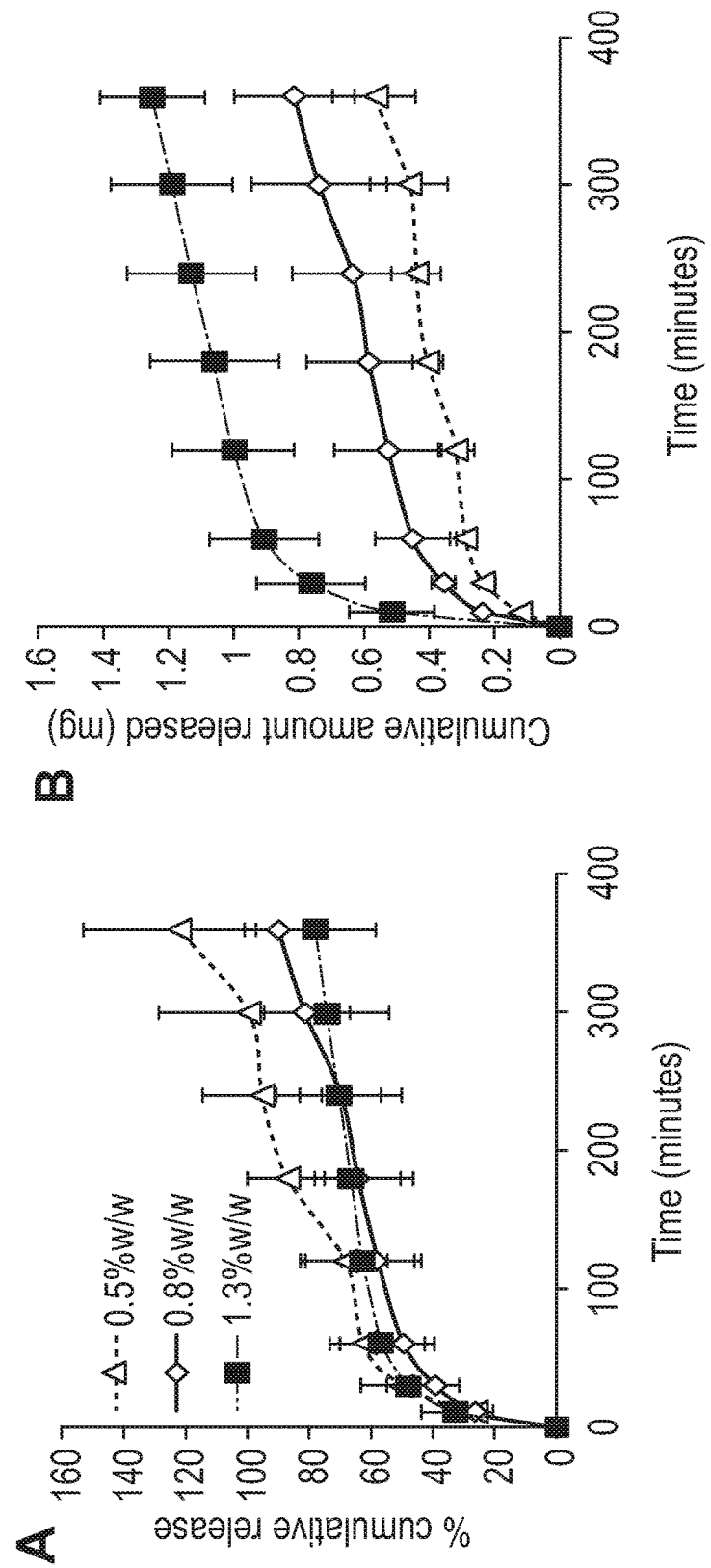
FIG. 14A-B

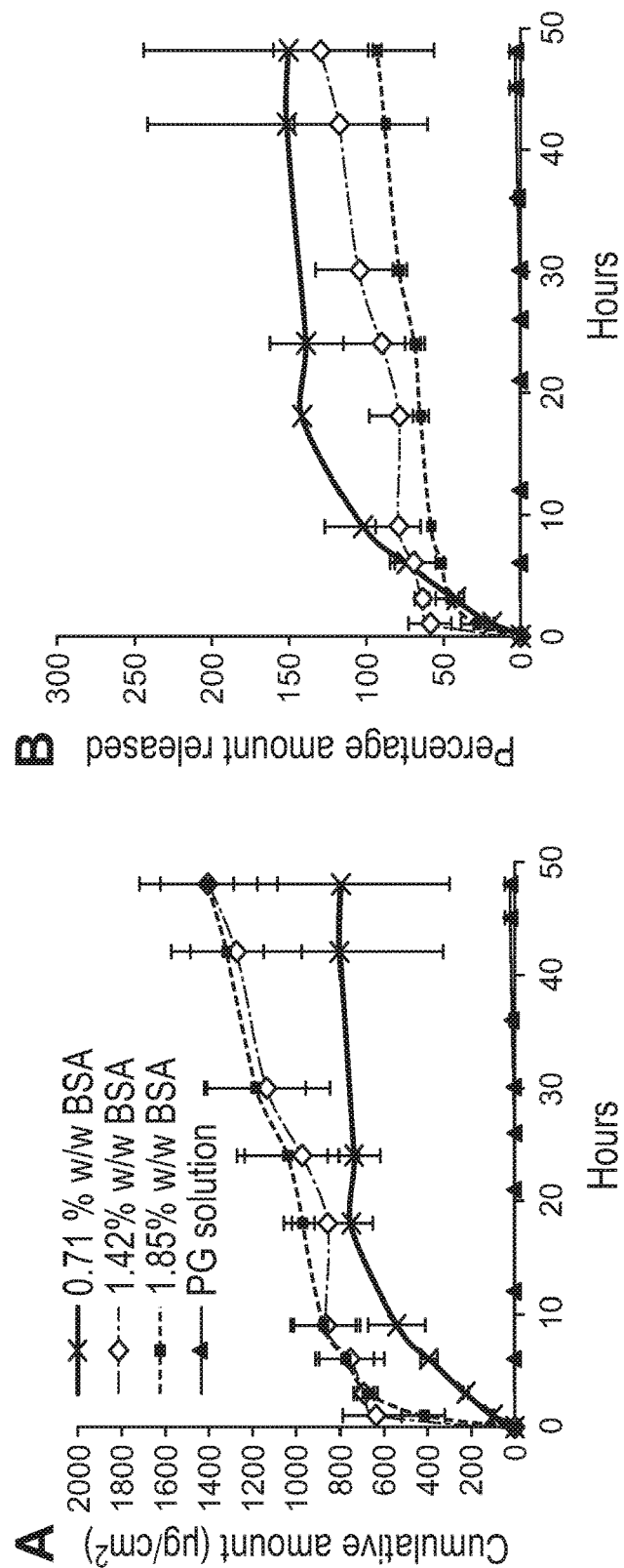
FIG. 15A-B

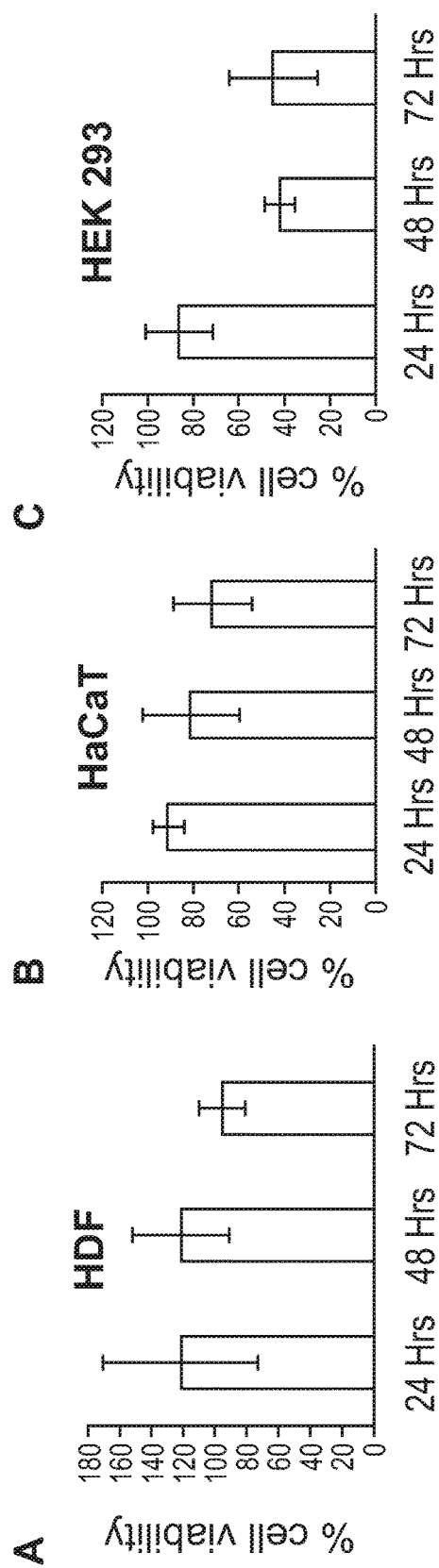
FIG. 16A-C

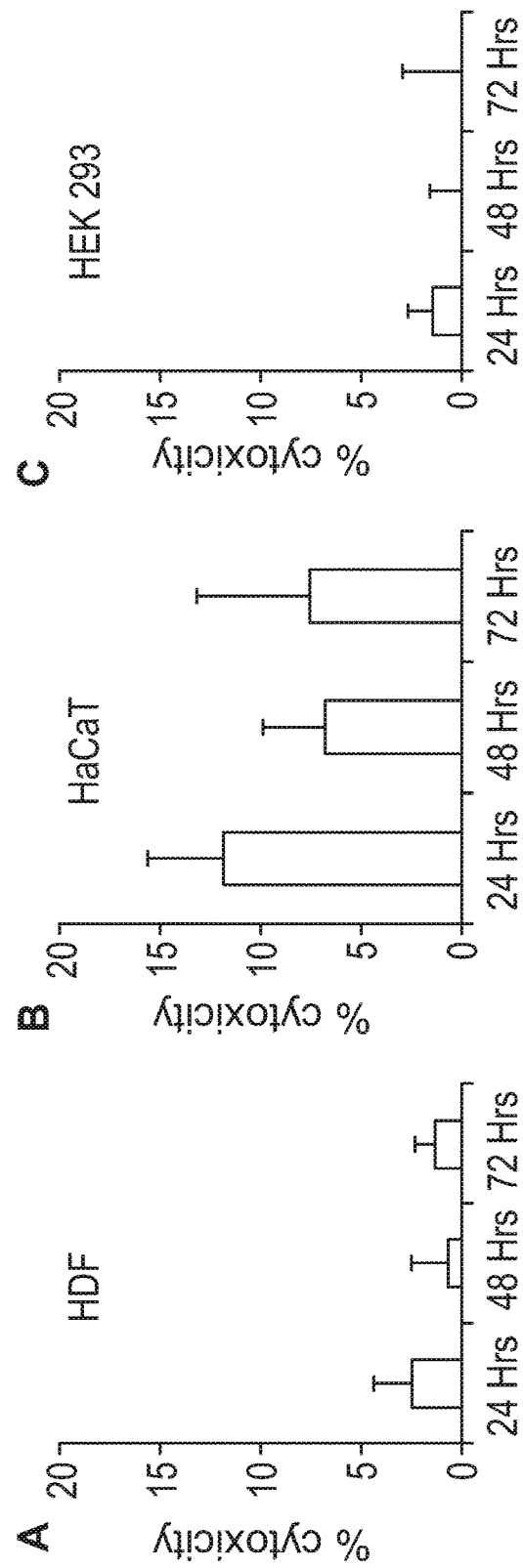

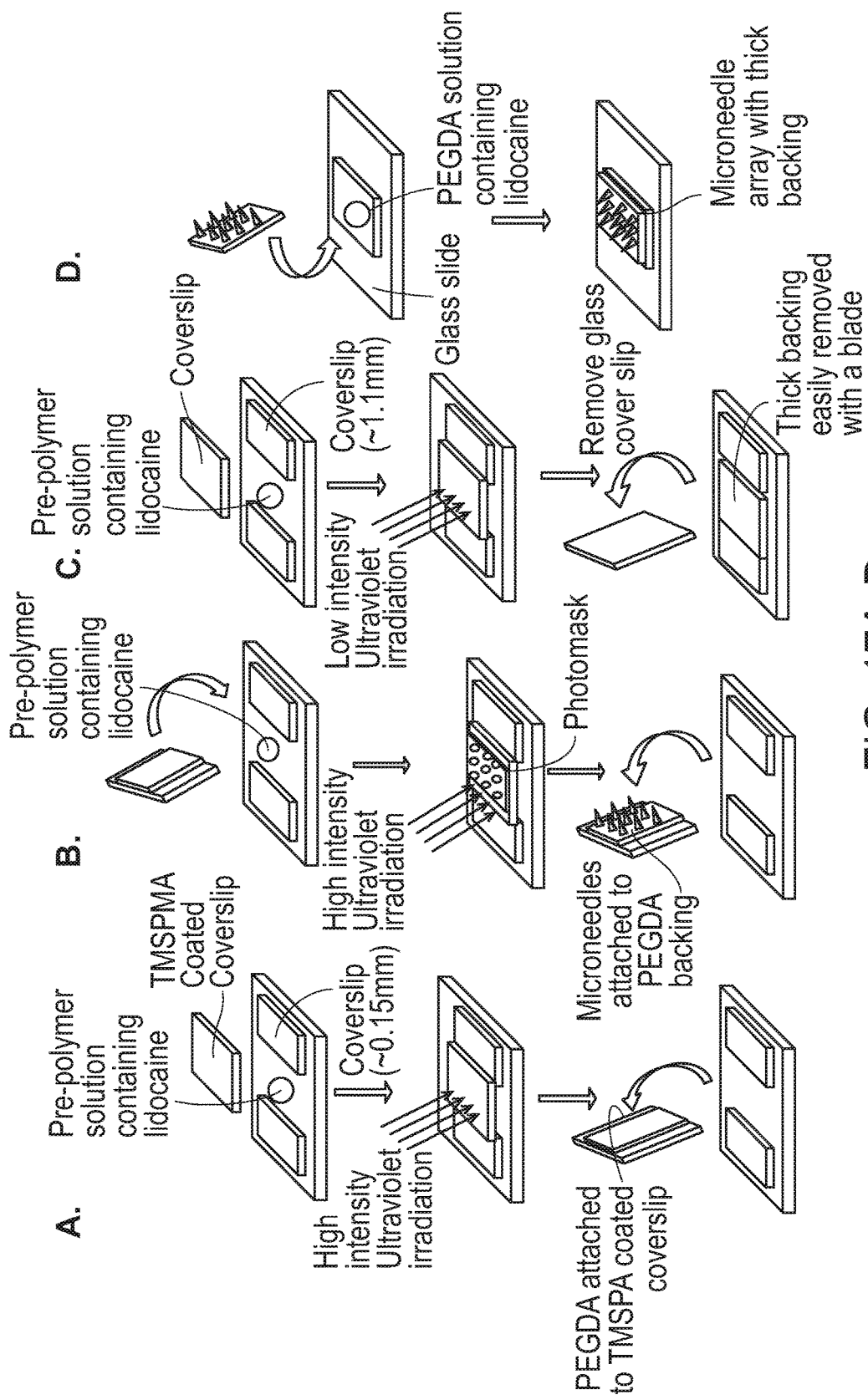
FIG. 17A-D

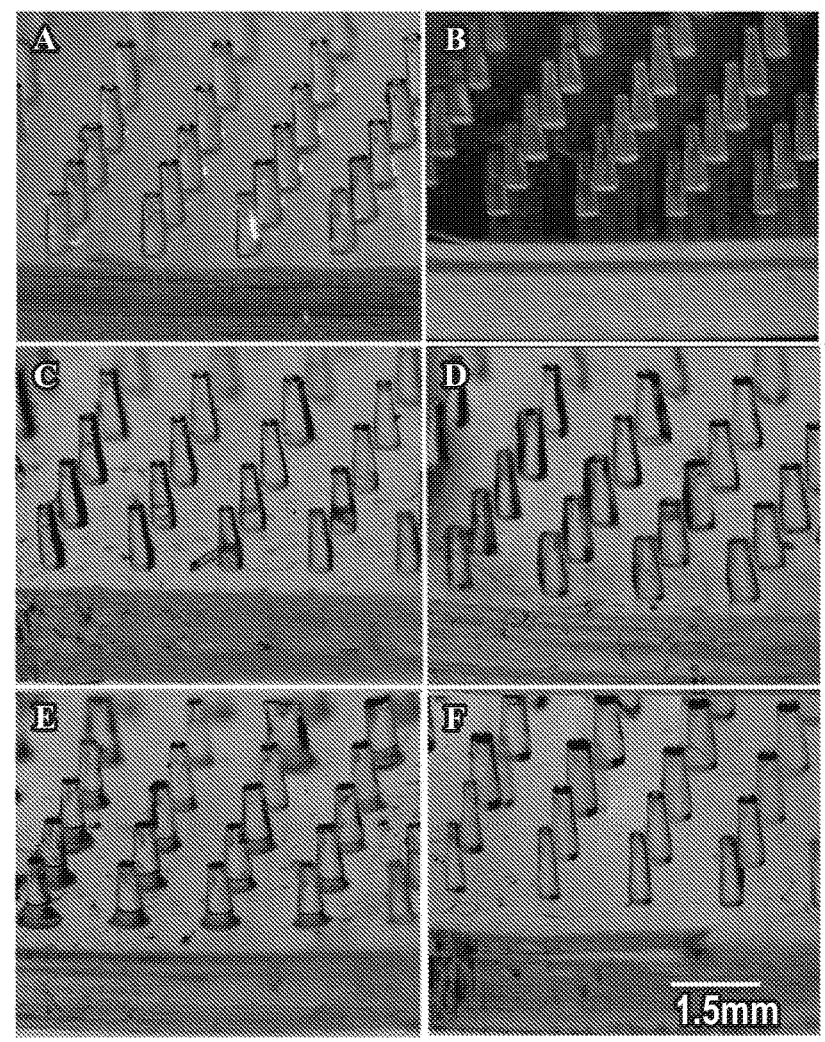
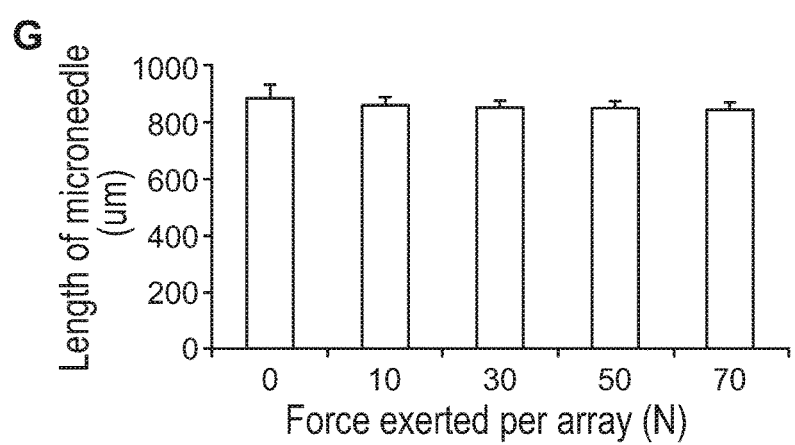
FIG. 18A-G

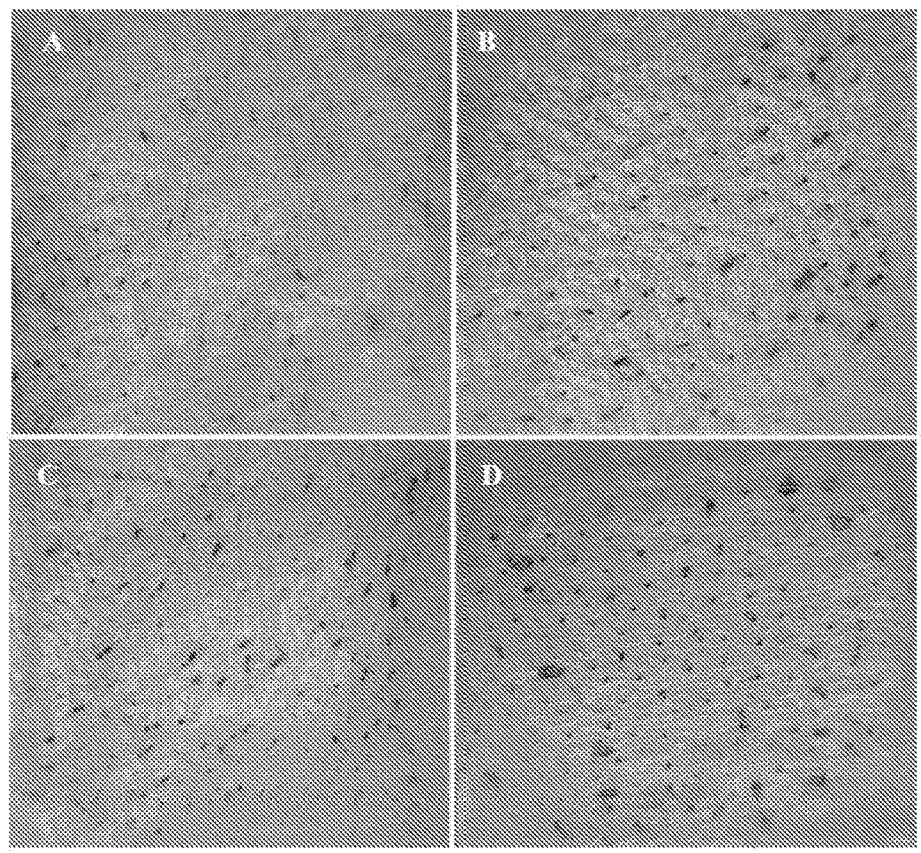
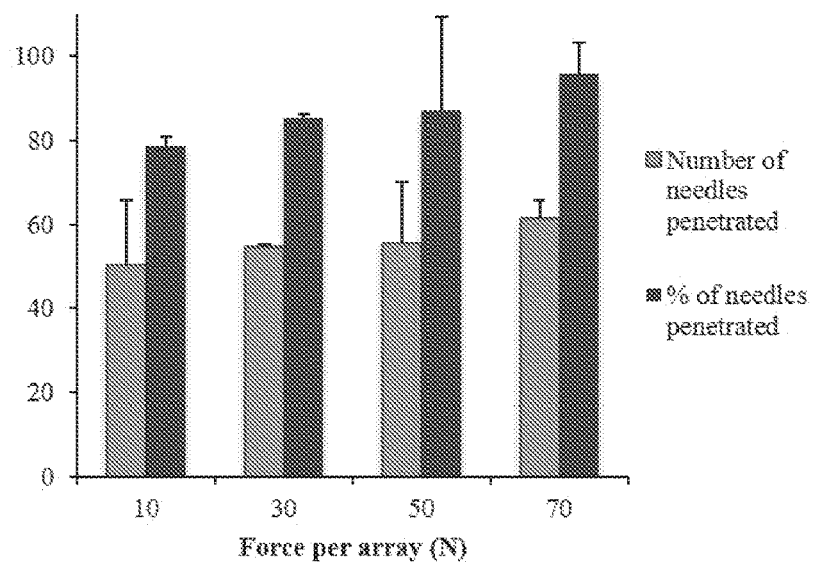
FIG 19 A-E

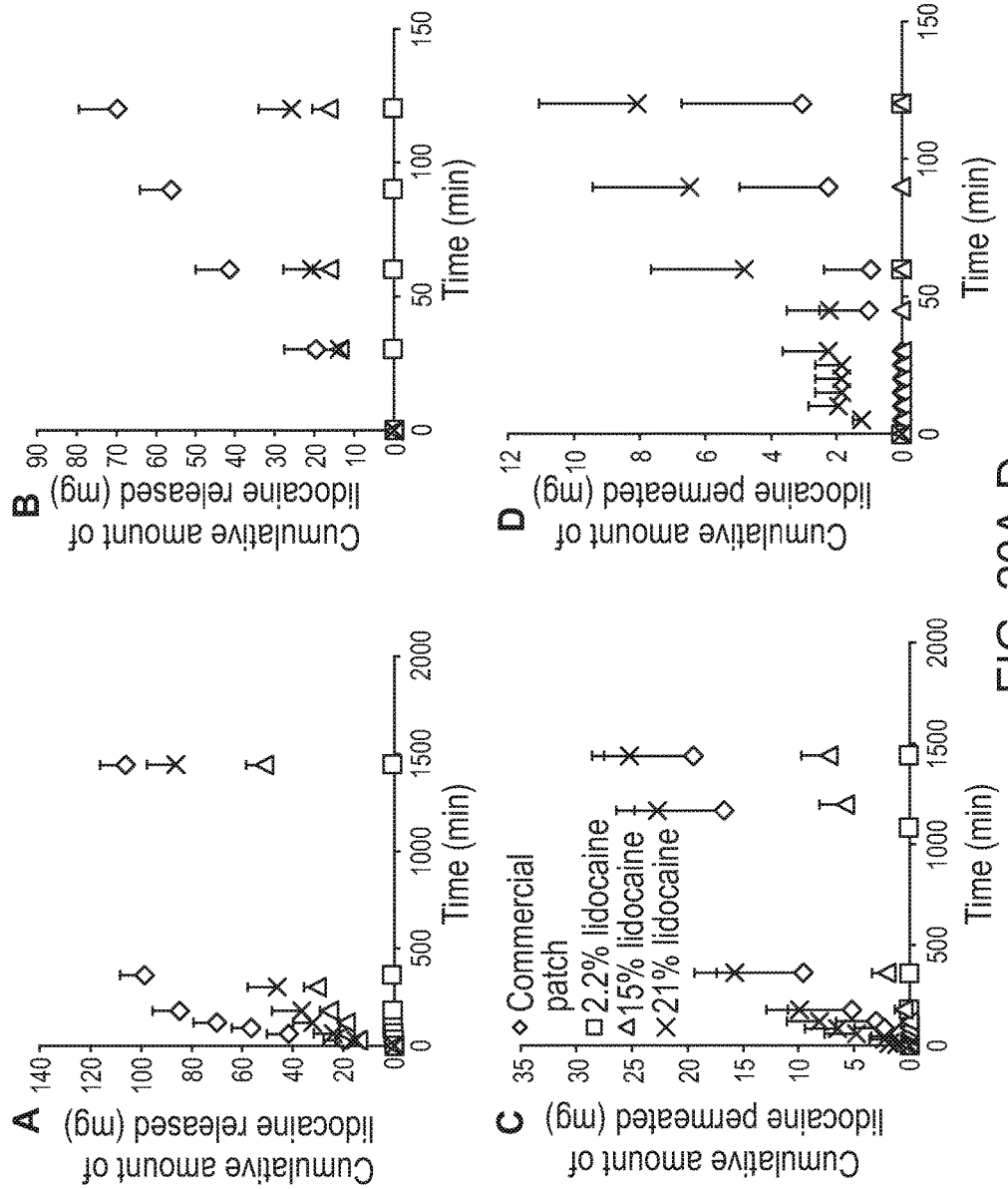
FIG. 20A-D

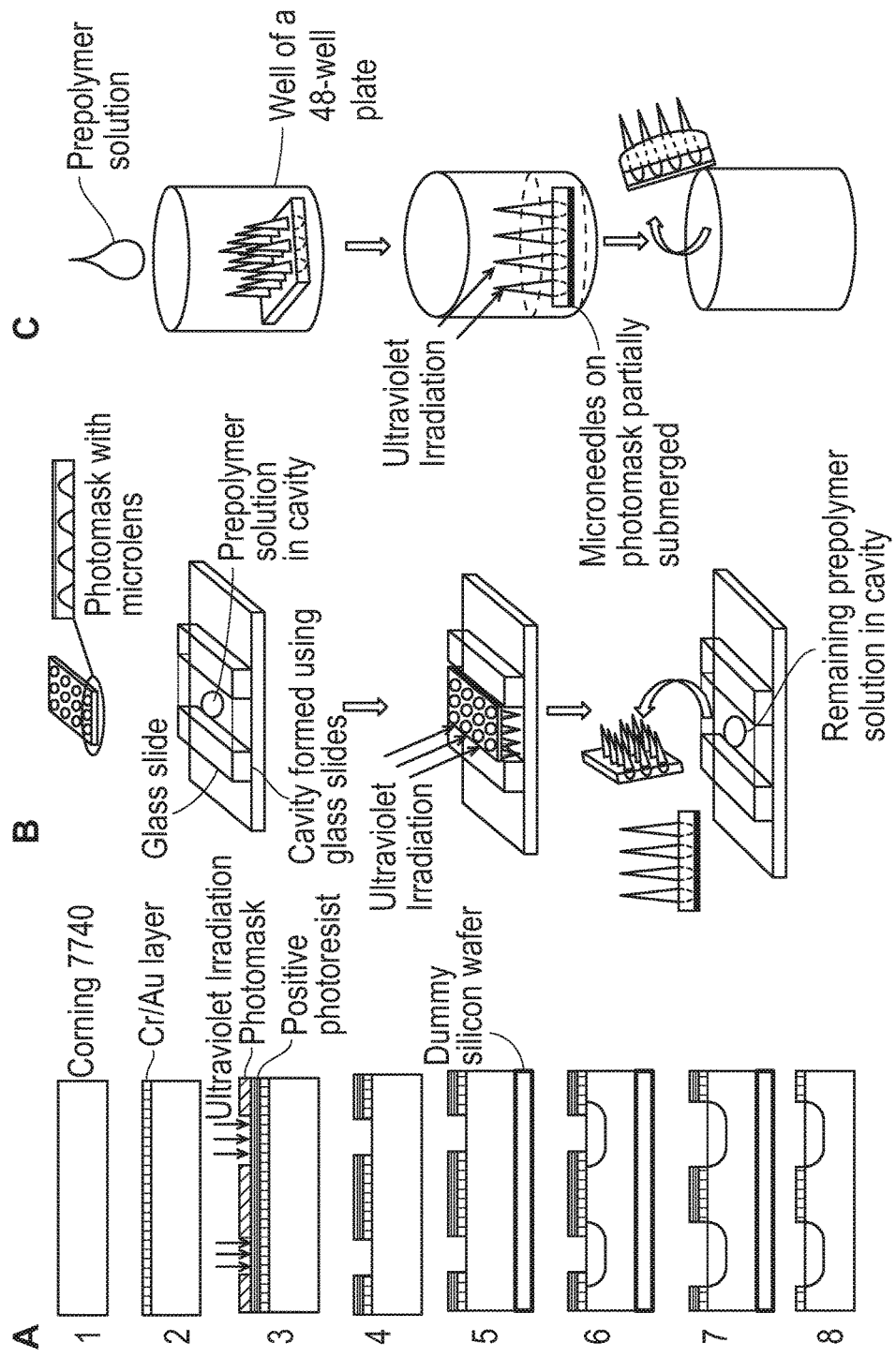
FIG. 22A-C

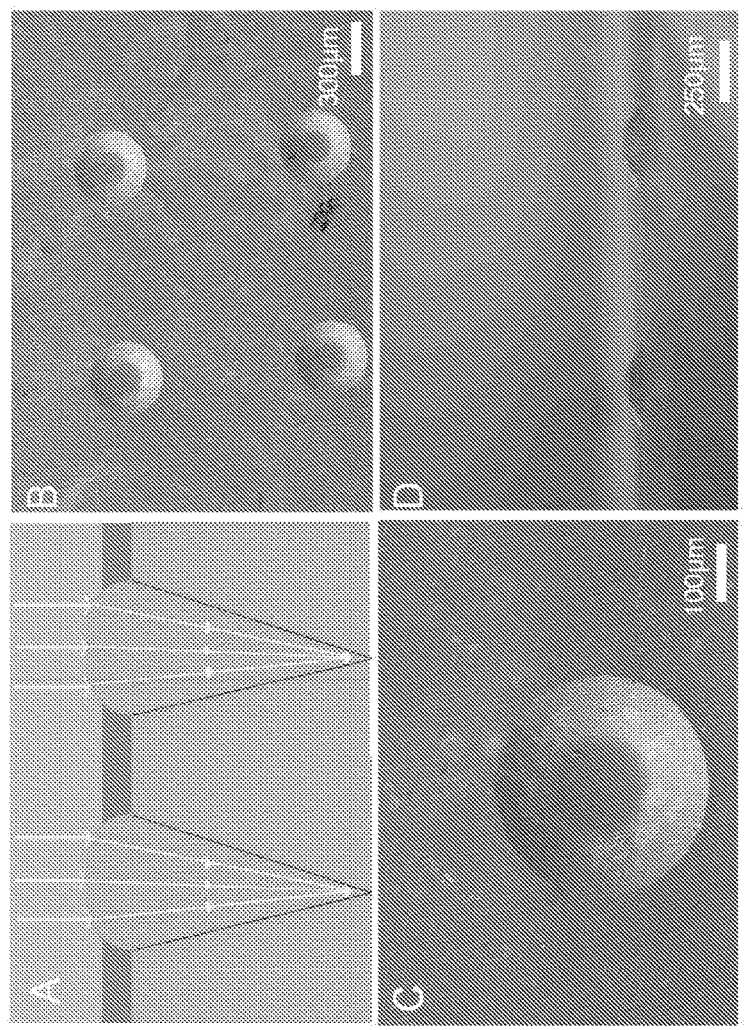
FIG 23 A-D

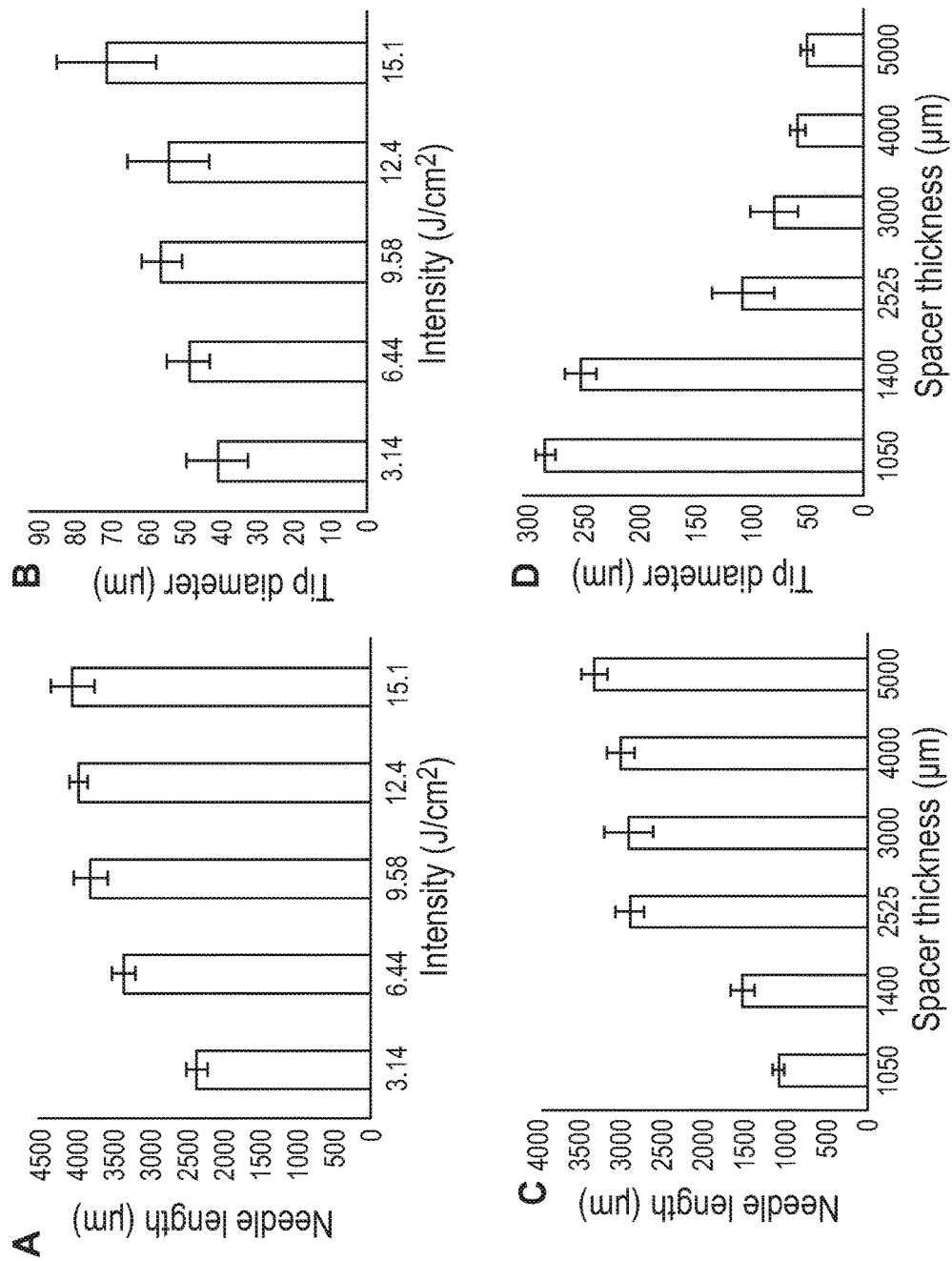
FIG. 24A-D

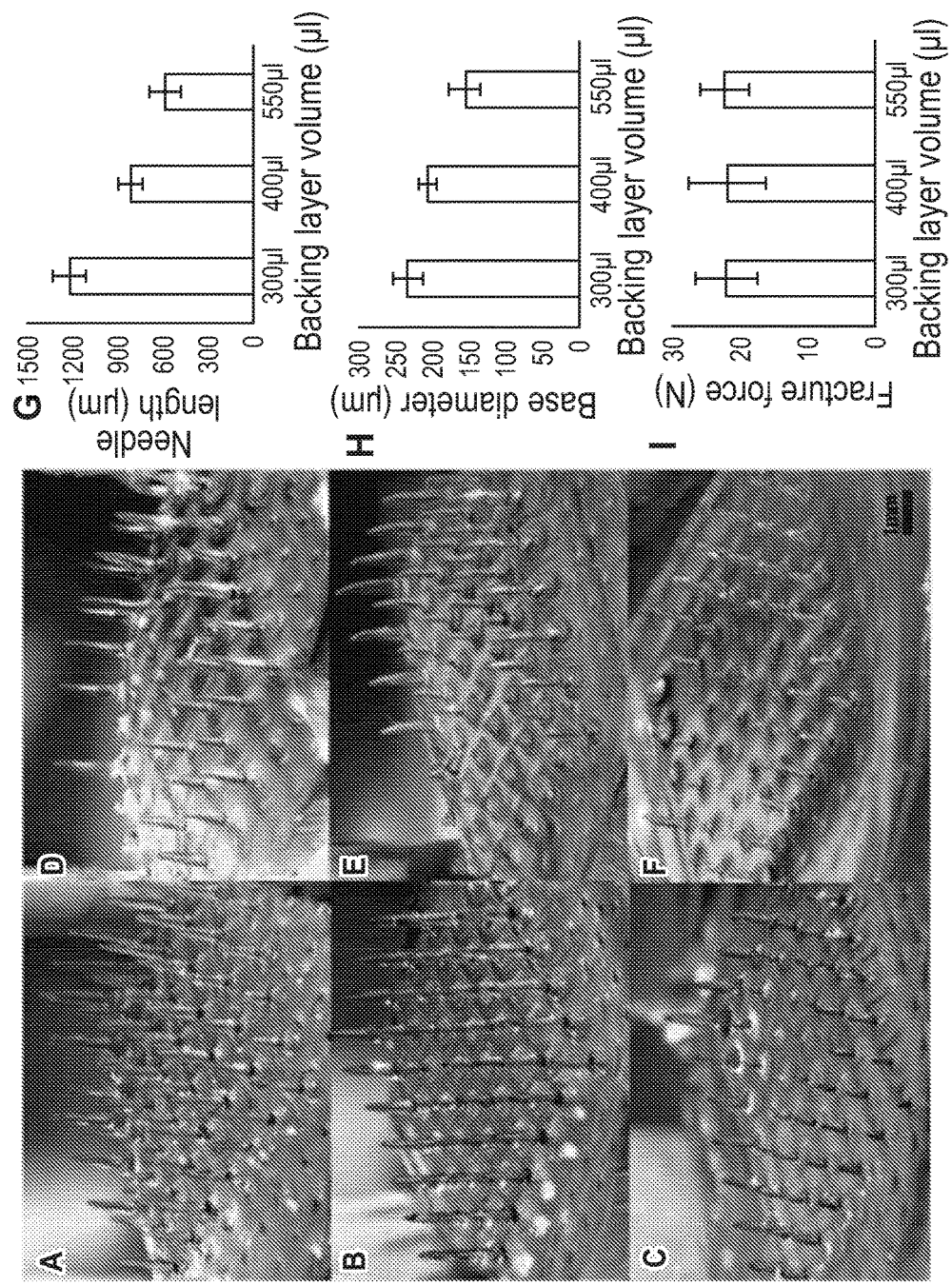
FIG. 25A-I

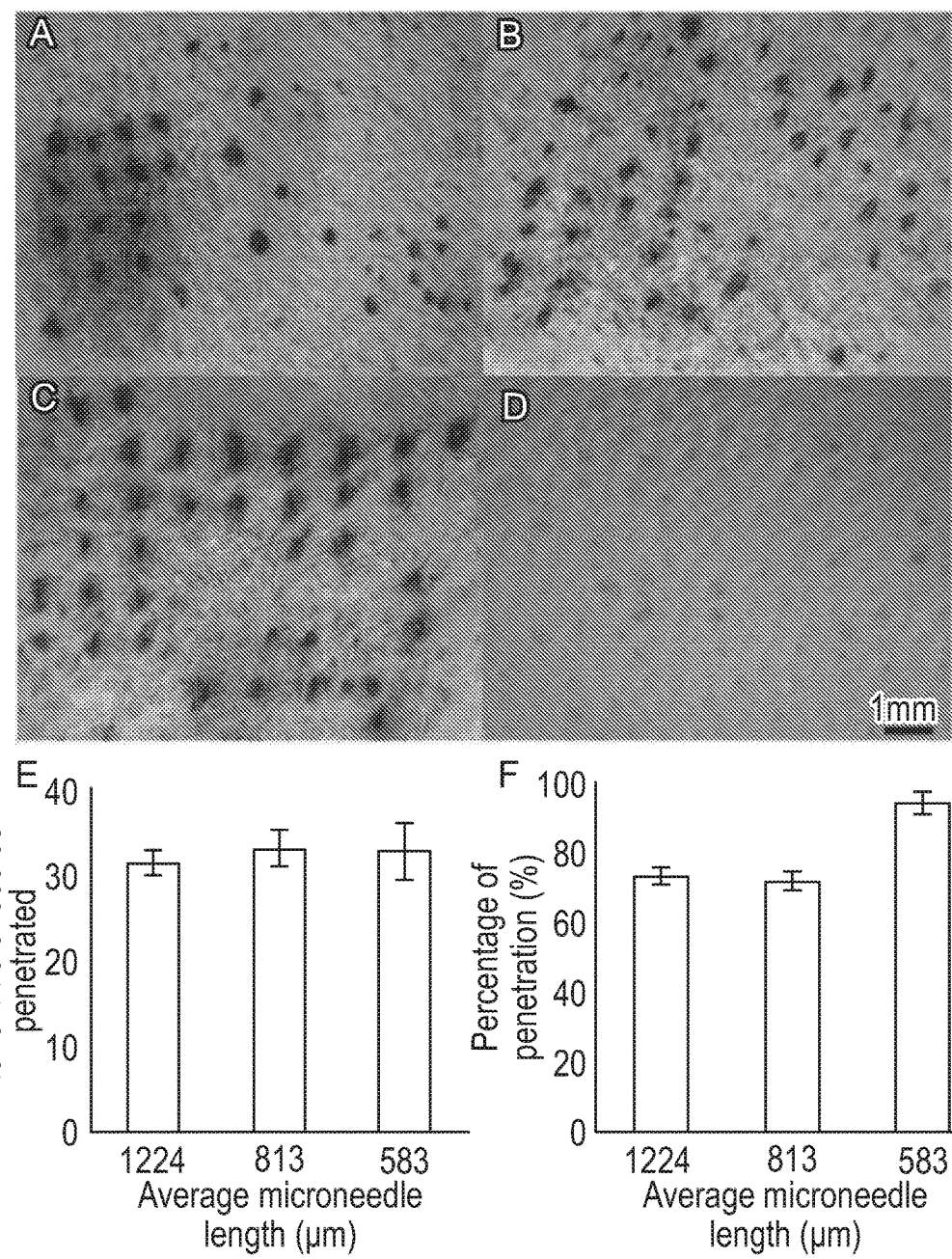
FIG. 26A-F

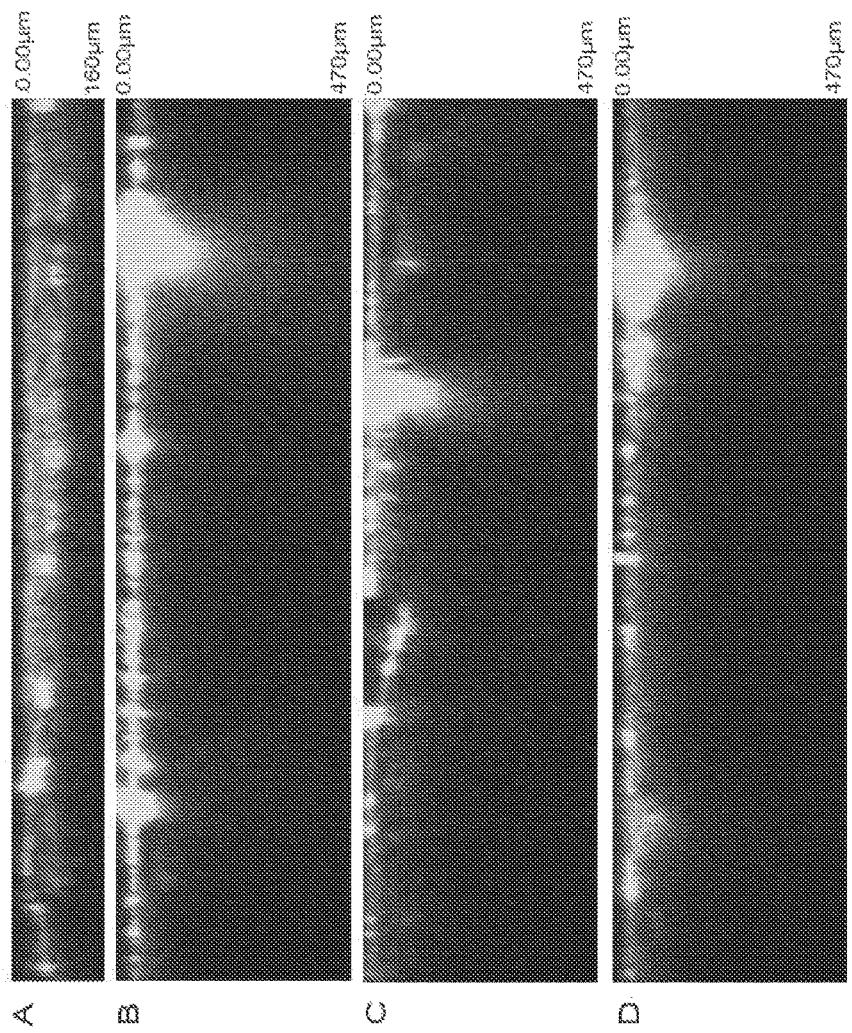
FIG 27 A-D

METHOD TO FABRICATE POLYMERIC MICRONEEDLES

RELATED APPLICATIONS

This application is the U.S. National Stage of International Application No. PCT/SG2013/000108, filed Mar. 15, 2013, which designates the U.S., published in English, and claims the benefit of U.S. Provisional Application No. 61/611,603, filed Mar. 16, 2012.

TECHNICAL FIELD

The present disclosure relates generally to microneedle devices and methods for fabricating microneedles from a biocompatible polymer using photolithography. More particularly, aspects of the present disclosure are directed to the fabrication of microneedle devices using a biocompatible polymer (biopolymer) by way of biocompatible, essentially biocompatible, or substantially biocompatible fabrication techniques. In accordance with particular embodiments of the present disclosure, microneedle devices are fabricated, which can carry biosubstances such as drugs/proteins (e.g., Rhodamine B or Bovine Serum Albumin (BSA)), for instance, on and/or within microneedle shafts and/or a microneedle backing layer. Biocompatible, essentially biocompatible, or substantially biocompatible fabrication processes can include ultra violet based photo-crosslinking of polymers through a patterned mask for a limited amount of time in order to ensure high biosubstance structural and/or functional integrity or stability. The patterned mask facilitates the development of a specific pattern in the biopolymer, which results in the formation of micron scale needle structures or microneedles. In multiple embodiments, biocompatible polymers used to fabricate microneedles include poly (ethylene glycol) (PEG) based polymers.

BACKGROUND

With the advent of new biotechnology methods and recombinant technologies, many new and potent biotherapeutics are being synthesized. Pharmaceutical scientists are posed with the challenge of developing novel drug delivery systems to effectively deliver these molecules to sites of action. These new delivery systems must be capable of overcoming biochemical and anatomic barriers to aid drug transport, control the rate and duration of drug release, prevent the macromolecules from enzymatic or in situ degradation, and deliver the drug to the target site.

Oral drug delivery has been the most successful to date in delivering conventional drugs. These new biotherapeutics however, are susceptible to degradation in the harsh acidic and enzymatic environment of the gastrointestinal tract and first pass metabolism in the liver leading to low bioavailability.

In comparison, hypodermic injections are a more effective drug delivery system, since drugs delivered by intravenous injections bypass first pass metabolism. However, hypodermic injections have their own limitations. These include pain, risk of infection, need of trained personnel for drug administration as well as requirements for sharps disposal.

As a result of these limitations, a more effective drug delivery method is sought after with little or none of the limitations of the hypodermic needles or by oral delivery routes. Transdermal drug delivery has evolved to have a significant impact in the drug delivery horizon and is competing to provide a viable alternative to oral delivery and hypodermic injection. Delivering a drug through this route offers several advantages such as the avoidance of premature metabolism of drugs in gut and liver leading to dose sparing and is less painful than hypodermic injections which generate dangerous biomedical waste and pose the risk of transmission of disease if the needles are reused. Transdermal systems are non-invasive and are amenable to self administration, thus increasing patient compliance and reducing medical costs.

Transdermal delivery systems include topical formulations and more recently, transdermal patches. Topical formulations such as gels, ointments and creams have been used for decades now and have been successful for local and short term treatment with small, lipophilic and low-dose drugs. Transdermal patches have been approved for sale for lipophilic drugs such as scopolamine, nicotine, fentanyl as well as estradiol and have been widely used for a variety of conditions. Each year more than 1 billion transdermal patches are being manufactured and a new patch has been approved every 7.5 months between 2003-2007.

Despite being advantageous in a variety of conditions, these transdermal drug delivery systems have not been adapted for novel biotherapeutics such as proteins, peptide and vaccines. These new compounds cannot cross the biological barrier of stratum corneum at therapeutically useful rates due to their hydrophilicity and large molecular weights. The outermost layer of epidermis, the stratum corneum is 10-15 μm thick and prevents molecules larger than 400 Da to passively diffuse to the subcutaneous tissues. This is exemplified by the fact that the smallest drug currently manufactured in a patch is nicotine (162 Da) and the largest is oxybutynin (359 Da). Creating delivery systems to deliver these big molecules has been a major challenge to formulation scientists in the past decade.

To deliver these big molecules, an array of methods has been researched, including chemical penetration enhancers, iontophoresis, ultrasound, laser and electroporation. Numerous chemical excipients in pharmaceutical formulations that disrupt the bilayer structures of stratum corneum have been studied for their permeation enhancing effects. The major drawback with these chemical agents is the accompanied skin irritation, which correlates with increased permeation. Iontophoresis, which primarily depends upon an electrical force driving the charged molecules across the stratum corneum, has also been limited in application for large molecules due to limited ability to disrupt the skin barrier. It has been thus used for molecules weighing only a few thousand Daltons. Ultrasound, which is an oscillating pressure wave, has been thought to increase skin permeability by generating pressure gradients and oscillations that drive the drug molecules into the skin. Like iontophoresis, ultrasound has also been able to increase the permeability of small lipophilic drug molecules. Electroporation uses short, high voltage pulses to disrupt lipid bilayers of stratum corneum aiding the diffusion of lipophilic as well as hydrophilic drugs. However, the associated pain due to high electric field and the resulting muscle stimulation is an area of concern and the technique has not been widely researched due to complex requirements of the device setup. Although all these methods are conceptually sound, none of them has been able to make a convincing impact in delivering high molecular weight and hydrophilic molecules across the stratum corneum.

Recently, high precision microelectronic tools and miniaturization techniques, first adapted in the semiconductor industry, have been tailored to design micron scale drug delivery systems such as microneedles. Microneedles are small micron scale devices consisting of numerous projections, where the height and shape of such projections are governed by the fabrication process. Microneedles are applied to the skin in a manner similar to the transdermal patch, and create pores in micron scale range in the stratum corneum, thereby allowing the passage of hydrophilic as well as large molecular weight drugs through the skin and mimicking aspects of hypodermic needles. Microneedles can therefore be considered to be a hybrid drug delivery system between the safe and convenient transdermal patch and efficient hypodermic injections.

Since microneedles are in the micron scale (600-700 microns long, 10-60 micron tip diameter), they do not penetrate deep enough into the skin to stimulate pain receptors and hence are relatively pain free. Trauma to the application site is also low due to the small size of microneedles, and hence wound healing is relatively fast. It has also been shown that transient pores created by microneedles close within 72 hours after removal of the microneedles. This makes the use of microneedles very appealing to patients with impaired healing or requiring frequent injections such as diabetic patients. Lastly, microneedles do not require specialized training for use.

A drug moiety can either be coated on the microneedles or encapsulated in their core and delivered to the subcutaneous tissues. The microneedles are expected to evade any nerve fibers or blood vessels that reside in the dermal layer due to their small size, and this has been clinically proven in a previous study.

Many research groups have extensively studied and used various materials and fabrication techniques. Microneedles have been fabricated from silicon, metals, zeolite and polymers. The widespread use of silicon in the microelectronics industry and its relatively low cost made it a suitable material for microneedle fabrication in the early stages of development of microneedles.

Polymeric microneedles have received much attention from the drug delivery scientists in the recent years with several methods being developed to fabricate microneedles from polymers. Various polymers including poly (vinyl pyrrolidone), its co-polymer with methacrylic acid and polylactide-co-glycolide have been used. Sugars and sugar derivatives like dextrose, maltose, galactose, carboxymethylcellulose and amylopectin have also been used for fabricating microneedles. These materials used are biocompatible, cost effective and generate no biohazardous waste.

Drugs have been delivered by either coating on to the shafts of the silicon or metallic microneedles. However, with this approach, only a limited amount of drug could be loaded on to the microneedle shafts, curtailing significant drug dosage. Another approach involved pre-treating the skin with microneedles to create transient pores and drugs were applied in the form of drug solutions. The brittle nature of silicon and metallic microneedle is a serious concern. These materials are not biodegradable and their biocompatibility is questionable, involving the risk of if they break in the skin or are inadvertently misused. On the other hand, polymeric microneedles have been used encapsulate the drugs in addition to drug coating and pre-treatment of skin with their predecessors. Most of these previously developed polymeric microneedles focused on protein drugs such as insulin, heparin and vaccines. They have been shown release the load when inserted in to the skin. The drugs released from the microneedles can form a depot from where they can be absorbed to systemic circulation or lymphatic vessels. Encapsulation of drugs within the polymeric core offers the advantage of higher drug loading and the convenience of formulation omitting multiple steps. Hence encapsulation of drugs within the microneedles has received most attention from the transdermal drug delivery scientists in the past 2-3 years. However the fabrication approaches used for these microneedles were harsh, and cannot be generalized to ensure the stability of proteins. High temperatures (150-160° C.) have been used for micromolding of sugar microneedles, whereas long exposures to ultraviolet light have been used for microneedles developed from poly (vinylpyrrolidone). Casting methods used by other groups utilize polymers or sugar derivatives requiring the concentration of hydrogel using high temperature and vacuum which have been shown their deleterious effects on the fragile protein molecules. Other complex procedures like wet silicon etching, reactive ion etching and laser based methods involve elaborate processing which accrue the overall cost of the process.

SUMMARY

A first aspect of the present disclosure provides a method for microneedle device fabrication that can include: providing a backing structure; contacting at least one microneedle forming biocompatible polymer with a surface of the backing structure to form a microneedle forming biocompatible polymer layer on the surface of the backing structure, the microneedle forming biocompatible polymer layer having a thickness, the microneedle forming biocompatible polymer layer chemically coupleable to the backing structure; and performing an exposure process comprising selectively directing electromagnetic energy into portions of each of the backing structure and the biocompatible polymer layer to form a set of microneedles within the biocompatible polymer layer, wherein the set of microneedles comprises crosslinked biocompatible polymer material suitable for penetration into skin in the substantial absence of additional fabrication processes directed to forming the set of microneedles other than removal of non-crosslinked biocompatible polymer material from the set of microneedles.

In embodiments, the method of the present disclosure described above can include wherein at least one of the backing structure and the microneedle forming biocompatible polymer layer carries at least one biosubstance prior to performing the exposure process, and wherein the exposure process comprises directing electromagnetic energy into portions of the backing structure and the microneedle forming biopolymer layer in a manner that avoids significant degradation of the at least one biosubstance.

In embodiments, the method of the present disclosure described above can include wherein at least one of the backing structure and the microneedle forming biocompatible polymer layer carries at least one biosubstance prior to performing the exposure process, and wherein the exposure process is performed in a manner that maintains at least approximately 80% of the structural and functional integrity of the at least one biosubstance.

In embodiments, the method of the present disclosure described above can include wherein the exposure process is performed in a manner that maintains at least approximately 90% of the structural and functional integrity of the at least one biosubstance.

In embodiments, the method of the present disclosure described above can include wherein the exposure process is performed in a manner that maintains at least approximately 95% of the structural and functional integrity of the at least one biosubstance.

In embodiments, the method of the present disclosure described above can include maintaining during each step of microneedle device fabrication the at least one biosubstance at a temperature below a biosubstance degradation threshold temperature at which significant biosubstance degradation is expected to occur.

In embodiments, the method of the present disclosure described above can include wherein the biosubstance degradation threshold temperature is approximately 40° C.

In embodiments, the method of the present disclosure described above can include wherein the biosubstance degradation threshold temperature is approximately 30° C.

In embodiments, the method of the present disclosure described above can include wherein the biosubstance degradation threshold temperature is approximately 27° C.

In embodiments, the method of the present disclosure described above can include avoiding exposing the at least one biosubstance to reactive plasma species and Carbon-based chemical solvents.

In embodiments, the method of the present disclosure described above can include at least substantially avoiding exposing the at least one biosubstance to a solvent other than water.

In embodiments, the method of the present disclosure described above can include avoiding exposing the at least one biosubstance to a solvent other than water.

In embodiments, the method of the present disclosure described above can include wherein each step of microneedle device fabrication occurs outside of a cleanroom environment.

In embodiments, the method of the present disclosure described above can include wherein performing the exposure process comprises a set of exposure event, each exposure event comprising directing electromagnetic energy into portions of the backing structure and the microneedle forming biopolymer layer for a period of time expected to avoid significant degradation of the at least one biosubstance.

In embodiments, the method of the present disclosure described above can include wherein performing the exposure process includes a single exposure event.

In embodiments, the method of the present disclosure described above can include wherein performing the exposure process comprises avoiding exposing the at least one biosubstance to more than approximately 60 Joules of ultraviolet light energy.

In embodiments, the method of the present disclosure described above can include wherein performing the exposure process comprises avoiding exposing the at least one biosubstance to more than approximately 50 Joules of ultraviolet light energy.

In embodiments, the method of the present disclosure described above can include wherein performing the exposure process comprises avoiding exposing the at least one biosubstance to more than approximately 45 Joules of ultraviolet light energy.

In embodiments, the method of the present disclosure described above can include wherein performing the exposure process includes: disposing a photomask at least proximate to the backing structure, the photomask having a set of openings therein, the set of openings corresponding to a set of microneedle cross-sectional areas; and directing electromagnetic energy through each of the set of openings, portions of the backing structure, and portions of the microneedle forming biocompatible polymer layer.

In embodiments, the method of the present disclosure described above can include wherein the backing structure comprises at least one of a support member and a biocompatible polymer backing layer.

In embodiments, the method of the present disclosure described above can include wherein the backing structure excludes a biocompatible polymer backing layer.

In embodiments, the method of the present disclosure described above can include wherein the microneedle forming biocompatible polymer comprises a poly(ethylene) glycol (PEG) based polymer.

In embodiments, the method of the present disclosure described above can include wherein the biocompatible polymer backing layer comprises a poly(ethylene) glycol (PEG) based polymer.

In embodiments, the method of the present disclosure described above can include wherein contacting a microneedle forming biocompatible polymer with a surface of the backing structure comprises: providing a chamber having a set of interior surfaces, at least one interior surface of the set of interior surfaces comprising the surface of the backing structure intended for contacting the microneedle forming biocompatible polymer; and introducing the microneedle forming biocompatible polymer into the chamber.

In embodiments, the method of the present disclosure described above can include wherein contacting a microneedle forming biocompatible polymer with a surface of the backing structure further comprises establishing a chamber depth corresponding to an intended length of microneedles within the set of microneedles.

In embodiments, the method of the present disclosure described above can include wherein performing the exposure process comprises selectively directing electromagnetic energy into the chamber.

In embodiments, the method of the present disclosure described above can include wherein providing a backing structure comprises: providing a support member; providing a chamber having a set of interior surfaces, at least one interior surface within the set of interior surfaces comprising a surface of the support member; introducing at least one biocompatible polymer into the chamber; contacting the at least one biocompatible polymer with the surface of the support member corresponding to an interior surface of the set of interior surfaces, thereby forming a biocompatible polymer layer carried by the surface of the support member; and directing electromagnetic energy into the chamber for crosslinking portions of the at least one biocompatible polymer layer to thereby form a biocompatible backing layer carried by the surface of the support member.

A second aspect of the present disclosure provides an apparatus for fabricating a microneedle device that can include: a chamber comprising: a chamber body having a set of interior surfaces; a backing structure receiving portion configured to carry a backing structure such that a surface of the backing structure forms an interior surface within the set of interior surfaces; and a chamber opening configured for introducing a biocompatible polymer into the chamber.

In embodiments, the apparatus of the present disclosure described above can include a chamber depth adjustment mechanism configured for selectively establishing a chamber depth corresponding to a microneedle length.

In embodiments, the apparatus of the present disclosure described above can include an ultraviolet light curing station configured for directing ultraviolet light through the surface of the backing structure that forms an interior surface within the set of interior surfaces of the chamber.

In embodiments, the apparatus of the present disclosure described above can include wherein the chamber comprises at least one set of openings configured for fluid communication of a rinsing medium therethrough.

A third aspect of the present disclosure provides a microneedle device that can include: a set of microneedles comprising crosslinked regions of a microneedle forming biocompatible polymer, the microneedle forming biocompatible polymer configured for crosslinking in response to electromagnetic energy exhibiting a set of crosslinking wavelengths; and a backing structure carrying the set of microneedles, the backing structure at least partially transmissive with respect to the set of crosslinking wavelengths, wherein at least one of the set of microneedles and the backing structure carries at least one biosubstance, and wherein the microneedle forming biocompatible polymer is water soluble when non-crosslinked.

In embodiments, the microneedle device of the present disclosure described above can include wherein the backing structure comprises at least one of a support member and a biocompatible polymer layer.

In embodiments, the microneedle device of the present disclosure described above can include wherein at least one of the microneedle forming biocompatible polymer and the backing structure comprises a poly(ethylene) glycol (PEG) based material.

A fourth aspect of the present disclosure provides a method for microneedle device fabrication that can include: providing a first backing structure having a front surface and a back surface; contacting at least one microneedle forming biocompatible polymer with the front surface of the first backing structure to form a microneedle forming biocompatible polymer layer on the front surface of the first backing structure, the microneedle forming biocompatible polymer layer having a thickness, the microneedle forming biocompatible polymer layer chemically coupleable to the front surface of the first backing structure; and performing an exposure process comprising selectively directing electromagnetic energy into portions of each of the first backing structure and the biocompatible polymer layer to form a set of microneedles within the biocompatible polymer layer, wherein the set of microneedles are chemically coupled to the front surface of the first backing structure; providing a second backing structure; and combining the first backing structure having microneedles chemically coupled to the front surface of the first backing structure with the second backing structure, wherein the second backing structure is chemically coupled to the back surface of the first backing structure via a prepolymer solution; wherein the set of microneedles comprises crosslinked biocompatible polymer material suitable for penetration into skin in the substantial absence of additional fabrication processes directed to forming the set of microneedles other than removal of non-crosslinked biocompatible polymer material from the set of microneedles.

A fifth aspect of the present disclosure provides a microneedle device that can include a set of microneedles comprising crosslinked regions of a microneedle forming biocompatible polymer, the microneedle forming biocompatible polymer configured for crosslinking in response to electromagnetic energy exhibiting a set of crosslinking wavelengths; and a first backing structure having a front surface and a back surface, the first backing structure carrying the set of microneedles on the front surface of the first backing structure, the first backing structure at least partially transmissive with respect to the set of crosslinking wavelengths; and a second backing structure carrying the first backing structure carrying the set of microneedles, the second backing structure chemically coupled to the back surface of the first backing structure via a prepolymer solution; wherein at least one of the set of microneedles, the first backing structure and the second backing structure carries at least one biosubstance, and wherein the microneedle forming biocompatible polymer is water soluble when non-crosslinked.

A sixth aspect of the present disclosure provides a method for fabricating microneedles that can include: providing a glass photomask with microlenses etched in the glass photomask; contacting at least one microneedle forming biocompatible polymer with a surface of the glass photomask to form a microneedle forming biocompatible polymer layer on the surface of the glass photomask, the microneedle forming biocompatible polymer layer having a thickness, the microneedle forming biocompatible polymer layer chemically coupleable to the glass photomask; and performing an exposure process comprising selectively directing electromagnetic energy into portions of each of the glass photomask and the biocompatible polymer layer to form a set of microneedles within the biocompatible polymer layer, wherein the set of microneedles comprises crosslinked biocompatible polymer material suitable for penetration into skin in the substantial absence of additional fabrication processes directed to forming the set of microneedles other than removal of non-crosslinked biocompatible polymer material from the set of microneedles.

In embodiments, the method for fabricating microneedles of the present disclosure described above can include wherein the photomask having the set of microneedles chemically coupled thereto is partially submerged in a well containing a prepolymer solution, wherein a portion of the set of microneedles is submerged in the prepolymer solution, and wherein the prepolymer solution surrounds the submerged portion of the microneedles to form a backing layer.

BRIEF DESCRIPTION OF THE DRAWINGS

Embodiments of the present disclosure are described herein with reference to the drawings in which:

FIGS. 3A-3D show a drug incorporation in microneedles arrays in accordance with a representative embodiment of the present disclosure: (A) Without Rhodamine B; (B) Rhodamine B in microneedle shafts; (C) Rhodamine B in backing layer; (D) Rhodamine B in both microneedle shafts and backing (Bar 100 microns) in accordance with an embodiment of the present disclosure.

FIGS. 6A-6H show an effect of increasing number of spacers (A-F). Images at various (2-7 coverslips) spacers, with microneedle length of 252, 441, 680, 820, 1044 and 1211 µm, respectively; (G) Increase in microneedle length with increase in spacers; and (H) Decrease in the tip diameter with increase in spacers in accordance with an embodiment of the present disclosure.

FIGS. 7A-7D show a penetration of microneedles in cadaver pig skin: (A) Area of microneedle penetration stained with trypan blue; (B) A positive control with skin penetrated using a 27 gauge hypodermic needle (4×3 array) and holes stained by trypan blue; (C) Negative control (no microneedles) applied on the skin, subsequently stained by trypan blue; (D) Histological section of skin stained with hematoxylin and eosin post microneedle application in accordance with an embodiment of the present disclosure.

FIGS. 8A-8B show a release profile of rhodamine B encapsulated in microneedles over a period of 1 week (A) percentage amount released did not vary significantly amongst different encapsulation concentrations and (B) cumulative amount released in accordance with an embodiment of the present disclosure.

FIG. 9 shows a cumulative amount of rhodamine B permeated through the rat skin when applied with a microneedle patch or a propylene glycol solution of rhodamine B over a period of 48 hours in accordance with an embodiment of the present disclosure.

FIGS. 14A-14B shows a release profile of BSA encapsulated in microneedles over a period of 6 hours (A) percentage amount released and (B) cumulative amount released in accordance with an embodiment of the present disclosure.

FIGS. 15A-15B show an increase in a cumulative amount of bovine serum albumin (BSA) permeated per unit area through rat skin as a result of an application of a microneedle device in accordance with an embodiment of the present disclosure, as compared to propylene glycol solution of BSA.

FIGS. 16A-16C show an in vitro biocompatibility testing using: (A) Human Dermal Fibroblasts (HDF) cells; (B) HaCaT cells; and (C) Human Embryonic Kidney 293 (HEK293) cells demonstrated high cell viabilities indicating the biocompatibility of PEGDA microneedles in accordance with an embodiment of the present disclosure.

FIGS. 16D-16F are graphs illustrating that the in vitro cytotoxicity testing using lactate dehydrogenase assay with (D) human dermal fibroblasts (HDF), (B) human adult low calcium high temperature (HaCaT) cells, and (C) human embryonic kidney 293 (HEK293) cells demonstrated low toxicity, indicating the biocompatibility of PEGDA microneedles in accordance with an embodiment of the present disclosure.

FIGS. 17A-17D are a schematic illustration of a process for fabricating a microneedle-integrated thick patch device in accordance with an embodiment of the present disclosure: (A) Fabrication of a thin backing layer on a TMSPMA coated coverslip; (B) Fabrication of microneedles using high intensity ultra violet light irradiation; (C) Fabrication of a thick backing layer patch using low intensity ultra violet light irradiation; and (D) Final step of combining the microneedles on the thin backing layer with the thick backing layer patch.

FIGS. 18A-18B show images of microneedle arrays formed during fabrication of microneedle integrated thick patch devices of the present disclosure in accordance with an embodiment of the present disclosure, wherein the images were acquired using a Nikon AZ100 Multipurpose Zoom Microscope: (A) Plain microneedle array without rhodamine B and (B) Microneedle array with rhodamine B encapsulated in all layers.

FIGS. 18C-18F show images of microneedle arrays of microneedle integrated thick patch devices after the exertion of different forces using a skin model in accordance with an embodiment of the present disclosure, wherein the images demonstrate that the sharpness of the microneedles was maintained, and wherein the images were acquired using a Nikon AZ100 Multipurpose Zoom Microscope: (C) Exertion of force of 10 N; (D) Exertion of force of 30 N; (E) Exertion of force of 50 N; and (F) Exertion of force of 70N.

FIG. 18G is a graph illustrating the length of microneedles after varying forces were applied on and to the microneedle array in accordance with an embodiment of the present disclosure.

FIGS. 19A-19D are images showing the penetration of microneedles in rat skin by exerting varying amounts of force on the skin in accordance with an embodiment of the present disclosure: (A) Exertion of a force of 10N; (B) Exertion of a force of 30N; (C) Exertion of a force of 50N; and (D) Exertion of a force of 70N.

FIG. 19E is a graph illustrating the number and percentage of microneedles that have penetrated the skin based on the force applied or exerted as shown by trypan blue staining in accordance with an embodiment of the present disclosure.

FIGS. 20A-20B are graphs showing results from in vitro release testing of a lidocaine encapsulated microneedle-integrated thick patch device in accordance with an embodiment of the present disclosure: (A) In vitro release of lidocaine over 24 hours (B) In vitro release of lidocaine over the first two hours. The cumulative amount of lidocaine released increases as encapsulation concentration of lidocaine increases.

FIGS. 20C-20D are graphs illustrating the permeation of lidocaine from a microneedle-integrated thick patch device through rat skin in accordance with an embodiment of the present disclosure: (C) Permeation over 24 hours (D) Permeation over the first two hours. The amount of lidocaine permeated from a 21% lidocaine microneedle-integrated thick patch of the present disclosure was higher than that of Lignopad®, a commercial patch, in accordance with an embodiment of the present disclosure. Higher initial rates of permeation of lidocaine were observed for the 21% lidocaine microneedle-integrated thick patch in accordance with an embodiment of the present disclosure.

FIGS. 22A-22C are a schematic illustration of a process for fabricating sharp or sharper microneedles in accordance with an embodiment of the present disclosure, wherein the sharp or sharper microneedles can be used for efficient transdermal bioactive substance (i.e., a drug(s) and/or a protein(s)) delivery in accordance with an embodiment of the present disclosure. FIG. 21(A) is a schematic illustration of a fabrication process of a photomask having lenses or microlenses embedded therein in accordance with an embodiment of the present disclosure: (1) 4" glass wafer; (2) Cr/Au layer deposited using an e-beam evaporator; (3) Exposure of a Cr/Au/photoresist masking layer to UV light with a photomask; (4) Formation of pattern on layer using a Cr/Au etchant; (5) Temporary bonding of glass on a dummy silicon wafer; (6)-(7) Wet etching (isotropic) process using HF/HCl etchants followed by ultrasonication; and (8) Debonding of dummy silicon wafer and removal of photoresist layer. FIG. 21(B) is a schematic illustration of a fabrication process of sharp or sharper microneedles in accordance with a an embodiment of the present disclosure: a chromium coated photomask (9×9 array) with microlenses embedded therein, prepared by a fabrication process as shown in FIG. 21(A), is placed over a cavity containing pre-polymer solution and exposed to UV irradiation. FIG. 21(C) is a schematic illustration of a fabrication process of a backing layer in accordance with an embodiment of the present disclosure: the photomask with microlenses embedded therein and with sharp or sharper microneedles attached to the photomask, prepared by a fabrication process as shown in FIG. 21(B), is placed in a well filled with a pre-polymer solution and exposed to UV irradiation.

FIGS. 23A-23D are images illustrating the characterization of a photomask having microlenses embedded or etched therein in accordance with an embodiment of the present disclosure: (A) UV (365 nm) exposure focuses light into a conical path, producing tapered microneedles; (B) A SEM image of a portion of an array of microlenses etched into a glass substrate; (C) A SEM image of a microlens; and (D) A portion of an array of PDMS mold replicas copied from the microlenses, showing the flattened convex surface, under a stereomicroscope.

FIGS. 24A-24D are graphs illustrating the effect of UV parameters on the geometry of microneedles in accordance with an embodiment of the present disclosure. FIGS. 23A-23B illustrate the effect of (A) intensity and (C) spacer thickness on the length of microneedles in accordance with an embodiment of the present disclosure. FIGS. 23C-23D illustrate the effect of (B) intensity and (D) spacer thickness on the tip diameter of microneedles in accordance with an embodiment of the present disclosure.

FIGS. 25A-25C are images of microneedle arrays illustrating the effect of varying the pre-polymer volume used for fabrication of the backing layer in accordance with an embodiment of the present disclosure: (A-C) Images of microneedle arrays at various pre-polymer volumes, for example, 300 µl, 400 µl and 550 µl with a resulting average microneedle length of 1224, 813 and 583 respectively.

FIGS. 25D-25F are images of microneedle arrays, corresponding to FIGS. 24A-24C, after fracture force testing.

FIGS. 25G-25I are graphs illustrating: (G) Decrease in microneedle length with an increase in pre-polymer volume in accordance with an embodiment of the present disclosure; (H) Decrease in microneedle base diameter with an increase in pre-polymer volume in accordance with an embodiment of the present disclosure; and (I) Indifferent or comparable microneedle fracture force across the three different pre-polymer volumes in accordance with an embodiment of the present disclosure.

FIGS. 26A-26D are images showing the penetration of microneedles in rat abdominal skin in accordance with an embodiment of the present disclosure as shown by trypan blue staining: (A-C) penetration by microneedles of average length 1224, 813 and 583 µm respectively, with the force of a thumb; and (D) Negative control (no microneedle treatment) stained by trypan blue.

FIGS. 26E-26F are graphs illustrating: (E) Number of successfully penetrated microneedles of average length 1224, 813 and 583 µm in accordance with an embodiment of the present disclosure; and (F) Percentage of penetration by microneedles of average length 1224, 813 and 583 µm in accordance with an embodiment of the present disclosure.

FIGS. 27A-27D are images illustrating enhanced collagen permeation through microneedle pretreated skin in accordance with an embodiment of the present disclosure: (A) Auto-fluorescence of cadaver rat skin; and (B-D) Fluorescence of bovine collagen type 1, FITC conjugate together with auto-fluorescence of rat skin for collagen concentrations 0.025, 0.05 and 0.075% w/v respectively.

DETAILED DESCRIPTION

Figure 1A:
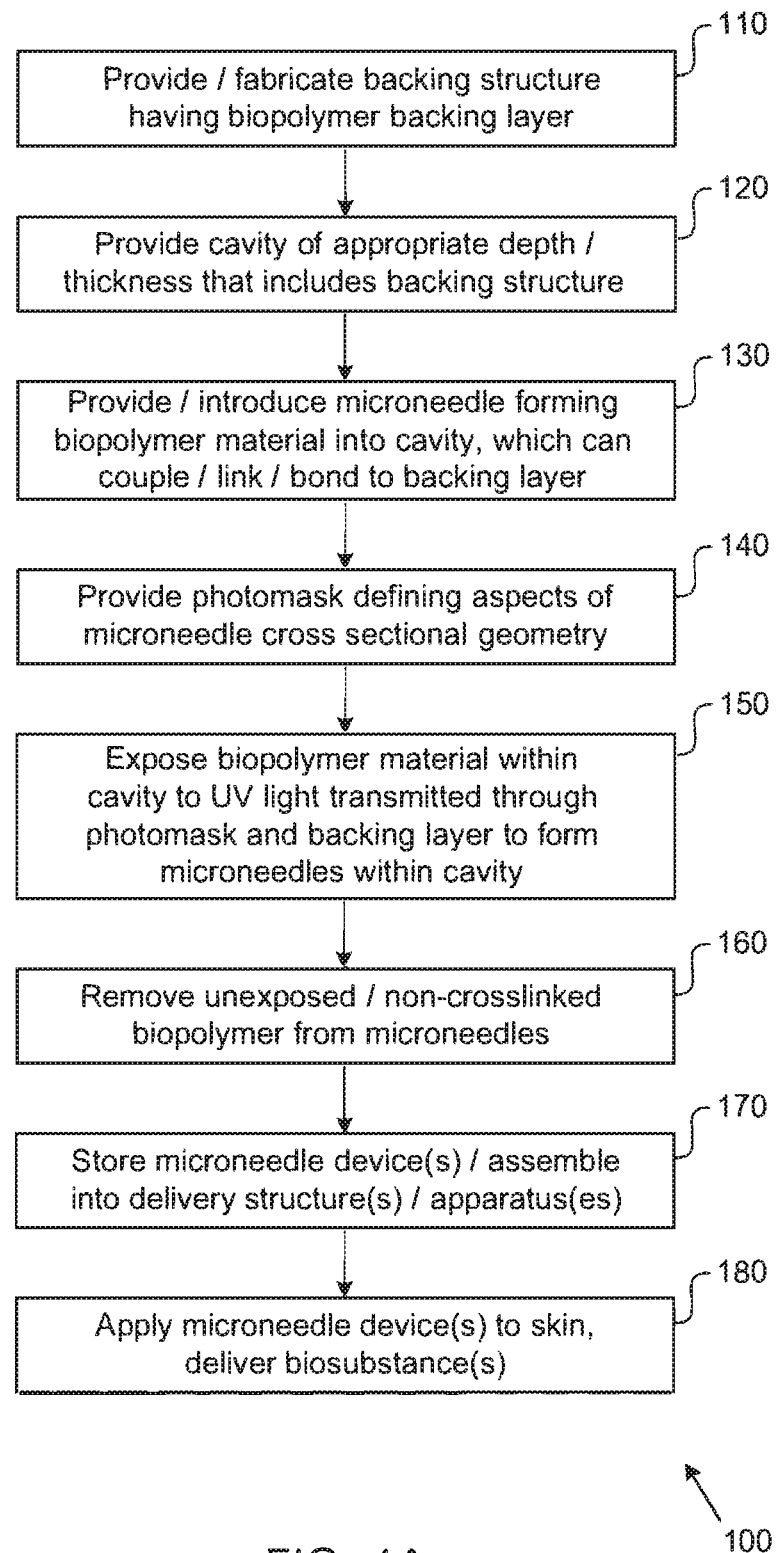
FIG. 1A is a flow diagram of a representative microneedle device fabrication process in accordance with an embodiment of the present disclosure.

In the following detailed description, reference is made to the accompanying figures/drawings, which form a part hereof. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein.

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. Additionally, the recitation of a particular numerical value or value range is understood to be the recitation of an approximate numerical value or value range, respectively.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a process, a physical parameter, or a value depending upon the type of set under consideration.

Unless specified otherwise, the terms "comprising" and "comprise" as used herein, and grammatical variants thereof, are intended to represent "open" or "inclusive" language such that they include recited elements but also permit inclusion of additional, un-recited elements.

As used herein, the term "about", in the context of measurement values, conditions, concentrations of components, etc., means +/−5% of the stated value, or +/−4% of the stated value, or +/−3% of the stated value, or +/−2% of the stated value, or +/−1% of the stated value, or +/−0.5% of the stated value, or +/−0% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Various embodiments in accordance with the present disclosure are directed to microneedle apparatuses, structures, or devices that include a biocompatible polymer material, substance, or composition (hereafter "biopolymer"); and systems, apparatuses, and techniques for fabricating microneedle devices by way of procedurally straightforward, cost-efficient, and biocompatible, essentially biocompatible, or substantially biocompatible fabrication processes. Such fabrication processes avoid the exposure or significant exposure of one or more biosubstances, biocompounds, biocompositions, or biomolecules (e.g., one or more drugs, proteins, amino acids, growth factors, vaccines, or other bioactive or biotherapeutic substances, compounds, compositions, or molecules) carried by a biopolymer to an environment, processing condition, and/or processing agent, species, or substance that can significantly adversely affect, alter, or degrade the structural and functional characteristics, properties, or integrity of the bioactive/biotherapeutic substance(s), thereby substantially preserving or maximizing the structural and functional integrity of such bioactive/biotherapeutic substance(s) and/or the extent to which such bioactive/biotherapeutic substance(s) remain viable when carried by a microneedle device.

Microneedle device fabrication processes in accordance with the present disclosure avoid exposing a biopolymer and a set of biosubstances carried thereby to processing environments/equipment/conditions/energies, reactive species, and/or chemical substances/species associated with conventional micron scale manufacturing or fabrication processes which would present a significant likelihood or risk of adversely affecting biosubstance integrity or viability. Multiple embodiments in accordance with the present disclosure avoid exposing one or more biosubstances carried by a biopolymer to unnecessarily or undesirably high temperature(s) (e.g., at which significant protein denaturation is expected to occur), for instance, temperatures significantly exceeding room temperature, such as temperatures above approximately 40° C., temperatures above approximately 30° C., or temperatures above or significantly above room temperature such as a temperature beyond approximately 27° C.). Thus, during a microneedle fabrication procedure or process, several embodiments in accordance with the present disclosure maintain or generally maintain one or more biosubstances carried by a biopolymer below a biosubstance degradation threshold temperature at which significant biosubstance degradation is likely or expected to occur (e.g., such a threshold temperature can be defined as approximately 40° C., 30° C., or a temperature above or significantly above room temperature such as 27° C.). A given biosubstance degradation threshold temperature can be determined based upon one or more types of biosubstances under consideration, in a manner readily understood by one of ordinary skill in the relevant art. Embodiments in accordance with the present disclosure can therefore avoid conventional micron scale fabrication procedures such as soft bakes and hard bakes that can adversely affect biosubstance integrity or viability (e.g., in several embodiments, soft bakes and hard bakes can be entirely avoided or excluded).

Embodiments in accordance with the present disclosure can further substantially or entirely avoid exposing such biosubstances to potentially damaging reactive species conventionally encountered in micron scale fabrication processes, such as plasma species; and chemical substances conventionally encountered in micron scale fabrication processes, such as organic solvents (e.g., Carbon chain/Carbon based solvents) or photoresist developers. In accordance with a number of microneedle device fabrication processes in accordance with the present disclosure, solvents other than water are avoided, at least substantially excluded, excluded, or unnecessary.

In addition to the foregoing, microneedle device fabrication processes in accordance with various embodiments of the present disclosure reduce or minimize the number, types, complexity, and/or cost of equipment needed for fabricating microneedle devices. For instance, microneedle device fabrication processes in accordance with embodiments of the present disclosure can eliminate the need for particular types of conventional micron scale fabrication equipment, such as spin coaters or wet/dry etching equipment. Microneedle device fabrication processes in accordance with embodiments of the present disclosure can further minimize or avoid/eliminate the need for cleanroom facilities. Various embodiments of microneedle device fabrication processes involve straightforward photolithographic techniques, requiring equipment such as a UV light source(s) associated with a biopolymer curing station.

Moreover, microneedle device fabrication processes in accordance with various embodiments of the present disclosure provide for the direct, essentially direct, or substantially direct fabrication of microneedles or microneedle arrays in a small or minimal number of steps in a manner that excludes, avoids, or eliminates the need for one or more molds, templates, stamps, or other intermediate structures commonly encountered in conventional microneedle fabrication processes. For instance, multiple microneedle device fabrication processes in accordance with the present disclosure provide for the direct fabrication of microneedles or a microneedle array in a unified or single step following the provision or fabrication of a backing structure such as described below. Consequently, various microneedle device fabrication processes in accordance with various embodiments of the present disclosure provide for microneedle array fabrication or formation in a mold-free, template-free, or stamp-free manner.

Aspects of a Representative Fabrication Process

FIG. 1(A) is a flow diagram of a representative microneedle device fabrication process 100 in accordance with an embodiment of the present disclosure. In an embodiment, the process 100 includes a first process portion 110 involving providing or fabricating a backing structure, which includes at least one of a biopolymer backing layer and a support member or structure such as a glass, quartz, plastic, surface treated hard material, or other type of substantially solid support or substrate. In a number of embodiments, the backing structure includes each of a biopolymer backing layer and a support member, where the support member can be configured for temporarily, essentially permanently, or permanently carrying the backing layer.

The biopolymer backing layer includes a set of biopolymers that is cross-linkable as a result of exposure to electromagnetic energy, such as a photosensitive biocompatible polymer. In various embodiments, the biopolymer backing layer includes at least one type of photo-crosslinkable biopolymer such as a (PEG) based biopolymer, for instance, an acrylated PEG polymer such as a PEG monoacrylate, diacrylate (PEGDA), methacrylate, methyl ether acrylate, and/or another biocompatible polymer. Depending upon embodiment details, the biopolymer backing layer can exclude or include one or more bioactive substances or compositions such as a set of drugs, proteins, and/or other substances, in a manner understood by one of ordinary skill in the relevant art.

The support member includes a first surface or side; a second surface or side; and a thickness defined between the first and second sides. In various embodiments, the support layer includes a planar or generally planar surface. One side of the support member, e.g., the support member's second side, which can be a planar or generally planar surface, is intended or configured for carrying the backing layer. The support member's second side includes or provides an interface that can form chemical bonds with the backing layer. In multiple embodiments, the support member and the backing layer can be chemically coupled, linked, or bound to each other, for instance, in association with or by way of a support member surface treatment such as a silanization treatment involving the application of a silanizing agent or silane-based chemical coupling agent such as 3-[tris(trimethylsilyloxy)silyl]propyl methacrylate (TMSPMA) to the support member's second side (e.g., in accordance with a silanization process, such as that described below).

Following an appropriate support member surface treatment, unexposed or non-crosslinked biopolymer material can be disposed upon or applied to the support member's second surface and exposed to UV light to form the backing layer. In accordance with multiple embodiments of the present disclosure, the support member is at least partially transmissive with respect to the wavelength(s) or wavelength range(s) of electromagnetic energy to which the set of biopolymers forming the backing layer is responsive to photo-crosslinking. In a number of embodiments, the support member is at least partially transmissive (e.g., significantly or very significantly transmissive) with respect to wavelengths of UV light that can photo-crosslink a biopolymer material used to form the backing layer.

In various embodiments, the application of electromagnetic energy such as UV light to the biopolymer material used to form the backing layer is performed in a manner that reduces or avoids the likelihood of significantly degrading or adversely affecting the structural and/or functional properties of the bioactive substance(s) carried by the backing layer. For instance, the application of UV light to the biopolymer material used to form the backing layer can be regulated or controlled such that an instantaneous, average, or overall energy dose is maintained at or below a desired, target, or maximum level that could or would be expected to adversely affect the backing layer's bioactive substance(s). Regulation or control of an energy dose delivered to the biopolymer material that forms the backing layer can be accomplished by way of limiting an energy intensity, power, or amplitude, and/or limiting an energy delivery time.

As further detailed below, in several embodiments the backing structure, which includes the support member and the crosslinked biopolymer backing layer, is formed through the use of a first chamber or cavity apparatus or structure. More particularly, a first cavity structure can be provided, one side or surface of which includes or is formed from the support member. An inner surface of the first cavity structure can be formed from portions of the support member's second surface, which is intended to carry the backing layer. The first cavity structure exhibits or defines intended internal geometric dimensions or an intended internal geometric shape, which provides a cross-sectional area (e.g., a generally rectangular cross-sectional area) and a backing layer depth or thickness. Unexposed or non-crosslinked biopolymer material can be introduced into the first cavity structure in a manner that conforms or generally conforms to the first cavity structure's internal geometric shape. Such non-crosslinked biopolymer material can chemically couple or bond to the support member, for instance, by way of chemical bonds facilitated or enabled by the aforementioned support member surface treatment.

Following the introduction or delivery of unexposed or non-crosslinked biopolymer material into the cavity, UV light can be directed through the support member and into the unexposed biopolymer material within the first cavity structure, thereby crosslinking the biopolymer material within the first cavity structure and forming a solidified biopolymer backing layer that is carried by the support member. Thus, the backing layer can include a first surface that is coupled or chemically bonded to the second surface of the support member; and a second surface that can be exposed to further processing for purpose of fabricating microneedles extending or projecting therefrom, as further detailed below, for instance by way of including or providing an interface that can form chemical bonds with a microneedle forming biopolymer.

While the above description is directed to one manner of fabricating a backing structure, in other embodiments, the backing structure (i.e., the support member and the crosslinked biopolymer backing layer) can be fabricated in a different manner, for instance, by way of a different type of chamber structure, or another type of backing structure fabrication apparatus configuration.

The process 100 further includes a second process portion 120 that involves providing a second chamber or cavity apparatus or structure, such as a cavity apparatus or structure that is identical, substantially identical, or similar to that used for fabricating the backing structure. In a number of embodiments, the second cavity structure can include one or more portions of the first cavity structure itself. The second cavity structure is configured to carry or include the backing structure as a surface of the second cavity structure, such that the backing layer resides within a predetermined inner portion or volume of the second cavity structure (e.g., an upper portion, region, or segment of the second cavity structure).

The second cavity structure is further configured to provide a depth or thickness between (a) a backing layer surface, such as the second backing layer surface, which can be a planar or generally planar surface, which is exposed within the second cavity structure; and (b) an opposing or lower boundary, border, or surface of the second cavity structure, where this depth or thickness can correspond to, determine, or define a microneedle length. In several embodiments, this depth or thickness is selectable or adjustable (e.g., automatically, semi-automatically, or manually selectable/adjustable) in a manner that facilitates or enables the fabrication of microneedles having an intended length within a selectable or adjustable microneedle length range. For instance, the second cavity structure's depth can be adjusted by way of mechanical means (e.g., a stepper motor), pneumatic means, fluidic means, or insertion/removal of spacer elements. In other embodiments, the second cavity structure's depth, defined between the second backing layer surface and an opposing or lower interior surface of the second cavity structure, is predetermined or fixed.

A third process portion 130 involves providing, introducing, or delivering a microneedle forming biopolymer within the second cavity structure, such that the microneedle forming biopolymer can (a) couple or chemically bond to the backing layer by way of exposure to or interaction with the backing layer's exposed second surface; and (b) volumetrically occupy or substantially occupy the second cavity structure's internal geometry between the backing layer's second surface and the lower surface of the second cavity structure. The microneedle forming biopolymer material includes at least one type of biocompatible polymer, and in various embodiments, the microneedle forming biopolymer is identical, essentially identical, or substantially identical, similar, or generally similar to the biopolymer from which the backing layer is formed. Thus, in several embodiments the microneedle forming biopolymer includes a PEG based biopolymer, for instance, an acrylated PEG polymer such as PEG monoacrylate, diacrylate (PEGDA), methacrylate, methyl ether acrylate, and/or another biocompatible polymer. Depending upon embodiment details, the microneedle forming biopolymer material can include or exclude one or more bioactive substances or compositions such as a set of drugs, proteins, and/or other substances.

A fourth process portion 140 involves providing or disposing a photomask adjacent or proximate to or upon the backing structure. More particularly, in various embodiments, the photomask is disposed adjacent to or upon the first surface of the support member, which remains external to the second cavity structure's interior in which the microneedle forming biopolymer resides. The photomask selectively defines patterned areas, regions, or openings corresponding to intended microneedle cross-sectional areas, through which UV light can propagate, as further detailed below. In embodiments, the shape, length and tip diameter of microneedles can be modified by modifying the photomask to be used.

A fifth process portion 150 involves directing UV light (a) toward or to the photomask; (b) through the selectively patterned photomask openings; (c) through portions of the support member; (d) through the backing layer; and (e) into portions of the microneedle forming biopolymer layer corresponding to the selectively patterned photomask openings, thereby selectively cross-linking portions of the microneedle forming biopolymer layer and forming microneedles (e.g., a microneedle array in which individual microneedles are spatially organized or distributed in accordance with the spatial distribution of photomask openings) within the microneedle forming biopolymer layer. Thus, selective cross-linking of particular portions of the microneedle-forming polymer material, and hence the formation of microneedles, occurs by way of electromagnetic energy (e.g, UV light) traveling through particular spatially corresponding or aligned portions or regions of each of photomask openings, the backing layer, and the microneedle-forming polymer layer. Such microneedles have a length that corresponds to or is determined or defined by the aforementioned depth (e.g., a fixed or an adjustable depth) of the second cavity structure between the exposed second surface of the backing layer within the second cavity structure and the opposing or lower border, boundary, or surface of the second cavity structure's interior. More particularly, relative to the backing layer, a spatial distance between the proximal end(s) or base(s) of the microneedle(s) originating at the second surface of the backing layer and the distal end(s) or tip(s) of the microneedle(s) corresponds to or is determined or defined by the depth of the second cavity structure.

In accordance with multiple embodiments of the present disclosure, the microneedles, comprising crosslinked regions of the microneedle forming biopolymer material formed as a result of UV light propagation through the photomask openings, those portions of the support member beneath such photomask openings, portions of the backing layer beneath the support member and such photomask openings, and into the microneedle forming biopolymer material, are formed in a unified or single process portion or step involving one or more UV light exposure events (e.g., multiple time-segregated UV light exposure events, or a single UV light exposure event). In view of the foregoing, the cross-linked backing layer is at least partially transmissive, or substantially transmissive, to the UV light used to cross-link the microneedle-forming backing layer.

In various embodiments, the application of electromagnetic energy such as UV light to the microneedle forming biopolymer is performed in a manner that reduces or avoids the likelihood of significantly degrading or adversely affecting the structural and/or functional properties of a set of bioactive substances carried by each of (a) the backing layer; and (b) the microneedle forming biopolymer layer. For instance, the application of UV light through the backing layer and into the microneedle forming biopolymer can be regulated or controlled such that an instantaneous, average, or overall energy dose is maintained at or below a desired, target, or maximum level that could or would be expected to adversely affect the bioactive substance(s) carried by the backing layer and/or the microneedle forming biopolymer. Regulation or control of an energy dose delivered to the backing layer and/or the microneedle forming biopolymer material can be accomplished by way of limiting an energy intensity, power, or amplitude, and/or limiting an energy delivery time.

A sixth process portion 160 involves removing unexposed/non-crosslinked biopolymer surrounding the microneedles formed by way of directing UV light through the photomask, through portions of the support member beneath the photomask, through the backing layer, and into the microneedle forming biopolymer material. In various embodiments, the sixth process portion 160 involves a rinsing procedure, in which unexposed/non-crosslinked biopolymer material surrounding the microneedles is rinsed or washed away from the microneedles. The rinsing procedure can involve, for instance, one or more rinses with a rinsing medium (e.g., where the rinsing medium includes or is water), and in multiple embodiments can further exclude or avoid the use of solvents or chemical substances other than water. Depending upon embodiment details, the rinsing procedure can involve passing a rinsing medium into and through the second cavity structure (e.g., by way of a set of openings, passages, and/or channels corresponding to the second cavity structure); and/or removing the backing structure—crosslinked microneedle unit(s) (i.e., at least one backing structure carrying a set of crosslinked microneedles) from the second cavity structure, and exposing the backing structure—crosslinked microneedle unit to a rinsing medium external to the second cavity structure.

A seventh process portion 170 can involve further processing, handling, and/or storing one or more microneedle devices or arrays of microneedle devices formed by way of the first through sixth process portions 110-160. In some embodiments, the seventh process portion 170 can involve removal of the backing layer and the microneedles carried thereby from the support member, while in other embodiments the support member/backing layer/microneedles can be retained or maintained as an integral unit. Thus, any given microneedle device includes at least backing layer, which carries microneedles or a microneedle array extending therefrom. A microneedle device can further include the support member.

An eighth process portion 180 can involve applying one or more microneedle devices to a subject's skin (e.g., human or animal skin), such that microneedles penetrate into the skin, for instance, target locations, sites, or anatomical structures of the skin. Bioactive substances or compositions carried by the backing layer and/or the microneedles can subsequently be released or diffuse into such target skin locations, sites, or structures, for instance, in one or more manners identical or analogous to that described in detail below. Because microneedle device fabrication processes in accordance with embodiments of the present disclosure preserve or maximize the structural and functional integrity and viability of bioactive substances, compounds, or compositions carried by a microneedle device's backing layer and/or microneedles, the microneedle devices fabricated in accordance with embodiments of the present disclosure can be expected to facilitate or provide more reliable, more predictable, and/or enhanced efficacy delivery of bioactive substances, compounds, or compositions into the skin when compared to prior types of microneedle devices.

In some embodiments, one or each of a backing structure biopolymer and a microneedle forming biopolymer layer can include a set of biocompatible, inert, biosorbable, or biodegradable materials, compositions, or structures. For instance, in specific embodiments, a microneedle forming biopolymer can include include both PEGDA and gelatin (e.g., which can form a biosubstance delivery matrix within the microneedles).

In certain embodiments, the backing structure can exclude a biocompatible polymer backing layer. More particularly, in certain embodiments the backing structure includes a support member such as one of more of a glass, quartz, plastic, or other hard material that can be surface treated such that (a) a support member surface can firmly couple or chemically bond directly to a layer of microneedle forming biopolymer carried by the support member surface; and (b) microneedles that are fabricated by way of selectively or preferentially cross-linking portions of the microneedle forming biopolymer layer remain firmly coupled or chemically bonded to the support member itself. Hence, in such embodiments, microneedles are not bonded to a biocompatible polymer backing layer carried by a support member, but rather are bonded to one or more surface treated portions of the solid member itself. Consequently, microneedle fabrication occurs by way of selectively directing electromagnetic energy through the support member and into portions of the microneedle forming biopolymer layer carried thereby (e.g., by way of directing UV light (a) toward, to, and through a set of openings in a photomask disposed adjacent or upon the support member; (b) through portions of the support member corresponding to such openings; and (c) into corresponding portions of the microneedle forming biopolymer layer carried by and bonded to the support member). Other embodiments can include a backing structure having a surface that includes (a) a first surface area or region that includes a biocompatible polymer backing layer; and (b) a second surface area or region that excludes a biocompatible polymer backing layer. Microneedles can be bonded to and fabricated on each such surface area in a manner that is identical, substantially identical, or analogous to that described above.

In embodiments, a microneedle array device of the present disclosure can have dimensions of 1 cm×1 cm or less, or 1.5 cm×1.5 cm or less. In embodiments, a microneedle array device of the present disclosure can have dimensions of 1 cm×1 cm or more, or 1.5 cm×1.5 cm or more. Other dimensions are also contemplated.

In embodiments, a microneedle device fabrication process of the present disclosure can be used to fabricate a large-size microneedle array with a uniform distribution of microneedles from biocompatible polymers thereby alleviating the need for multiple microneedle applications when treating large skin areas. In embodiments the large microneedle array with a uniform distribution of microneedles can be 2.0 cm×2.0 cm or more, 5 cm×5 cm or more, 10 cm×10 cm or more, 15 cm×15 cm or more, 20 cm×20 cm or more, or 25 cm×25 cm or more. Other dimensions are also contemplated. Using one large microneedle array device, rather than several smaller microneedle arrays, to treat a large skin area can result in lower overall treatment costs for patients or customers.

In embodiments, a microneedle device fabrication process of the present disclosure can be scaled up to fabricate microneedle arrays with larger areas. In embodiments, a microneedle device fabrication process of the present disclosure can be scaled up to fabricate microneedle arrays with larger areas by utilizing a larger ultra violet light exposure area, utilizing a larger photomask, and utilizing larger substrates. In embodiments, the uniformity and robustness of microneedles of the microneedle arrays with large areas can be controlled by optimizing the ultra violet parameters and geometrical dimensions of the photomask to be used during fabrication.

In embodiments, a microneedle device fabrication process of the present disclosure can be scaled up to fabricate large-size disposable microneedle arrays that can create multiple passages through skin for a larger number of bioactive substance (i.e., a drug(s) and/or protein(s)) candidates without re-use of the microneedles.

In embodiments, a microneedle device fabrication process of the present disclosure can be an industrial scale microneedle device fabrication process.

Aspects of Particular Representative Microneedle Devices/Microneedle Device Fabrication Processes Certain representative embodiments in accordance with the present disclosure are described in detail hereafter to aid understanding.

In a number of representative embodiments described herein, a fabrication sequence includes coating support members such as glass cover slips with TMSPMA solution; fabricating a microneedle backing layer by covalently linking at least one TMSPMA coated cover slip to methacrylate groups of PEGDA by way of free radical polymerization using UV irradiation, which forms a PEGDA backing layer for microneedles. The said backing layer can be, for instance, approximately 175 µm thick. The said PEGDA, containing 0.5% of HMP as photoinitiator, is used as the prepolymer solution. The fabrication sequence further includes fabrication of microneedles using glass slides as supports or spacers for controlling microneedle length, where the PEGDA backing is mounted onto PEGDA prepolymer solution filled enclosed cavity, using a pattered film/photo mask which is then irradiated with UV light. The UV light will only pass through the clear regions on the photomask and forms microneedles by way of a crosslinking process understood by one of ordinary skill in the relevant art. The control of microneedle length is achieved by adjusting or manipulating spacer thickness by increasing the number of cover slips stacked on the base glass slide.

The only major investment in the fabrication technique is a UV curing station as opposed to requirements of clean room facilities, etching and other complicated microfabrication procedures. Thus, in various embodiments, each portion of microneedle device fabrication can occur outside of a clean room environment such as a type of micron scale fabrication facility corresponding to the fabrication of semiconductor type devices or structures.

UV exposure in the technique is limited to only a few to several seconds, which is far less than other techniques utilizing longer exposure times for polymerization. Protein molecules and/or other bioactive substances can be very fragile, especially in presence of UV light, and hence require a process with minimum exposure time, exposure energy, and/or exposure dose to ensure maximum stability. Poly (ethylene glycol) has been used in various drug delivery applications, and hence is well suited for microneedle fabrication. The present disclosure therefore presents a process which is less complicated, less time consuming, and relatively inexpensive when compared to existing techniques, offering the scope for commercial scale fabrication of this novel and effective drug delivery system.

In accordance with another aspect of the present disclosure, the microneedles are fabricated to contain model drugs/proteins (i.e., Rhodamine B and Bovine Serum Albumin (BSA)), in the shafts of the microneedles or the backing layer or both.

Representative Microneedle Device Fabrication and Testing Experiments

Experiments were conducted to fabricate microneedles containing representative/model drug(s)/protein(s), Rhodamine B and Bovine Serum Albumin (BSA), and determine certain properties of the microneedles (e.g., geometric characteristics), in accordance with particular embodiments of the present disclosure:

Experiment 1: Representative Process for Fabricating Biocompatible Polymeric Microneedles Containing a Representative Bioactive Substance (e.g., a Drug Such as Rhodamine B)

In the experiment, microneedles were tested for their drug encapsulation efficiency by encapsulating model drug Rhodamine B in the microneedle shafts or the backing layer or both. The fabrication method is based on photolithography, involving exposure of the polymer to UV light through a patterned mask in a single step process. The technique offers the advantage of short exposure to UV light.

1.1. Experimental Procedures:

Materials

Poly (ethylene glycol) diacrylate [PEGDA ($M_n$ 258)], 2-hydroxy-2-methyl-propiophenone, (HMP), 3-(trimethoxysilyl) propyl methacrylate (TMSPMA) and trypan blue solution (0.4%) were purchased from Sigma-Aldrich (St. Louis, Mo.). Rhodamine B was purchased from Alfa Aesar (Lancaster, UK). All materials used were reagent grade and were used as received. Water purified using Millipore Direct-Q® (Molsheim, France) was used in the studies.

Coating of Glass Coverslips

Glass coverslips (Cell Path, Wales, UK, 160-190 micron thickness, 22×22 mm) were immersed in TMSPMA solution overnight for coating. The coverslips were then baked for 2 hours at 70° C.; the resultant chemical interaction is depicted in FIG. 1(B).

Fabrication of Microneedle Backing Layer

Figure 1B:
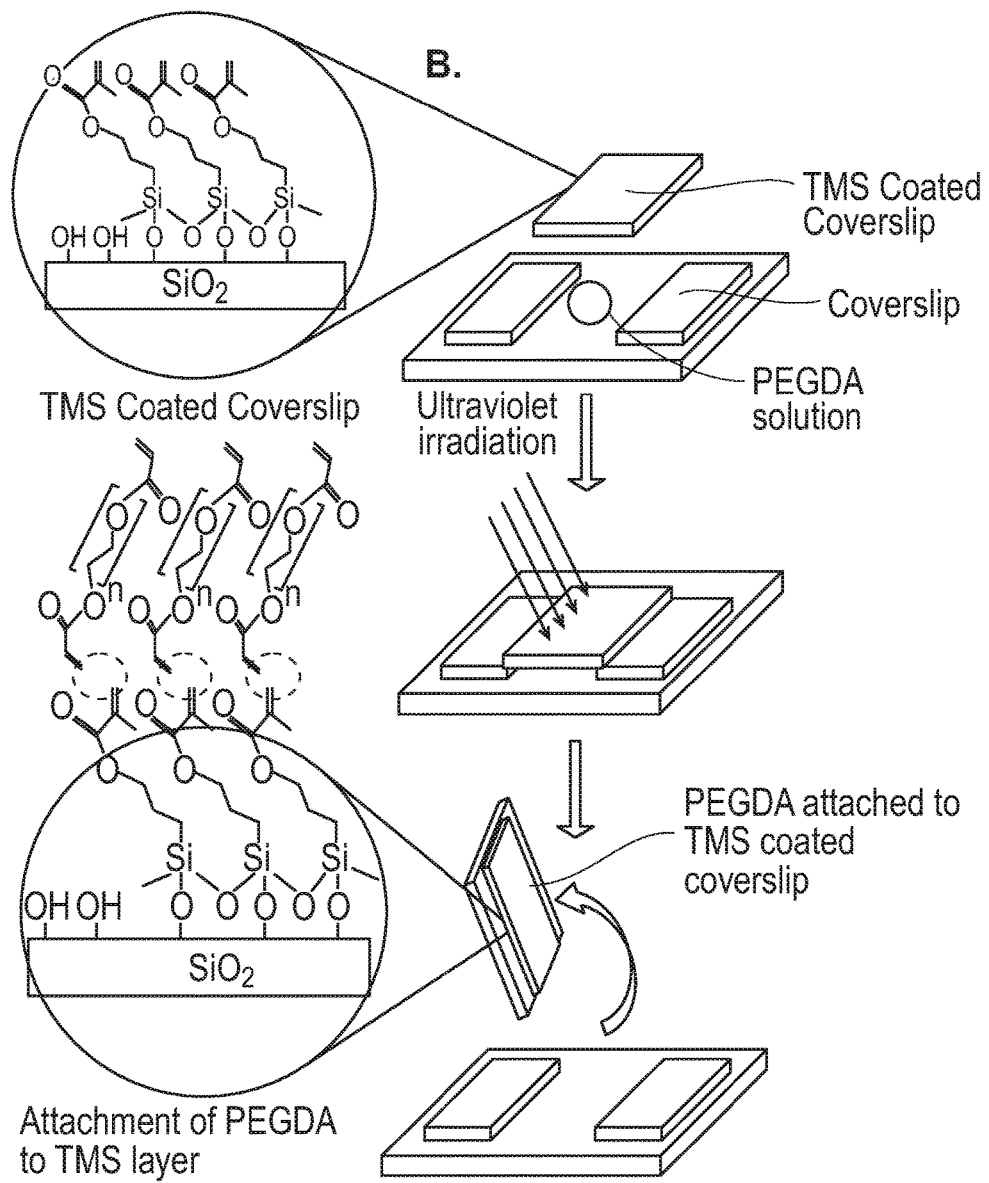
FIGS. 1B and 1C are a schematic illustration of a microneedle device fabrication process in accordance with an embodiment of the present disclosure: (B) Diagrammatic set up of fabrication process. PEGDA is attached to TMS coated coverslip via free radical polymerization using UV irradiation, forming the backing for microneedles. (C) Using glass slides as support, the PEGDA backing is mounted onto the set-up with PEDGA filled in the enclosed cavity. Subsequently, the set-up is irradiated with UV light. UV light is only able to pass through the clear regions on the photomask, forming microneedles in accordance with an embodiment of the present disclosure.

Two uncoated coverslips were supported on either side of a glass slide (Sail Brand, China) as shown in FIG. 1(B) to create cavity or chamber having a space approximately 175 µm deep or thick. The TMSPMA coated coverslip was then placed on/over this setup. PEGDA, containing 0.5% v/v of HMP (referred as the prepolymer solution) was wicked by capillary action into the gap between the coverslip and the glass slide (i.e., into the interior of the chamber). The setup was irradiated with high intensity ultra violet light of 12.4 W/cm$^2$ for 1 second using EXFO OmniCure® 5200-XL UV curing station (UV filter 320-500 nm) (EXFO, Photonic Solutions Inc., Canada). The intensity of the UV light was measured with the OmniCure® R2000 radiometer (EXFO, Photonic Solutions Inc., Canada). A collimating adaptor (EXFO 810-00042) was used with the UV light probe. TMSPMA molecules bonded to the glass coverslips are covalently linked to the methacrylate groups of PEGDA via free-radical polymerization (FIG. 1(B), within dashed ellipses). The backing layer, which was approximately 175 µm thick, was easily removed from the setup.

Fabrication of Microneedles

Figure 1C:
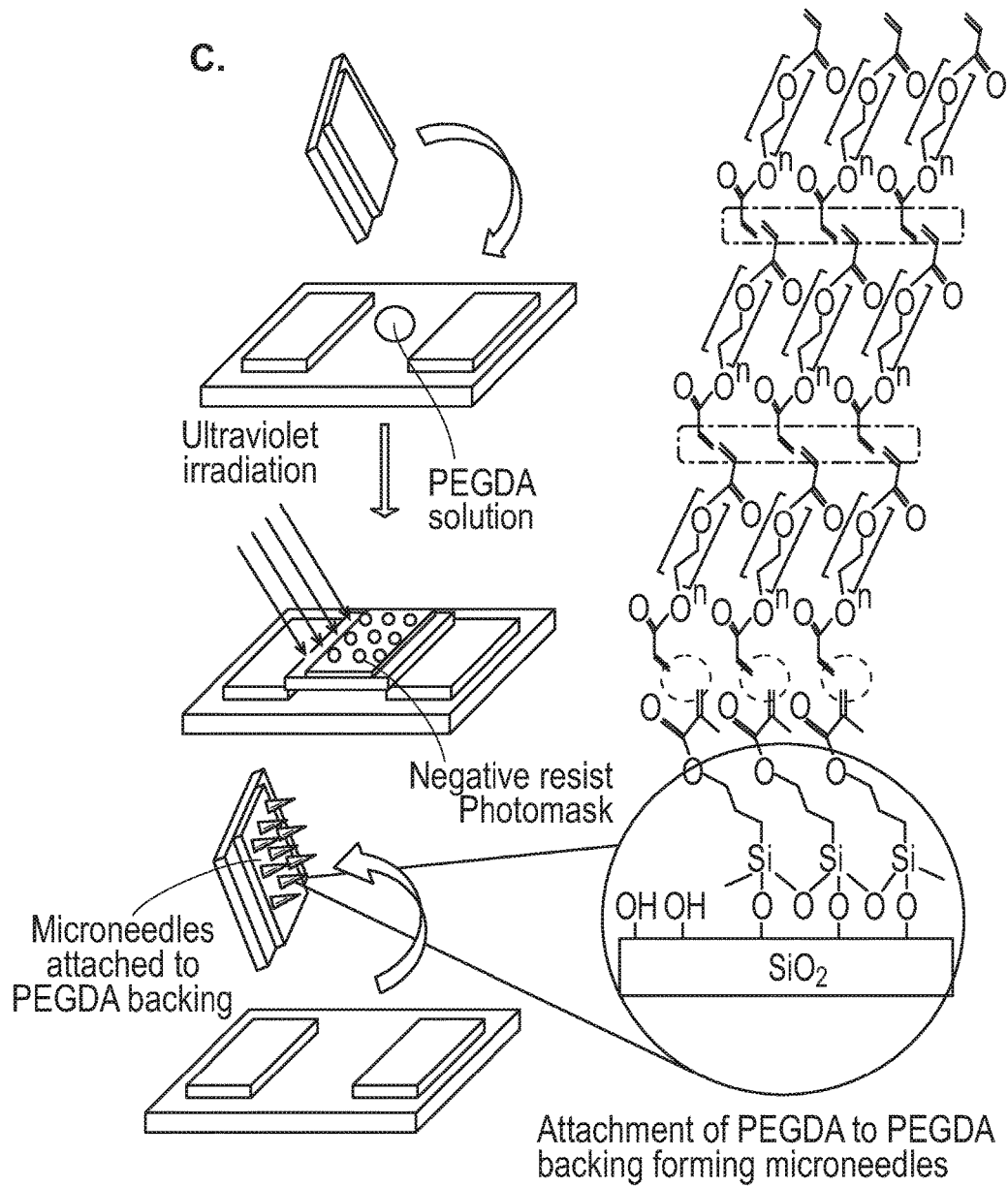
Figure 2:
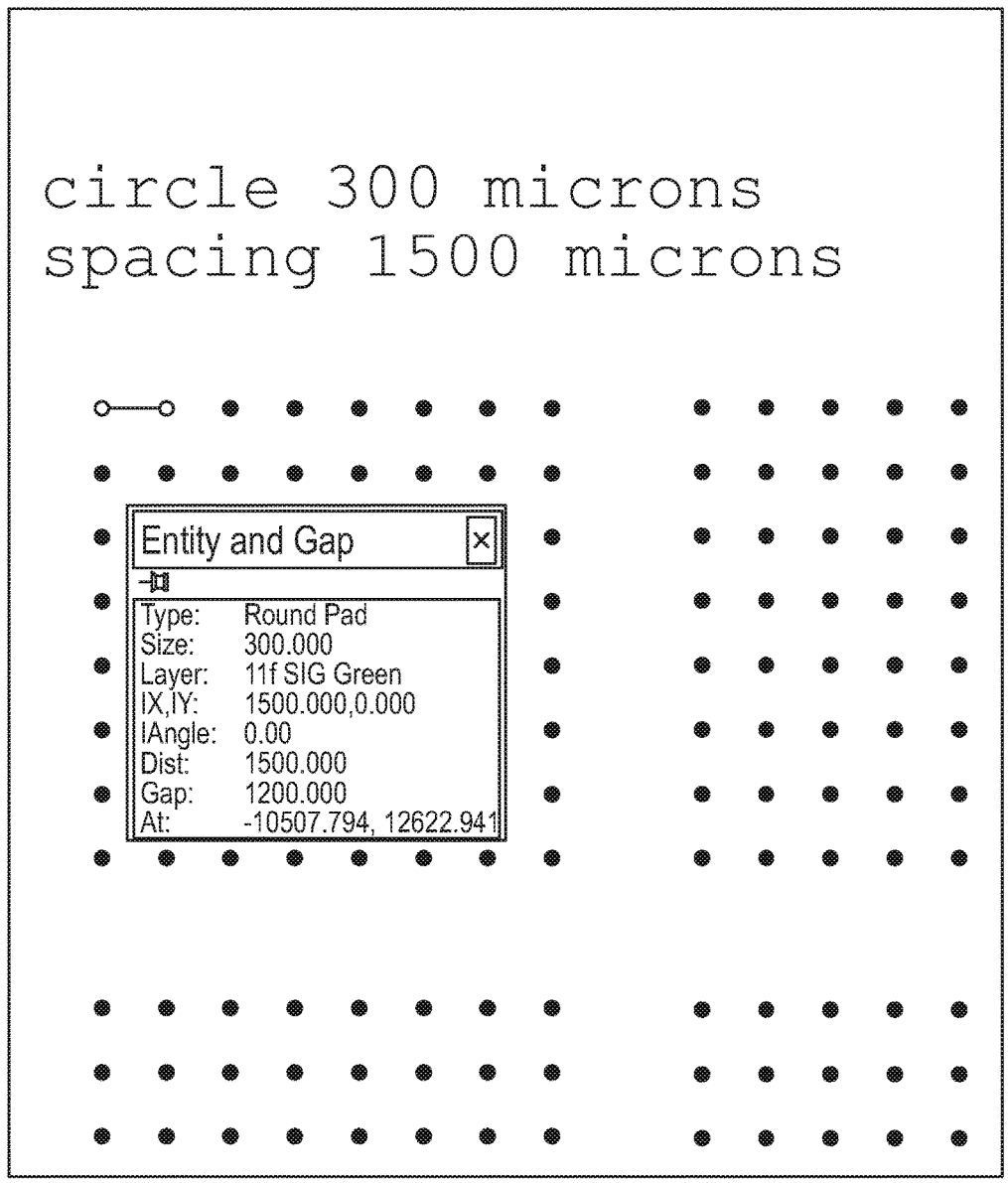
FIG. 2 is an illustration of Photomask template in accordance with an embodiment of present disclosure.

In a number of embodiments, the setup for fabrication of microneedles is analogous or similar to that for the microneedle backing except for the number of spacers. The number of spacers will govern the length of the microneedle(s) fabricated. Increasing spacer thickness was achieved by increasing the number of coverslips stacked on either side of the base glass slide as shown in FIG. 1(C). The prepolymer solution was then similarly wicked by capillary action into this gap as during the fabrication of backing layer. A plastic film was inked specifically in the pattern of microneedle array design. The background of the film was inked leaving small circles in an array pattern transparent to allow the UV light to pass through (Infinite Graphics Pte. Ltd., Singapore). This patterned film (also called a photomask, FIG. 2.) was designed to have various diameters of transparent circles in an array pattern, which govern the base diameter of the microneedles. Similarly, the center-to-center spacing between the two microneedles can be controlled. Such a film was placed on the fabrication setup which was subsequently irradiated with high intensity UV light. The use of the photomask blocked the UV access in the inked regions and allowed the UV light to pass through the transparent circles, which resulted in the formation of microneedle structures, thereby forming the microneedles, which covalently bonded with the PEGDA macromers in the backing layer to form an interpenetrating polymer network (IPN) (FIG. 1(C), within dashed rectangles). The microneedle structures, attached to the coverslip, were carefully removed from the base glass slide and washed with deionized water to remove the uncross-linked precursor solution. The prepared microneedles were then imaged using Nikon SMZ 1500 stereomicroscope (FIG. 3(A)). Microneedles were also tested for their drug encapsulation efficiency by encapsulating model drug rhodamine B, in the microneedle shafts (FIG. 3(B)) or the backing layer (FIG. 3(C)) or both (FIG. 3(D)).

Control of Microneedle Length

Figures 4A, 4B, 4C:
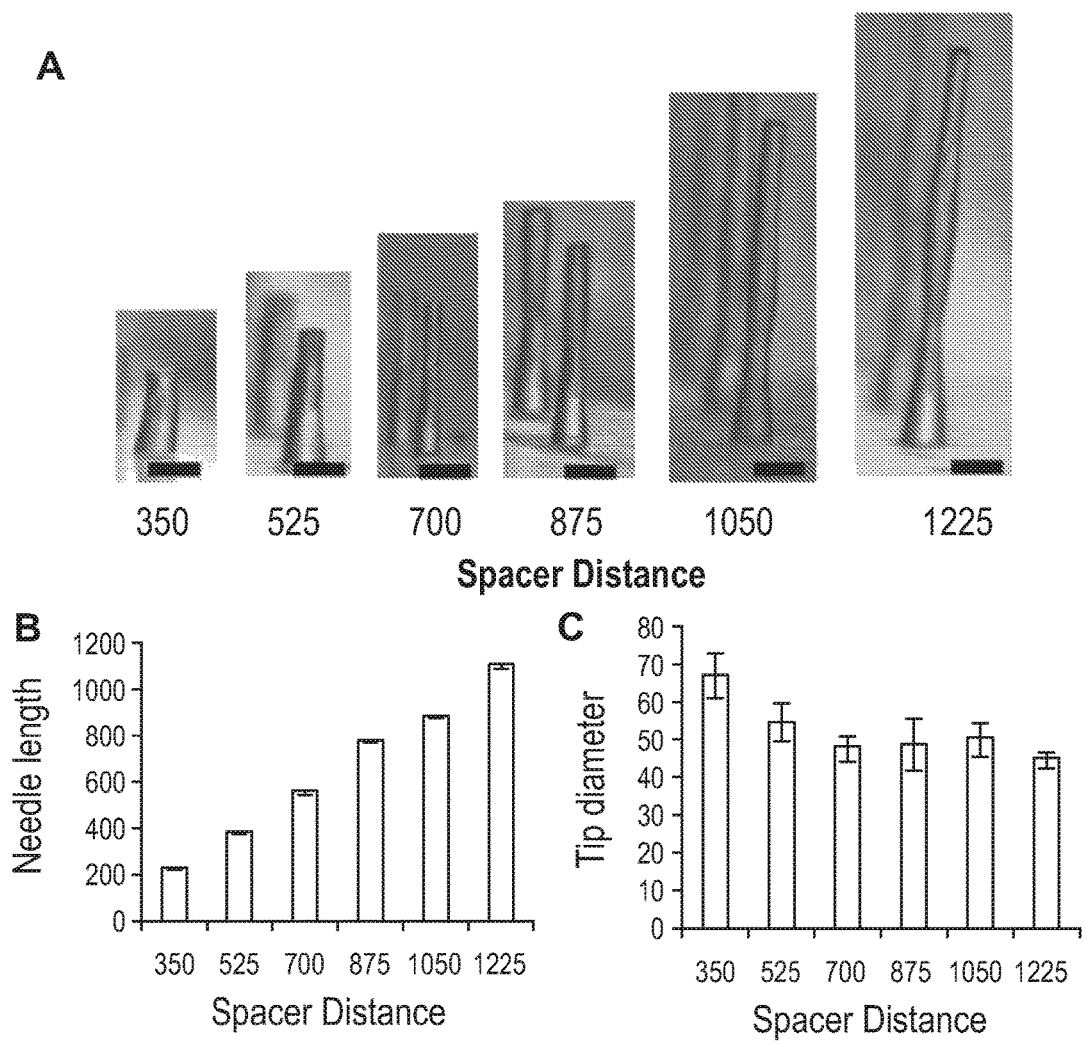
FIGS. 4A-4C show an effect of increasing number of spacers on: (A) Images at various spacers; (B) Increase in microneedle length with increase in spacers; (C) Decrease in the tip diameter with increase in spacers in accordance with an embodiment of the present disclosure.

For targeting the drugs to specific or target areas, locations, sites, or structures of the skin, microneedle length should be appropriately controllable/controlled. The inventors manipulated the spacer thickness by increasing the number of coverslips stacked on the base glass slide (FIG. 1(C)). Such a successive increase in the space between the base glass slide and the TMSPMA coated coverslip (which carries the PEGDA microneedle backing layer) increases microneedle length (ANOVA, $p<0.001$). At each step, one coverslip was added to the stack, thus increasing the spacer thickness by approximately 175 microns. The spacer thickness could be readily varied between 350-1225 microns. In this or an analogous, similar, or conceptually corresponding or related manner, microneedle length can be varied, for instance between 230 microns to 1150 microns, which is corroborated by the average coverslip thickness of 175 micron each (FIGS. 4(A) and 4(B)). An increase in the spacer thickness also resulted in a corresponding decrease in the tip diameter of the microneedles. For instance, tip diameter could be varied between 67 to 45 microns (FIG. 4(C)). The length and tip diameter of microneedle are important geometric parameters which govern the ease and depth to which the microneedle will penetrate in the skin, which is relevant for site specific biosubstance (e.g., drug/protein) delivery.

Microneedle Insertion in Pig Skin

Ascertaining that microneedles penetrate the skin, PEGDA microneedles, in an 8×8 array were inserted into excised cadaver pig skin obtained (after the pig was sacrificed using $CO_2$ asphyxiation) from a local abattoir. The hair was first removed using an electric hair clipper (Philips, Hong Kong) followed by hair removal cream Veet (Reckitt Benckiser, Poland) to completely remove the hair. The skin samples were cleaned and stored at $-80°$ C. until use. Prior to use, the subcutaneous fat was removed using a scalpel. The skin was fixed fully stretched on a thin modeling clay platform, to mimic the tissue-like mechanical support. Microneedles were inserted using the force of a thumb on the backing layer for approximately 1 minute.

The microneedle arrays were then removed and the area of insertion was stained with trypan blue for 5 minutes, which specifically stains the sites stratum corneum perforation. The excess stain was washed away with water. The areas stained with the dye were viewed by brightfield microscopy using Eikona Image Soft Microscope. A positive control, which consisted of a 27 gauge hypodermic needle, was used to create perforations in the form of a 4×3 array. Intact skin stained with trypan blue was used as a negative control.

Histological examination of the skin was also carried out by the microneedle-treated skin samples in to 10 μm sections using a microcryostat (Leica, Germany). The histological sections were stained with hematoxylin and eosin and imaged by stereomicroscopy. All animal experiments were approved by Institutional Animal Care and Use Committee (IACUC), National University of Singapore (NUS).

Encapsulation of a Model Drug: Imaging and In Vitro Release Rhodamine B was dissolved in the prepolymer solution at a concentration of 0.09, 0.17 and 0.44 weight %, respectively. The drug-laden microneedle samples were imaged using a fluorescence stereomicroscope (Nikon, Japan). The amount of drug encapsulated in the microneedles was calculated from the percent weight of the drugs in the prepolymer solution and the weight of fabricated microneedles. Selective incorporation of rhodamine B in the backing layer or microneedle shafts was made possible by using the prepolymer solutions containing the model drug to fabricate the backing layer or microneedles respectively. In vitro release of rhodamine B was tested by suspending fabricated microneedle arrays in 15 ml of 1×PBS, at 37° C. and sampled at regular intervals. At each sampling point, the whole 15 ml of release medium was withdrawn and replaced with 15 ml of fresh 1×PBS. The samples were stored at 4° C. before analysis. The amount released was quantified by measuring rhodamine B fluorescence at excitation and emission wavelengths of 554 nm and 586 nm, respectively, with a Tecan 2000 microplate reader (Tecan, Austria).

In Vitro Permeation Through Rat Skin

To analyze the increase in skin permeability following microneedle application, cadaver rat skin was used. The subcutaneous fat was removed with a scalpel. Microneedles containing 50 μg of rhodamine B were applied to the skin samples. As a comparative control, a similar concentration of rhodamine B in propylene glycol solution in the donor compartment was used. Skin was mounted on a side-by-side diffusion cell (TK-6H1, Shanghai Kai Kai Science and Technology Co., Ltd, China) with receptor compartment containing 4.5 ml of 1×PBS with 0.005% v/v sodium azide (Alfa Aesar, Lancaster, UK). For each group, six replicated were used. Water was circulated at 37° C. and the donor and receptor solutions were continuously stirred at 250 rpm with magnetic stirrers.

The samples were collected at regular intervals over a period of 48 hours. At each sampling point, 1 ml of receptor medium was withdrawn and replaced with 1 ml of fresh PBS. The samples were stored at 4° C. before analysis. All the samples vials were centrifuged at 10,000 rpm and supernatant was analyzed by measuring rhodamine B fluorescence as previously mentioned. Cumulative amount of drug permeated against time and skin permeability was calculated by assuming steady state flux.

Statistical Analysis

Testing of microneedle geometric properties, eight microneedle arrays were fabricated for each parameter studied and mean±standard deviation was reported. For other experiments, results from triplicate or more measurements were used to compute mean and standard deviation. One-way ANOVA was used, for analyzing multiple groups of data or statistical differences. Results with p value of less than 0.05 were considered to be statistically significant.

1.2. Results and Discussion:

1.2.1. Fabrication of Polymeric Microneedles

Effect of Varying UV Light Parameters

Microneedles were fabricated to ascertain the effect of various variables such as polymerization time, UV light intensity and distance from UV light source on microneedle length and tip diameter. All microneedles fabricated had a base diameter of 300 μm and center-to-centre spacing of 1500 μm. The spacer thickness between the base glass slide and the TMSPMA coated coverslip (with the microneedle backing layer attached to it) was kept constant at 1330 μm. All microneedles were viewed and the dimensions were measured by using a Nikon SMZ 1500 stereomicroscope.

Effect of Varying Polymerization Time

Figures 5A, 5B, 5C, 5D, 5E, 5F:
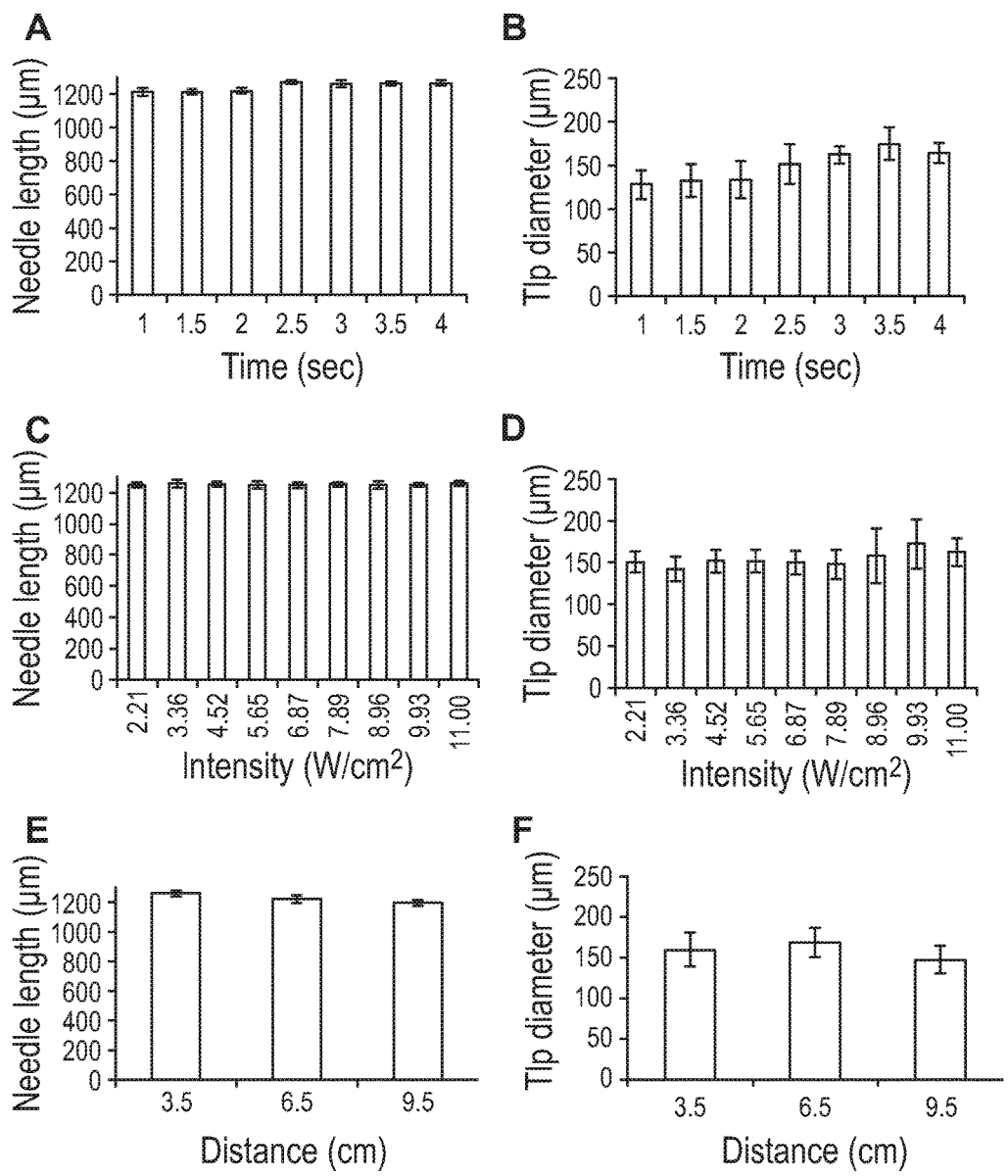
FIGS. 5A-5F show an effect of UV parameters on microneedle geometry. Effect on microneedle length of (A) Polymerization time (C) Intensity (E) Distance from UV source. Effect on tip diameter of (B) Intensity (D) Polymerization time (F) Distance from UV source in accordance with an embodiment of the present disclosure.

Microneedles were fabricated at different polymerization times ranging from 0.5 to 4 seconds, keeping the UV light intensity (11.0 W/cm$^2$) and the distance from UV light source (3.5 cm) constant. Uniform microneedle array cannot form at times below 1 second. At polymerization times beyond 1 second, microneedles started to form with an average length of 1218±18 μm until the exposure time of 2 seconds (p>0.05). Beyond that, the microneedle length increased to an average of 1268±16 μm till a maximum exposure time of 4 seconds (p>0.05) (FIG. 5(A)). Similarly, for times up to 2 seconds, the tip diameter averaged 131±18 μm, which increased to 163±17 μm with increase in exposure time between 2.5 and 4 seconds (FIG. 5(B)). Higher polymerization times can result in higher microneedle strength, which can be important for microneedle penetration in skin.

Effect of Intensity of UV light

The intensity was varied between 1.15-11.0 W/cm$^2$ maintaining the polymerization time (3.5 seconds) and distance from UV light source (3.5 cm) constant. Uniform microneedle array cannot form below the strength of 2.21 W/cm$^2$. Microneedle length averaged at 1250±4 μm and varying the intensity had insignificant effect on the microneedle length (p>0.05) (FIG. 5(C)). Average tip diameter of microneedle tip was found to be 154±8 μm (p>0.05) (FIG. 5(D)). The microneedles fabricated at 11.0 W/cm$^2$ were observed to be strong enough to be used for subsequent penetration experiments.

Effect of Varying Distance from UV Light Source

Variation of intensity of UV light with increase in the distance from the light source was tested for its influence on the microneedle length and tip diameter. For this purpose, the fabrication stage was placed at a distance ranging, 3.5 to 9.5 cm from the light source. Microneedles were fabricated at several distances within this range, keeping other variables of polymerization time (3.5 seconds) and ultra violet light intensity (11.0 W/cm$^2$) constant. It was observed that as the distance was increased, the microneedle length decreased from 1256±21 μm to 1190±70 μm. However the difference was found to be statistically insignificant between the distances 3.5 cm-6.5 cm and 3.5 cm-9.5 cm (FIG. 5(E)). Increasing the distance of the fabrication stage beyond 9.5 cm resulted in the formation of non-uniform arrays of microneedles with variable lengths. Tip diameter averaged at 156±10 μm with the increase in distance from 3.5 cm to 9.5 cm (FIG. 5(F)).

1.2.2. Effect of Non UV Light Parameters

Effect of Spacer Distance

For targeting the drugs to specific areas of the skin, microneedle length should be appropriately controlled. The inventors manipulated the spacer thickness by increasing the number of coverslips stacked on the base glass slide (FIG. 1(C)). Such a successive increase in the space between the base glass slide and the TMSPMA coated coverslip (which has PEGDA backing fabricated on it), increases the microneedle length (FIGS. 6(A)-6(F)). At each step one coverslip was added to the stack and thus increasing the spacer thickness by approximately 190 μm. The spacer thickness could be varied between 380-1330 μm. The UV parameters were kept constant at UV intensity (11.0 W/cm$^2$), polymerization time (3.5 seconds) and distance from UV source (3.5 cm). In this manner the microneedle length could be varied between 299±8 μm to 1387±35 μm, (ANOVA, p<0.001) which is corroborated by the average coverslip thickness of 190 μm each (FIG. 6(G)). An increase in the spacer thickness also resulted in a corresponding decrease in the tip diameter of the microneedles. The tip diameter ranged from 174±22 μm to 260±13 μm (FIG. 6(H)).

Microneedle Penetration in Pig Skin

Microneedles measuring 921±31 μm in length were inserted in cadaver pig skin. Penetration of microneedle arrays in the skin was demonstrated using the trypan blue staining method. FIG. 7(A) shows the image of a microneedle array penetration after staining. The blue spots are specifically stained at the points of microneedle insertion. Penetration with a hypodermic needle as a positive control and staining with trypan blue to ascertain the staining specificity and capability of the dye is displayed in FIG. 7(B). As a negative control, the dye was applied on intact skin. After washing, the stain was removed, proving that the blue dye only stains the sites of stratum corneum perforation (FIG. 7(C)). The microneedles were not deformed upon removal from the skin suggesting that they were robust enough to penetrate the skin. FIG. 7(D) shows the histological sections prepared after microneedles were inserted and removed subsequently. Hematoxylin and eosin staining to visualize the skin layers displays a clear indentation left by microneedle penetration. The microneedle penetrated almost completely into the skin suggesting that the encapsulated drug can be delivered efficiently.

Encapsulation and In Vitro Release of Encapsulated Model Drug

FIG. 3(A) shows the microneedles fabricated from PEGDA, in which no model drug has been incorporated. As observed from FIG. 3(B), the microneedle shafts contain the red colored Rhodamine B, whereas there is no fluorescence observed from the backing layer. Conversely, in FIG. 3(C), the microneedle shafts do not contain any Rhodamine B dye and the fluorescence is only observed in the backing layer, which specifically contains the dye. The drug can also be incorporated in both microneedles as well as the backing, which were also fabricated during this study (FIG. 3(D)).

The release of encapsulated rhodamine B was studied over a period of 1 week. It was observed that nearly 30% of the encapsulated drug was released within the first hour, as indicated in FIG. 8(A). The drug release continued as the drug loaded in the backing layer potentially serves as a reservoir. The percentage amount released was independent of the concentration of the drug in the microneedles and the backing layer. The actual amount released is shown in FIG. 8(B).

In Vitro Permeation Through Rat Skin

The ability of microneedles to increase skin permeability of rhodamine B was assessed.

Microneedle increased the total amount permeated by 3.89 fold as compared to a propylene glycol solution of rhodamine B (FIG. 9). The steady-state flux was 0.299±0.1 µg/cm$^2$/hr for microneedle and 0.067±0.01 µg/cm$^2$/hr for propylene glycol solution, which is 4.35 times lower ($p<0.05$).

Various embodiments in accordance with the present disclosure can provide a unified or single-step exposure process, such as a one-step lithographical process, to fabricate microneedles. The major equipment in this technique is the UV curing station.[44] The fabrication process involved free radical polymerization using the photoinitiator HMP, which initiates the polymerization reaction in the presence of UV. In addition, a fabrication setup in accordance with an embodiment of the present disclosure does not have specific requirements of vacuum or heating arrangements. Polymerization time ranging from 1-4 seconds, using an intensity 11 W/cm$^2$ (e.g., delivering 44 Joules of energy using a 4 second exposure time) did not significantly compromise the stability and/or structural and functional viability of the biosubstances under consideration. Such polymerization time/intensity/energy conditions are expected to substantially preserve or maintain the stability and/or structural and functional viability of biosubstances in general.

Fabrication of microneedles from PEGDA began with the process of optimization of fabrication conditions. As the inventors were developing this method to fabricate microneedles using ultra violet light governed photo polymerization, several variables were studied. The polymerization time (time of exposure of polymer to ultra violet light), ultra violet light's intensity and the distance of the fabrication assembly from the ultra violet light source was considered as factors influencing microneedle fabrication and were evaluated for their effect on microneedle geometry.

The time of exposure to UV light, defined as the polymerization time, is important with respect to the microneedle geometric properties as well the encapsulated drug stability. Ultraviolet light has been well known to cause primary photooxidation, which is the major contributor to drug degradation. One of the aims of the inventors' experiments was to study the geometric properties and develop a method of fabricating microneedles at the shortest possible polymerization time. The photopolymerization methods used to date involved long exposure times to UV in the range of 30 minutes. With the new approach, microneedle structures were obtained at low polymerization time of 1-4 seconds. Although microstructures could be formed at lower polymerization times as well, but as the time was increased the microneedle strength increased. A polymerization time of 3.5 seconds was used for microneedles fabricated in the current study as it resulted in robust microneedle arrays enabling penetration in skin. On the other hand, photopolymeric reactions can also be influenced by the intensity of the light source used. The inventors aimed to find the right combination of polymerization time and the UV intensity for fabricating robust microneedles. It was found that a combination of polymerization time of 3.5 seconds and intensity of 11.0 W/cm$^2$ was suitable for the inventors' method.

Penetration of microneedles in cadaver pig skin revealed that microneedles penetrated the skin with little force of a thumb. Trypan blue is a hydrophobic dye and is known to specifically stain the sites of stratum corneum perforation, which is confirmed by histological sectioning of the skin. Microneedles are intended to create transient pores in the skin structure and release the drug through these pores. These pores have been previously shown to close within 72 hours upon microneedle removal and microneedle application has been associated with a lower risk of microbial infection as compared to hypodermic needles.

Polymeric microneedles offer the advantage of incorporating the drugs in the polymeric matrix as compared to silicon or metallic counterparts where the drug can only be coated on pre-fabricated microneedles. Incorporation of drugs in microneedles fabricated from PEGDA demonstrates the encapsulation efficiency of PEGDA microneedles. The drugs have been incorporated either in the microneedle shafts for bolus release or the backing layer for sustained release or in both layers for a prolonged effect. The drug release from the microneedles in the surrounding subcutaneous tissue is followed by release of the drug encapsulated in the backing layer, which continues to release the drug through the transient pores created by the microneedles. Since it is possible to incorporate a larger amount of drug in the backing layer as compared to the microneedles, it is useful to incorporate the drug both in the microneedles and the backing layer to increase drug loading. The drugs encapsulated were released with a burst upfront in the first hour, which was followed by slower release over a period of one week of the study. This can be attributed to the reservoir capacity of the backing layer which can release the drugs through the microneedles inserted into the skin. In embodiments, the drug release properties can be modified by coating the microneedles with or incorporating varying amounts of release modifying polymers, such as chitosan, to control the release of the drug(s) from the PEGDA matrix. Other photo-crosslinkable polymers can also be used to alter the release profiles of the drug(s).

Drug laden microneedles when penetrated in rat skin models created transient pores which may have led to a higher flux as compared to a control, which included a propylene glycol solution containing the same amount of the drug as in one microneedle array. The microneedles increased the flux by over four times compared to passive diffusion of rhodamine B through the capillary intercellular pathways in the stratum corneum, which was the main mode of drug transport across the skin for a propylene glycol solution.

Experiment 2: Representative Process for Fabricating Biocompatible Polymeric Microneedles Containing a Representative Protein (e.g., BSA)

In the experiment, microneedles were fabricated to contain a model protein, bovine serum albumin (BSA). A method to encapsulate drugs in the polymeric core of the microneedles is reported ensuring the drug is uniformly distributed throughout the microneedle patch. For the purpose of testing the stability of encapsulated protein upon fabrication and in vitro release, the primary, secondary and tertiary structural features of the BSA using an array of analytical techniques were analyzed.

2.1 Experimental Procedures:

Materials

Poly (ethylene glycol) diacrylate ($M_n$ 258), 2-hydroxy-2-methyl propiophenone and bovine serum albumin were purchased from Sigma Aldrich (Missouri, USA). (3-(4,5-dimethylthiazol-2-yl)-2,5-diphenyl tetrazolium bromide) and dimethyl sulfoxide were purchased from MP Biomedicals (Ohio, USA). Bovine serum albumin Texas red conjugate was bought from Molecular Probes, Invitrogen (Orlando, USA). All other chemicals were of analytical grade and used as received.

Fabrication and Characterization of Polymeric Microneedles

The microneedles were fabricated by a novel soft lithography based process. Briefly, poly (ethylene glycol diacrylate) containing 0.5% v/v of 2-hydroxy-2-methyl propiophenone, hereinafter referred to as 'prepolymer' solution was exposed to a high intensity (20.9 W/cm$^2$) ultraviolet (UV) light source (EXFO® Omnicure, Quebec, Canada) to form the backing layer. In a similar step, the prepolymer solution was pipetted onto this backing layer and exposed to UV through a specifically patterned photomask. The microstructures thus formed, due to preferential exposure of the prepolymer solution in transparent regions of the photomask, represented micron sized rods defined as 'microneedles'. Excess of the unpolymerized prepolymer solution was washed away using purified water and microneedles let to dry in air. The geometric characteristics of the microneedles (length, base and tip diameter) were studied using an SMZ-1500 stereomicroscope (Nikon, Tokyo, Japan).

Uniform Drug Distribution in Microneedles

Bovine serum albumin Texas red conjugate was incorporated in the microneedle backing layer and shafts at a concentration of 0.045% w/w in the prepolymer solution to ascertain the uniform distribution of drug in polymerized microneedles. The fabricated microstructures were then imaged using a Nikon A-1R confocal microscope to observe the fluorescence intensity at various areas of the backing layer and various lengths of a microneedle shaft. The fluorescence intensity was calculated using Nikon NIS elements BR 3.1 analytical software. Microneedle arrays were also imaged with a SMZ-1500 stereomicroscope.

Stability Tests for BSA in Microneedles

Primary Structure Stability

Sodium dodecyl sulphate—polyacrylamide gel electrophoresis (SDS-PAGE) was carried out using Laemmli's method to assess the effect of UV-initiated photopolymerization on the conformational stability of bovine serum albumin. It was performed by casting 10% running gel and 5% stacking gel. Each formulation, containing 10 mg of protein sample as determined by BCA protein assay (Pierce®, Ill., USA), was mixed with an equal quantity of Laemmli sample buffer and 5% of β-mercaptoethanol. The solutions were heated at 100° C. for 2 minutes after which they were loaded on a comb stacked on the gel cast in an electrophoresis cell. The gel was run at 100 volts for 2.5 hours. After removal from electrophoresis cell, the gel was stained with Coomassie brilliant blue R-250 staining solution for 2 hours on an orbital shaker. The excess stain was removed by a destaining solution (20% methanol: 10% glacial acetic acid: 70% water) overnight and the gel was imaged using a Samsung digital camera.

Secondary Structure Stability

Circular dichroism (CD) spectroscopy was performed on the samples to evaluate the secondary structural characteristics of bovine serum albumin in the fabricated microneedles. The analysis was performed in a Jasco J-810 spectropolarimeter (Jasco, Tokyo, Japan) with a 1 mm light path quartz cell (Helima, Müllheim, Germany). Data was acquired at a bandwidth of 0.1 nm with a scan speed of 50 nm/min and a response time of 8 seconds. The samples and standard BSA solution were scanned over the wavelength range of 260 nm-200 nm. The microneedle release samples were first filtered using micro-centrifugal concentrators, (30 kDa cut-off) (Vivaspin 20, GE, UK) to separate the protein from polymer. Average value from triplicate measurements was used to plot the curve of molar ellipticity to wavelength. Molar ellipticity was calculated using the following equation:

$$[\theta] = \frac{\theta \cdot Mp}{10,000 \cdot n \cdot C \cdot l} \quad (1)$$

where Mp is the molecular weight of BSA (66,000 Da), n is the number of amino acid residues on BSA (583), C is the concentration of the BSA solution (0.000026 g/ml) and l is the path length of the cell (0.1 cm). The percentage of α-helix was calculated from the following equation $$\alpha-\text{helix}(\%) = \frac{-[\theta]_{208} - 4000}{33,000 - 4000} \times 100 \quad (2)$$

Tertiary Structure Stability

In order to evaluate the tertiary structural changes in the protein conformation, fluorescence spectra was analyzed for protein samples. Standard BSA solution at a concentration of 0.026 mg/ml in purified water was prepared to compare the spectral data with the BSA released from microneedle samples. The emission spectra were studied in the range of 300-400 nm at a fixed excitation wavelength of 280 nm using a Hitachi F-7000 fluorescence spectrophotometer. The fluorescence intensities were plotted against wavelength as an average of triplicate measurements.

In Vitro Release of BSA from Microneedles

BSA was encapsulated in the microneedles at three different concentrations (0.5, 0.8 and 1.3% w/w BSA in prepolymer solution) to obtain microneedle arrays containing 0.4-1.6 mg of the protein. The in vitro release was determined by suspending the microneedle arrays in 15 ml of 1× phosphate buffer saline at 37° C. Periodically, the release medium was withdrawn completely and replaced with 15 ml of fresh medium to maintain sink condition. The collected samples were kept at 4° C. until analysis. The protein concentration in release samples was analyzed by BCA protein assay kit (Pierce, Ill., USA). Each concentration was analyzed in triplicates and mean value was used for analysis. Cumulative amount in mg and the percentage of BSA released was plotted against time.

In Vitro Permeation of BSA Through Rat Skin

In vitro permeation studies were carried out in water jacketed horizontal diffusion cells (TK-6H1, Shanghai Kai Kai Science and Technology Co Ltd, Shanghai, China). The rat skin was hydrated in a receptor solution (1× phosphate-buffered saline with 0.005% v/v sodium azide) overnight. The skin was placed stretched on ten layers of Kimwipes (Kimberly-Clark, Roswell, Ga.) to provide tissue-like mechanical support. Microneedles containing 0.7%, 1.42%, and 1.85% w/w BSA were applied to abdominal rat skin after removing the subcutaneous fat. Microneedles containing no BSA were used to blank the inherent protein released from the skin. BSA dissolved in propylene glycol was used to compare the enhancement of BSA permeation by microneedles over passive diffusion. The microneedle array was secured on the skin using scotch tape and the skin was placed between the donor and receptor compartments. The receptor compartment was filled with 4.5 mL of receptor solution, which was continuously stirred at 250 rpm using a Teflon-coated magnetic stirrer. At each sampling point, 1 mL of receptor solution was withdrawn and replaced with fresh receptor solution. The collected samples were stored at 4° C. until they were analyzed. All samples were centrifuged at 10,000 rpm for 5 minutes and the supernatant was collected for analysis. The concentration of permeated BSA was determined by the ultraviolet $A_{215}$-$A_{225}$ method. Each sample was analyzed in triplicate. The cumulative amount of drug permeated per unit area was plotted against time.

In Vitro Cytotoxicity of Polymeric Microneedles

Cytotoxicity of poly (ethylene glycol diacrylate) was assessed by the viability of three different cell lines by colorimetric determination of mitochondrial succinate dehydrogenase activity using the conventional MTT, (3-(4,5-dimethylthiazol-2-yl)-2,5-diphenyl tetrazolium bromide) assay. Human dermal fibroblasts (HDF), human adult low calcium high temperature (HaCaT) keratinocytes and human embryonic kidney (HEK 293) cells were used to assess the toxicity of polymer used in fabricating the microneedles. The cells were grown in Dulbecco's modified eagles medium supplemented by 10% fetal bovine serum and 1% penicillin—streptomycin solution. After the cells achieved 80-90% confluency, they were trypsinized and counted. All three cells ($1\times10^4$ cells/well) were plated into 96-well microtitre plates (Corning, N.Y., USA) in 200 µL of growth medium. After 24 hours of plating, polymer extracts (prepared by extracting the polymer from fabricated microneedles in 1×PBS at 37° C. for 24 hours) were added to each well. Positive control consisted of wells containing 20 µL 1×PBS. The plates were incubated at 37° C. in humidified 5% $CO_2$ for 24, 48 and 72 hours. The medium was aspirated at respective analysis point and 20 µL of MTT solution (5 mg/ml in PBS) was added to each well followed by 200 µL of growth medium. The plates were incubated for 4 hours at 37° C. After 4 hours the medium was aspirated again and 150 µL was added to each well to dissolve the formed formazan crystals which were dissolved with the aid of a plate shaker operated at 100 rpm. The colorimetric assay was carried out by measuring the absorbance at 595 nm using a Tecan 2000 microplate reader (Tecan, Germany). The cell viabilities were calculated as a percentage of the control.

The toxicity of the polymer was also assessed by analyzing the amount of lactate dehydrogenase released from the membranes of damaged cells. The cells were plated in a similar manner as described above and treated with polymer extract and phosphate-buffered saline. Maximum lactate dehydrogenase release was achieved by treating the cells with the lysis solution (9% w/v Triton X-100) provided by the manufacturer. The assay was performed according to the manufacturer's protocol. The percentage toxicity was calculated using the following equation, where $Polymer_{LDH}$, $Vehicle_{LDH}$, and $Triton_{LDH}$ represent the respective fluorescence values obtained from wells treated with polymer, phosphate-buffered saline, and Triton X-100.

$$\text{Cytotoxicity}(\%) = \frac{Polymer_{LDH} - Vehicle_{LDH}}{Triton_{LDH} - Vehicle_{LDH}} \times 100$$

Statistical Analysis of Data

The graphs were plotted using Microsoft Excel 2007. All experiments were performed at least three times and data reported as mean±standard deviation. Statistical analysis of data was performed using PASW Statistics 18 Software (SPSS Inc.). Comparison amongst groups was made by computing analysis of variance (ANOVA). The difference was considered to be statistically significant for $p<0.05$.

2.2 Results and Discussion:

Fabrication and Characterization of Microneedles

The microneedles were imaged using a stereomicroscope and found to have an average length of 820 µm, base diameter 300 µm, center to centre spacing between needle 1500 µm and average tip diameter 140 µm. The microneedle patch consisted of an array of 8×8 needles spread over an area of 1.44 $cm^2$, which is small for self-administration of the microneedle, a unique advantage over conventional injection based delivery methods, thus offering higher patient compliance.

Incorporation and Uniform Drug Distribution in Microneedles

Drug incorporation in the polymeric matrix prior to microneedle formation allows for higher drug loading as opposed to coating the drug molecules on the fabricated microneedles. In this study, the inventors could achieve up to 1.6 mg of BSA per microneedle array. The inventor's process circumvents the long ultraviolet exposure and extensive preprocessing required for microneedle formation using the previous methods, which may impact protein stability. Moreover, the inventor's process does not involve any mold-based or template-based processing, potentially avoiding interactions between mold or template material and fragile protein molecules.

Figure 10:
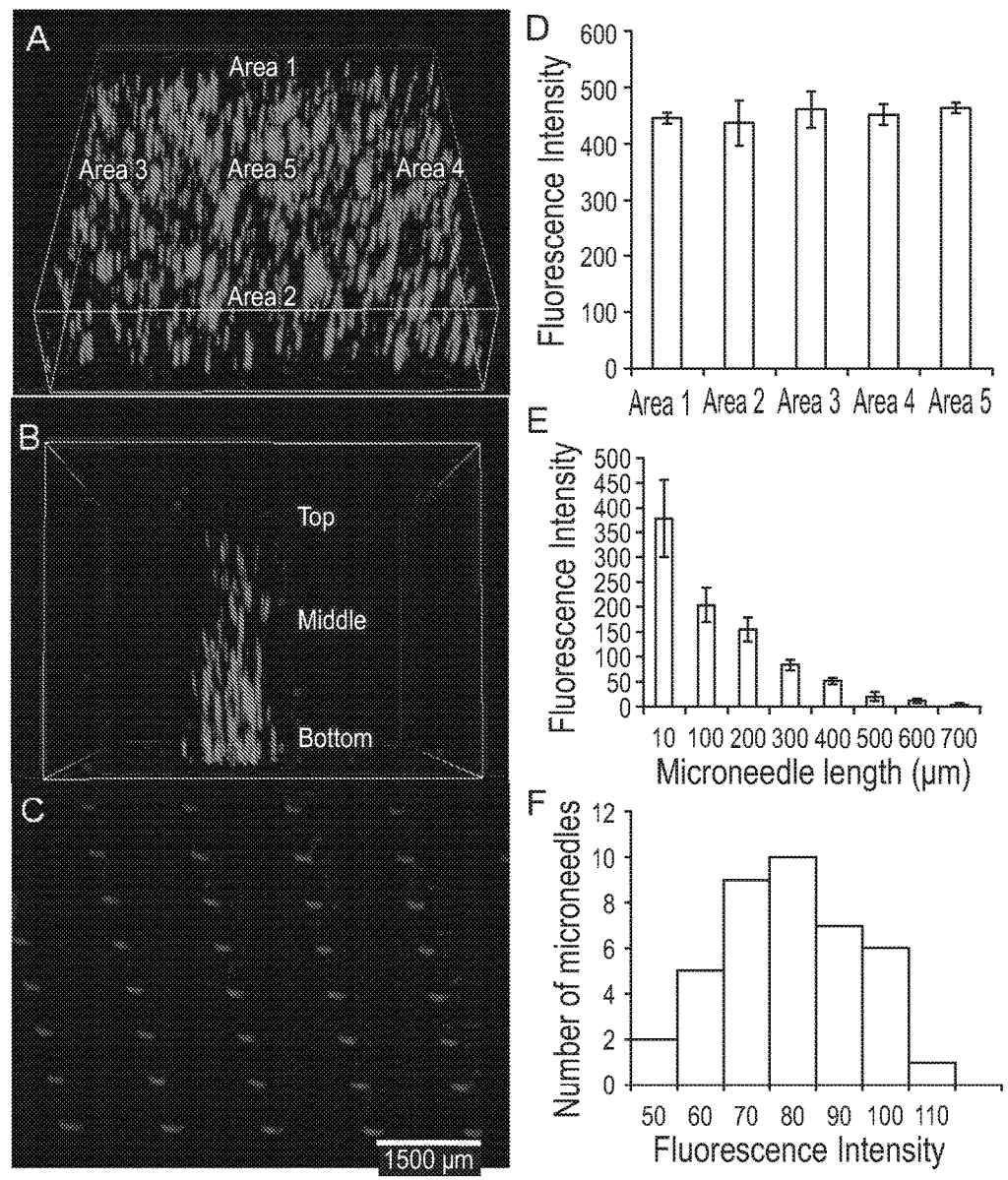
FIGS. 10A-10F show an encapsulation of bovine serum albumin Texas red conjugate (TR-BSA) in polymeric microstructures shows uniform distribution. Uniformly distributed TR-BSA in: (A) microneedle backing; (B) microneedle shaft as observed by confocal microscopy; (C) A microneedle array as observed by a stereomicroscope. Quantitative estimation of fluorescence intensity shows uniform distribution over; (D) different areas of the backing layer (n=3); (E) different length on a microneedle shaft (n=6); and (F) different microneedles of an array in accordance with an embodiment of the present disclosure.

An important aspect of any drug delivery system is the uniform distribution of drug throughout the system to ensure a constant dose is encapsulated and subsequently delivered. As polymeric microneedles fabricated in accordance with embodiments of the present disclosure can be an efficient carrier for transdermal protein delivery, the inventors encapsulated Bovine serum albumin Texas red conjugate (TR-BSA) to visualize the distribution of the protein in the microneedle backing and the shafts. TR-BSA shows peak excitation ($\lambda_{ex}$) and emission ($\lambda_{em}$) at 596 nm and 615 nm respectively, which can be quantified using fluorescence microscopy. The inventors employed confocal imaging as a tool to image the microneedle sample to assess the fluorescence distribution at different areas and depths of the microstructure. As observed from FIGS. 10(A) and 10(D), fluorescence is distributed across different areas of the backing layer in a uniform pattern ($p>0.05$). However, as the microneedle length increased from the bottom of the array (length=10 µm) to the microneedle tip (length=700 µm), the fluorescence was observed to decrease from 377 to 3.1 (FIGS. 10(B) and 10(E)). This can be attributed to the inherent microneedle geometry as the microneedle shafts are broader at the base than the tip, owing to lesser drug being encapsulated in the tip region of the microneedles. The drug distribution amongst different microneedles in an array was constant with majority of the microneedles showing a uniform fluorescence (FIG. 10(F)). This is expected to ensure uniform drug delivery over the patch area of 1.44 $cm^2$. FIG. 10(C) shows a stereomicroscope image of a complete microneedle array, revealing that the drug is evenly distributed throughout the microneedle patch.

Stability Tests for BSA in Microneedles

Microneedles have been considered as an ideal drug delivery system to deliver therapeutic peptides, proteins, and vaccines. As the biological function of a protein is dependent on its conformation, it is imperative to design a dosage form which does not adversely affect the stability of these fragile molecules. In the inventors' fabrication process, the inventors used an ultra violet light based photo-cross-linking method for creating polymeric microstructures. UV light has been previously reported to cause protein denaturation and structural changes in primary, secondary and tertiary structure of proteins. The inventors ascertained these three structural features in this study by investigating the sodium dodecyl sulfate polyacrylamide gel electrophoresis (SDS-PAGE), circular dichroism spectra and fluorescence intensity measurement of bovine serum albumin encapsulated in the microneedles. While the results here demonstrate that the conformation of BSA was maintained throughout the fabrication process and the subsequent release experiments, the structural and biological properties of other proteins might be different and depend on individual protein characteristics.

Figure 11:
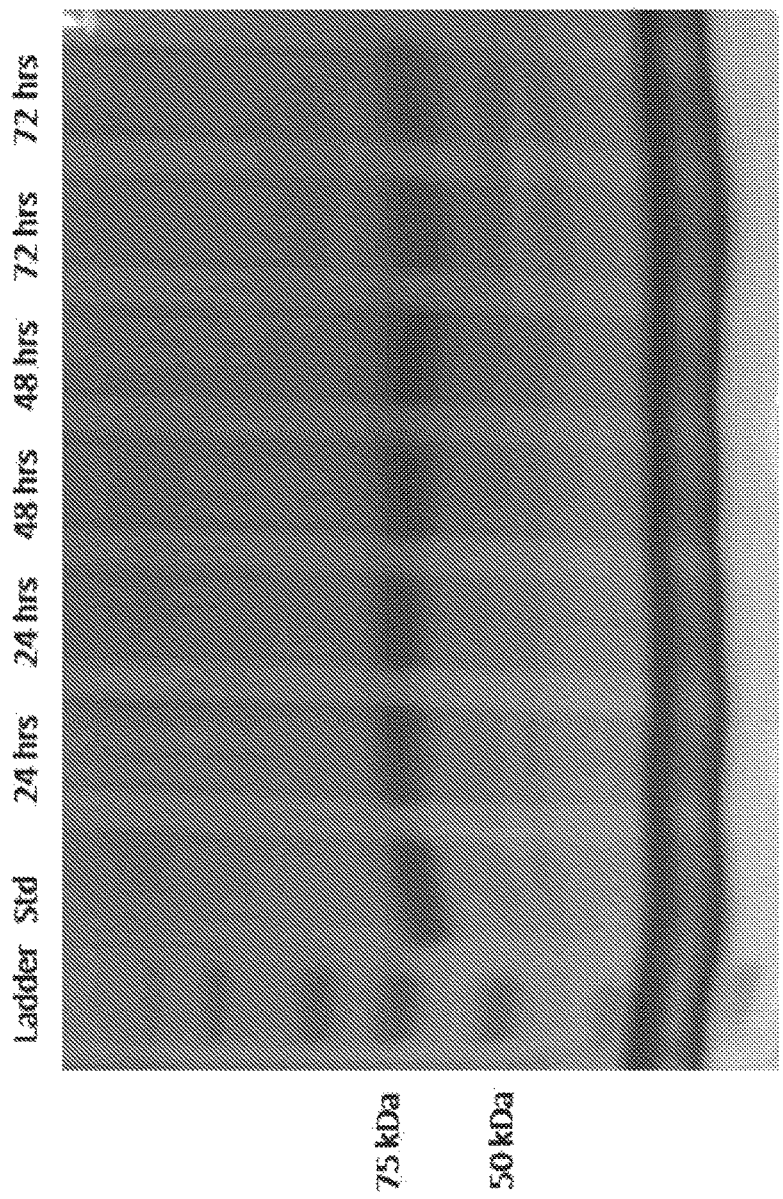
FIG. 11 shows SDS-PAGE images of protein standard marker, bovine serum albumin standard and bovine serum albumin released from microneedles after 24, 48, 72 hours (M.W.: 66 kDa) in accordance with an embodiment of the present disclosure.

SDS-PAGE has been the most common method in the separation of proteins and determination of protein molecular weight. It has been used previously to determine the structural integrity of BSA in microspheres. In this study, the inventors used SDS-PAGE to determine the amino acid sequence of BSA and analyze any deleterious effect of UV radiation on the protein (FIG. 11). BSA released from the formulation was compared to a freshly prepared solution and a protein standard marker. The single line of bands appearing at 66 kDa suggests that the protein was stable during the fabrication process and remained stabled in the dosage form for a period of 72 hours. There were no other bands observed during the electrophoretic separation providing the evidence against any protein aggregation to form dimer or multimer or fragmentation to smaller subunits, indicating the primary structure of BSA remained intact during the fabrication process.

Figure 12B:
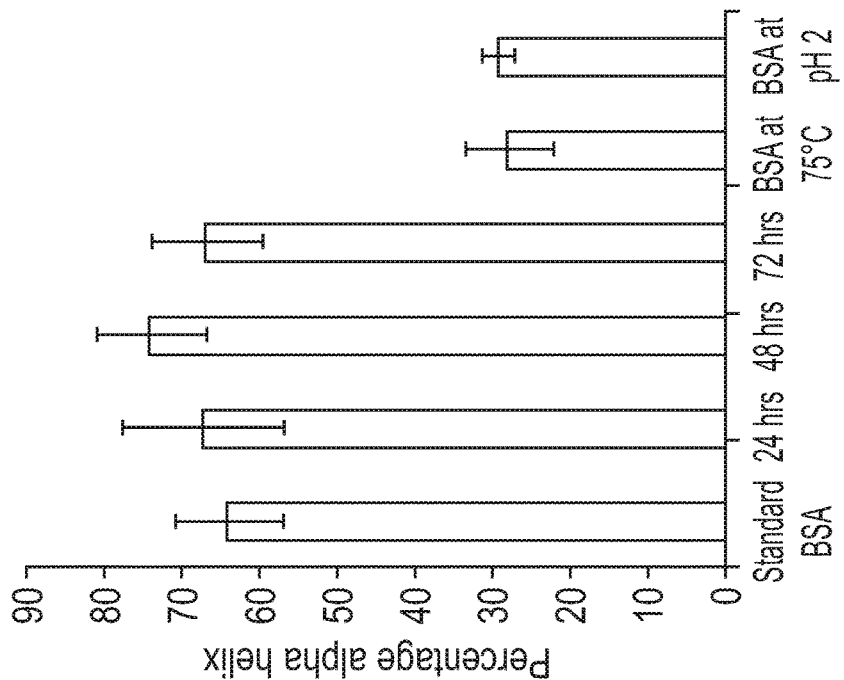
FIGS. 12A-12B show a circular dichroism analysis to assess the stability of encapsulated BSA. Stability of BSA released from microneedles after storage for 3 days at 37° C. is compared with freshly prepared BSA solution and BSA degraded by heating at 75° C. and under acidic conditions of pH 2: (A) mean residue ellipticity and (B) percentage of alpha-helix. All results confirmed the alpha helix structure of BSA was preserved during encapsulation and release over a period of 3 days in accordance with an embodiment of the present disclosure.
Figure 12A:
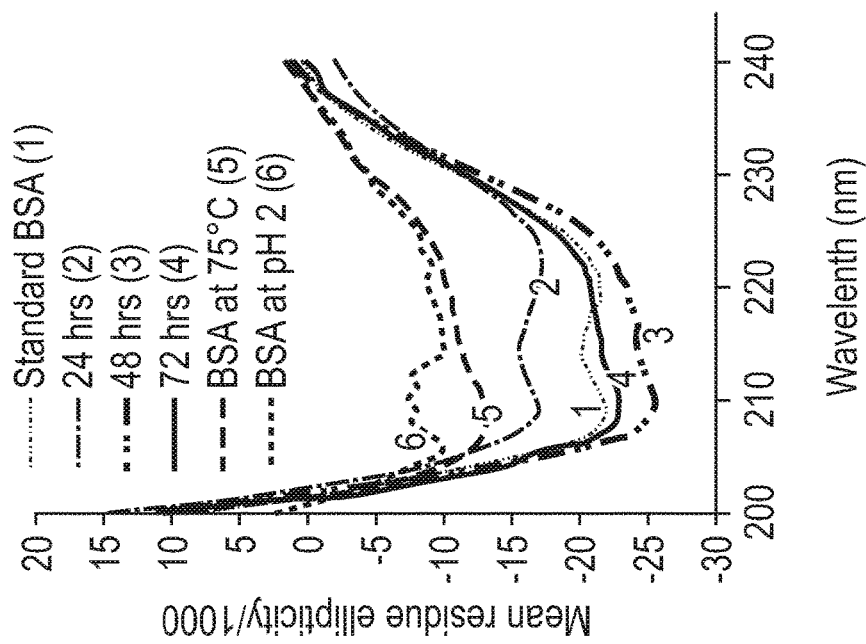

The secondary structure of BSA was assessed by a commonly used technique known as circular dichroism. BSA contains 67% of α-helix, 10% of turn and no β-sheet. The far UV CD spectrum (260-200 nm) has been used to characterize the structural stability of BSA. α-helix structure is indicated by two negative peaks at 208 and 22 nm with a minimum peak at 208 nm, which is attributed to n→π* and π→π* transition of the α-helix structure. It was observed that the secondary structure of BSA encapsulated in the microneedles was similar to a freshly prepared solution of BSA as shown in FIG. 12(A).

The degraded BSA used as control showed significantly lower ellipticity values that the standard BSA and microneedle release samples. The percentage of α-helix was calculated using equation 2 and was corroborated and consistent with the reported amount of helix in the native BSA structure (about 67%). The percentage of α-helix in the BSA released form microneedle samples was comparable with a freshly prepared solution of BSA (p>0.05) (FIG. 12(B)) and significantly different from heat-denatured and acid-denatured BSA samples (P<0.05). These results proved or demonstrated that secondary structural integrity of BSA was maintained during ultra violet (UV) dependent photopolymerization.

One manner of characterizing, analyzing, estimating, or determining a relative amount of protein remaining stable after microneedle fabrication (e.g., after UV based photo-crosslinking) is to examine % alpha helix data. For instance, within standard deviation limits, for protein released in an in vitro medium (PBS) averaged for 3 days, the relative amount of protein remaining stable was 94.99±9.5% as compared to a freshly prepared solution of BSA.

Figure 13:
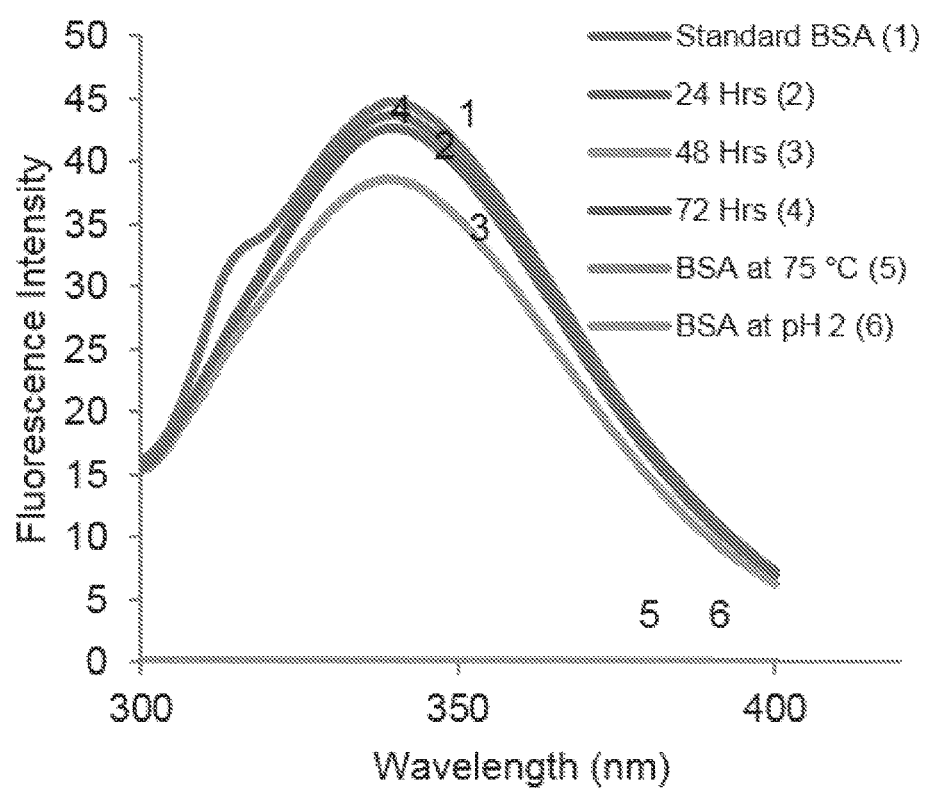
FIG. 13 shows a fluorescence spectroscopic analysis to assess the tertiary structure of encapsulated BSA. Stability of BSA released from microneedles after storage for 3 days at 37° C. is compared with freshly prepared BSA solution and BSA degraded by heating at 75° C. and under acidic conditions of pH 2 by analyzing emission spectra of BSA. Peak BSA emission wavelength was found to be similar for all samples in accordance with an embodiment of the present disclosure. No fluorescence was observed in degraded BSA samples.

As proteins contain aromatic amino acids like tyrosine, tryptophan and phenylalanine, which are inherently fluorescent, the fluorescence spectra and intensity can be used as a marker of protein structural stability. Tryptophan is the most dominant fluorophore which displays the largest extinction coefficient. Thus the emission spectra of proteins can be measured, for instance at one or more wavelengths such as a fixed excitation wavelength of 280 nm. The emission maximum of tryptophan in water is observed around 350 nm and is dependent on the polarity of the solvent. BSA emission spectra were scanned between 300-400 nm and an emission maximum was observed at 338 nm for all the release samples and a standard solution of BSA (FIG. 13). This is in accordance with previously reported results and proves the feasibility of the inventors' fabrication process to retain the protein stability in the microneedles. On the other hand, BSA samples denatured using heat or acid did not show any fluorescence (excitation wavelength of 280 nm and emission wavelength of 300-400 nm). In view of the foregoing, an additional or alternative manner of characterizing, analyzing, estimating, or determining a relative amount of protein remaining stable after microneedle fabrication (e.g., after UV based photo-crosslinking) is to monitor, examine, or analyze fluorescence spectra, e.g., with respect to the intensity of fluorescence and the wavelength of its maximum $\lambda_{max}$, and/or changes or shifts in fluorescence spectra in view of a set of reference fluorescence spectra. Such examination can be compared to reference fluorescence spectra involving fresh protein and/or protein subjected to one or more reference denaturing UV illumination exposures, one or more reference denaturing temperatures and/or one or more reference chemical denaturants.

Comprehensive analysis of primary, secondary and tertiary structure stability of a model protein BSA indicate that the microneedles can serve as a carrier for proteins, protein fragments, or protein/protein fragment based drugs. The UV based photo-crosslinking did not significantly alter the structural properties of BSA possibly due to short time of exposure at a high intensity.

In Vitro Release of BSA from Microneedles

The release profile of BSA is depicted in FIG. 14(A) (percentage release) and FIG. 14(B) (cumulative amount). The inventors used phosphate buffered saline (PBS) with a pH of 7.4 as a release medium as it closely resembles extracellular fluids and plasma. It was observed that most of the drug encapsulated in the microneedle array was released within a period of 6 hours. The amount released corroborated with the amount encapsulated in the microneedles demonstrating a control of the drug quantity that can be encapsulated and released effectively in an in vitro environment. Most of drug was encapsulated in the microneedle backing layer (~90%) and the needles owing to their micron scale geometry contain less drug.

As BSA is a hydrophilic molecule, it was released at a rapid rate from the microneedles. More controlled release profiles can be expected if the drugs are encapsulated in a polymeric shell or fabricated structures (e.g., microspheres) before incorporating in the microneedles.

The transient pores created by microneedles and the diffusion of drug through the polymeric layer to the epidermal and dermal regions to create a depot of protein drugs have been implicated. The drugs can be subsequently absorbed into the blood stream or lymphatic circulation. It is expected that the released protein will accumulate in the sub-epidermal tissues and rapidly absorbed from the highly vascularised regions lying underneath.

In Vitro Permeation of BSA Through Rat Skin

Microneedles increased the amount of bovine serum albumin (BSA) permeated as compared to passive diffusion of BSA. As BSA is a large molecule (66 kDa), it cannot passively diffuse through the skin. FIGS. 15A-15B show the increase in the cumulative amount permeated per unit area on microneedle application as compared to propylene glycol solution of BSA, which practically showed no BSA at the end of 48 hours. The amount permeated in the case of microneedles increased with the increase in encapsulated amount of BSA. The permeation curve resembles the in vitro release profile observed in the PBS buffer, with an initial burst release followed by a slow release phase. Such permeation profiles are common for other highly water soluble drugs such as calcein (log p=−5.02). However, the inventors observed in their previous studies that lipophilic drugs (e.g. rhodamine B, log P=2.43) do not show a burst in permeation and their absorption is somewhat limited by their interaction with stratum corneum lipids. The $A_{215}$-$A_{225}$ method has been previously used in determining the BSA concentration in in vitro permeation studies. The concentration of BSA is a linear function of the difference between extinction at 215 nm and 225 nm. The method is sensitive for protein concentrations as low as 5 ng/mL, which are usually expected in in vitro permeation studies. The protein concentration was calculated using the following equation:

$$BSA \text{ concentration } (\mu g/mL)=144\times(A_{215}-A_{225}) \quad (3)$$

Microneedles containing no BSA were used as control to minimize any absorption from the dissolved polymer. When lower amount of BSA was encapsulated, the permeation curve demonstrated a plateau at nearly 18 hours, as most of the drug was released. When higher amounts were encapsulated, the protein continued to be released at the end of 2 days, suggesting that the microneedle array developed in the study is amenable to dose adjustment as per the requirements of the therapeutic regimen. As compared with microneedles, passive diffusion of BSA using a propylene glycol solution did not result in any significant amount of drug permeation through the skin.

Conventional skin permeation where steady state can be established is based on the fact that the donor concentration is constant throughout the diffusion process. This can be proven by Fick's first law for membrane diffusion. However, in this study, the donor concentration decreased during the permeation process. Moreover, it is not a pure membrane diffusion process because micropassages were created by these microneedles, making the process a combination of diffusion through the skin membrane and mass transport through micron-sized channels across skin.

In Vitro Cytotoxicity of Polymeric Microneedles

Two cell lines, viz, human dermal fibroblasts (HDF) and human adult low calcium high temperature (HaCaT) keratinocytes were representative of dermal and epidermal skin cells and hence were used to assess the toxicity of polymeric microdevice on the skin. These cell lines have been used previously to study the toxicity of transdermal polymeric dosage forms. The third cell line, human embryonic kidney (HEK293) cells was used as it is a representative of healthy human cells. HEK293 cells have been used in numerous in vitro toxicity studies as a representative of human cells since they offer a convenient model to evaluate the toxicity at the cellular level. They have also been previously reported in transdermal toxicity from topical gels. Using three different cells, the inventors aimed to assess the transdermal and systemic biocompatibility of the inventors' novel polymeric microneedles.

The most commonly used MTT assay was used to assess the toxicity of the poly (ethylene glycol) diacrylate to these cells. Viable cells, possessing active mitochondrial succinate—tetrazolium reductase system reduce MTT to formazan crystals which were quantified by colorimetric determinations. The cell viabilities as % of the control were calculated as $A_{polymer}/A_{control}\times100$, where $A_{polymer}$ and $A_{control}$ were the absorbance measurements of the wells containing polymeric extracts and control (PBS) respectively. Each value was an average of six replicates.

High cell viabilities with respect to the control were reported for HDF and HaCaT cells for exposure of cells to polymeric extracts up to 72 hours (FIGS. 16(A) and 16(B)), with cell survival numbers statistically insignificant between 24-72 hours viability assays (p>0.05). This ensures that the polymer used for fabricating microneedles is safe for transdermal use and is non-irritant to epidermal and dermal cells. This emphasizes the advantage of biocompatible polymers being used for topical application. HEK293 cell viability assays yielded similar viability for the first 24 hours, which subsequently decreased (p<0.05) (FIG. 16(C)). However, it has been reported in literature that PEGDA with molecular weight less than 20,000 Da can be cleared rapidly by the kidney by dissolution in the body fluids. Hence the inventors expect minimal systemic toxicity due to PEGDA owing to its rapid clearance.

Fluorometric determination of lactate dehydrogenase leaked out from damaged cell membranes into the supernatant medium has been accepted as a method to determine the cytotoxicity of compounds and has been previously used for polymers as well. In the inventors' study, low cell toxicities were observed in all the three cell lines for cells treated with polymer extracts. As shown in FIGS. 16D-16F, the percentage cytotoxicity for cells treated from 24-72 hours did not vary significantly (P>0.05), supporting the results from the MTT assay and further proving the biocompatibility of polyethylene glycol diacrylate.

Overall, the in vitro toxicity results showed non toxic behaviour of the polymeric microneedles, both transdermally and systemically and hence microneedle device embodiments in accordance with the present disclosure can provide a safe and efficient drug carrier for encapsulating and delivering biosubstances.

In embodiments, the photolithographic technique of the present disclosure can be used to encapsulate a bioactive substance(s) (i.e., drugs, proteins, and/or protein drugs). Drug distribution can be uniform across the microneedle array. Moreover the process of fabrication of microneedle devices of the present disclosure can maintain bioactive substance stability and thus can retain the biological activity of the encapsulated bioactive substance(s). In embodiments, the encapsulated bioactive substance(s) can be released and permeated through skin in much larger amounts as compared with passive diffusion. In vitro biocompatibility of the polymeric microneedles of the present disclosure has been demonstrated by the low toxicity of the polymeric extracts on different cell lines, indicating the safety of these microneedles. In embodiments, the microneedles of the present disclosure can serve as a useful bioactive substance delivery system to deliver a bioactive substance(s).

Representative Microneedle-Integrated Thick Patch Device Fabrication and Testing Experiment The present disclosure also relates to a microneedle-integrated thick patch that can be used for encapsulating a large or larger amount of a bioactive substance (i.e., a drug and/or a protein) or bioactive substances (i.e., drugs and/or proteins). The present disclosure further relates to a process for fabricating a microneedle-integrated patch that can be used for encapsulating a larger amount of a bioactive substance or bioactive substances.

In embodiments, a microneedle-integrated thick patch of the present disclosure can be used for encapsulating a larger amount of a bioactive substance (i.e., a drug and/or a protein) or bioactive substances (i.e., drugs and/or proteins). In embodiments, a microneedle-integrated thick patch of the present disclosure can be used to increase the bioactive substance loading capacity of the microneedles. The encapsulation of larger amounts of a bioactive substance or bioactive substances and/or the increase in the bioactive susbstance loading capacity of microneedles is relevant and useful for treating diseases such as chronic pain and/or neuropathic pain where a high dose of a bioactive substance or bioactive substances is required. In embodiments, a microneedle-integrated thick patch of the present disclosure can be used to treat diseases such as chronic pain and/or neuropathic pain where a high dose of a bioactive substance or bioactive substances is required.

Experiment: Representative Biocompatible Polymeric Microneedle-Integrated Thick Patch that can be Used for Encapsulating a Large or Larger Amount of a Bioactive Substance (e.g., a Model Drug Such as Rhodamine B or a Drug Such as Lidocaine) and a Representative Process for Fabricating Thereof In the experiment, a microneedle-integrated thick patch was used for encapsulating a large or larger amount of a bioactive substance (i.e., a model drug such as rhodamine B or a drug such as lidocaine) was fabricated. Rhodamine B was used as a model drug to demonstrate drug encapsulation by the microneedle-integrated patch as well as selective drug encapsulation in different layers of the microneedle-integrated thick patch. The fracture force of the microneedles was determined. Further, the efficacy of the microneedle-integrated thick patch for encapsulating lidocaine and managing neuropathic pain was investigated. The fabrication method is based on photolithography, involving exposure of a polymer to UV light through a patterned mask. The technique offers the advantage of short exposure to UV light.
Experimental Procedures, Results and Discussion:
Materials Poly (ethylene glycol) diacrylate [PEGDA ($M_n$ 258)], 2-hydroxy-2-methyl-propiophenone (HMP) and 3-(trimethoxysilyl) propyl methacrylate (TMSPMA) were purchased from Sigma-Aldrich (St. Louis, Mo.). Rhodamine B was purchased from Alfa Aesar (Lancaster, UK). Lidocaine was purchased from Sigma-Aldrich. All materials used were reagent grade and were used as received.
Coating of Glass Coverslips Glass coverslips (Cell Path, Wales, UK, 160-190 micron thickness, 22×22 mm) were immersed in TMSPMA solution overnight for coating. The coverslips were then baked for 2 hours at 70° C.; the resultant chemical interaction is depicted in FIG. 1(B).
Fabrication of Microneedle Backing Layer Two uncoated coverslips were supported on either side of a glass slide (Sail Brand, China) as shown in FIG. 1(B) and FIG. 17(A) to create cavity or chamber having a space approximately 175 μm deep or thick. The TMSPMA coated coverslip was then placed on/over this setup. PEGDA containing 0.5% of HMP (referred to as the prepolymer solution) was wicked by capillary action into the gap between the coverslip and the glass slide (i.e., into the interior of the chamber). The setup was irradiated with high intensity ultra violet light of 12.4 W/cm² for 1 second using EXFO OmniCure® S200-XL UV curing station (UV filter 320-500 nm) (EXFO, Photonic Solutions Inc., Canada). The intensity of the UV light was measured with the OmniCure® R2000 radiometer (EXFO, Photonic Solutions Inc., Canada). A collimating adaptor (EXFO 810-00042) was used with the UV light probe. TMSPMA molecules bonded to the glass coverslips are covalently linked to the methacrylate groups of PEGDA via free-radical polymerization (FIG. 1(B), within dashed ellipses). The backing layer, which was approximately 175 μm thick, was easily removed from the setup. In embodiments, the backing layer can have a thickness or height of 212±22 μm. In embodiments, the backing layer can have a thickness or height between 175 to 350 μm.

212±22 μm in height while the thick patch was 1054±34 μm in height. The thin backing can be ranged between 175-350 μm
Fabrication of Microneedles In a number of embodiments, the setup for fabrication of microneedles is analogous or similar to that for the microneedle backing except for the number of spacers. The number of spacers will govern the length of the microneedle(s) fabricated. Increasing spacer thickness was achieved by increasing the number of coverslips stacked on either side of the base glass slide as shown in FIG. 1(C) AND FIG. 17(B). The precursor solution was then similarly wicked by capillary action into this gap as during the fabrication of backing layer. A plastic film was inked specifically in the pattern of microneedle array design. The background of the film was inked leaving small circles in an array pattern transparent to allow the UV light to pass through (Infinite Graphics Pte. Ltd., Singapore). This patterned film (also called a photomask, FIG. 2.) was designed to have various diameters of transparent circles in an array pattern, which govern the base diameter of the microneedles. Similarly, the center-to-center spacing between the two microneedles can be controlled. Such a film was placed on the fabrication setup which was subsequently irradiated with high intensity UV light. The use of the photomask blocked the UV access in the inked regions and allowed the UV light to pass through the transparent circles, which resulted in the formation of microneedle structures, thereby forming the microneedles, which covalently bonded with the PEGDA macromers in the backing layer to form an interpenetrating polymer network (IPN) (FIG. 1(C), within dashed rectangles). The microneedle structures, attached to the coverslip/backing layer, were carefully removed from the base glass slide and washed with deionized water to remove the uncross-linked precursor solution. The prepared microneedles were then imaged using Nikon SMZ 1500 stereomicroscope (FIG. 18(A)). The fabricated microneedles had an average length of about 889±48 μm, base diameter of about 334±43 μm and center to center length of about 1474±39 μm.
Fabrication of a Thick Backing Layer Patch A thick backing layer was fabricated separately as shown in FIG. 16C. Two uncoated glass slides were supported on either side of a glass slide (Sail Brand, China) as shown in to create a cavity or chamber having a space approximately 1100 μm deep or thick. A coverslip was then placed on/over this setup. PEGDA, containing 0.5% of HMP (referred to as the prepolymer solution) was wicked by capillary action into the gap between the coverslip and the glass slide (i.e., into the interior of the chamber). The setup was irradiated with low intensity ultra violet light of 5.8 mW/cm² for 15 seconds using EXFO OmniCure® S200-XL UV curing station (UV filter 320-500 nm) (EXFO, Photonic Solutions Inc., Canada). The intensity of the UV light was measured with the OmniCure® R2000 radiometer (EXFO, Photonic Solutions Inc., Canada). A collimating adaptor (EXFO 810-

00042) was used with the UV light probe. The glass coverslip is covalently linked to the methacrylate groups of PEGDA via free-radical polymerization. The thick backing layer patch, which was 1054±34 μm thick, was easily removed from the setup. The fabrication of the thick backing layer patch was achieved by exposure to low intensity ultra violet light of 5.8 mW/cm$^2$ for 15 seconds. In embodiments, the thick backing layer patch can be fabricated by exposure to low intensity ultra violet light of 5.8 mW/cm$^2$, less than 5.8 mW/cm$^2$ or greater than 5.8 mW/cm$^2$. In embodiments, the thick backing layer patch can be fabricated by exposure to low intensity ultra violet light for 15 seconds, less than 15 seconds, or greater than 15 seconds. In embodiments, the thick backing layer patch can have a thickness or height between 1000 to 3000 μm.

Fabrication of a Microneedle-Integrated Thick Patch

Referring to FIG. 16D, the thick backing layer patch was then integrated with the fabricated microneedles by pouring a drop of prepolymer solution between the surface of the backing layer and the surface of the thick backing layer patch and exposing both the backing layer and thick backing layer patch to high intensity ultra violet light of 12.9 W/cm$^2$ for 3 seconds. The thick backing layer patch is chemically coupled to the backing layer via the prepolymer solution. As mentioned above, the fabricated microneedles had an average length of about 889±48 μm, base diameter of about 334±43 μm and center to center length of about 1474±39 μm. In embodiments the backing layer and thick backing layer patch can each be made from a different biocompatible polymer.

Encapsulation of a Model Drug and Selective Encapsulation of a Model Drug

As a model drug, rhodamine B was used to demonstrate drug encapsulation and selective drug encapsulation in the different layers of the microneedle-integrated thick patch.

Rhodamine B was dissolved in the prepolymer solution(s) at a concentration of 0.075_weight %. Selective incorporation of rhodamine B in the backing layer, microneedle shafts and/or thick backing layer patch was made possible by using the prepolymer solutions containing the model drug to fabricate the backing layer, microneedles and/or thick backing layer patch respectively. Referring to FIG. 18B, drug-laden microneedle-integrated thick patch samples were imaged using a fluorescence stereomicroscope (Nikon, Japan).

The amount of drug encapsulated in the microneedles was calculated from the percent weight of the drug in the prepolymer solution and the weight of fabricated microneedles. The amount of drug encapsulated in the backing layer was calculated from the percent weight of the drug in the prepolymer solution and the weight of the backing layer. Likewise, the amount of drug encapsulated in the thick backing layer patch was calculated from the percent weight of the drug in the prepolymer solution and the weight of the thick backing layer patch. In embodiments, a large amount of a bioactive substance (i.e., a drug and/or a protein) or bioactive substances (i.e., drugs and/or proteins) can be encapsulated in a microneedle-integrated thick patch of the present disclosure. In embodiments, a bioactive substance or bioactive substances can be encapsulated in the backing layer, microneedle shafts, and/or thick backing layer patch of a microneedle-integrated thick patch of the present disclosure. Since it is possible to incorporate a larger amount of a bioactive substance or bioactive substances in the thick backing layer patch compared to the backing layer and microneedles, it can be useful to incorporate the bioactive substance or bioactive substances in the thick backing layer patch, the microneedles shafts and the backing layer to increase bioactive substance loading. In embodiments, a microneedle-integrated thick patch of the present disclosure can encapsulate lidocaine in an amount of up to 21 weight %. In embodiments, a microneedle-integrated thick patch of the present disclosure can encapsulate lidocaine in an amount of 21 weight % or more.

Fracture Force Testing and Microneedle Penetration in Rat Skin

To determine the mechanical strength of the microneedles on the integrated patch, an electronic force gauge (Dillon Model GL, U.S.) held on a test stand (Dillon CT manual test stand) was used. The fracture force of the microneedles was first determined by placing the microneedles on a flat block of aluminium and rotating the hand wheel of the test stand slowly in an anticlockwise manner as the plunger contacts the patch. When the microneedles broke, there was a sudden decrease in the amount of force exerted and that point would be the fracture force of the microneedle.

The average force required to break a microneedle of the representative microneedle-integrated thick patch on an aluminium block was 91.28±9.21 N, while the average force of a thumb to press the microneedles onto and into the skin of a subject was 10.72±0.92 N. The average force of a thumb to press the microneedles onto and into skin was determined using a pool of five individual human subjects. The average force of a thumb to press the microneedles onto and into the skin was markedly lower that the microneedle fracture force (i.e., the force required to fracture a microneedle) indicating that the microneedles will not break if pressed onto and into the skin of a subject with the force of a thumb. In embodiments, the fracture force of a microneedle of a microneedle-integrated thick patch of the present disclosure is about 91 N or more, or about 100 N or more. In embodiments, the required force of a thumb to press the microneedles of a microneedle-integrated thick patch of the present disclosure onto and into the skin of a human patient or subject is about 12 N or less, about 11.64 N or less, about 10 N or less, about 9.8 N or less, or about 9 N or less.

In accordance with an embodiment of the present disclosure, the length of microneedles and the percentage of broken microneedles were determined for microneedle arrays of microneedle-integrated thick patch devices having different forces exerted thereon. As the force increased, the length of microneedles remained similar (FIG. 18 G). The average length of a microneedle with 10 N of force exerted thereon was 865±22 μm while the average length of a microneedle with 70 N of force exerted thereon was 848±23 μm. Hence, no significant decrease in microneedle length was observed when the different forces were applied onto the microneedle arrays (p>0.05), and the microneedle arrays appeared sharp even after a single administration on a skin model (FIGS. 18 C-F). No broken microneedles were observed for all microneedle sample arrays with 10-30 N of force exerted thereon. Two (2) broken needles were observed for a microneedle array sample having a force of 50 N exerted thereon. Four (4) broken needles were observed for a microneedle array sample having a force of 70 N exerted thereon.

The effect of varying the amount of force exerted on microneedles of a microneedle-integrated thick patch device to penetrate a skin model was also investigated. The skin model comprising defatted rat skin was placed on top of 10 layers of Kimwipes® to provide a tissue like mechanical support. Varying forces (10N, 30N, 50N, 70N) were exerted on the microneedles placed on rat skin for 1 minute and the microneedles were imaged to determine the percentage decrease in length and the number of broken microneedles (FIG. 19A-19E). The extent of needle penetration into the rat skin was also determined by the trypan blue staining method. Trypan blue was placed on the microneedle treated skin with a dropper for 5 minutes and removed gently using Kimwipes® and 70% ethanol. Skin samples were then viewed under a hand-held microscope (Eikona Image Soft, China). To compare against the force of a thumb required for the microneedle to penetrate skin, 5 individual human subjects were asked to exert a force using the thumb of their dominant hand on the plunger of the force gauge.

After applying the microneedles of microneedle-integrated thick patch devices of the present disclosure on the skin model to determine the mechanical strength of the microneedles, the trypan blue staining test was done on the skin model to determine the extent of skin penetration. The fabricated microneedles managed to penetrate through the stratum corneum with a force as low as 10N (FIGS. 19A and 19E). About 50 out of 64 (78%) microneedles could penetrate the skin at 10 N and an average of 61 out of 64 microneedles (95%) could penetrate the skin when 70 N of force was exerted to the microneedle array. Even though the amount of force exerted on the microneedles was gradually increased, the penetration of the microneedles was rather consistent with more than 75% of microneedles penetrating the skin.

Encapsulation of Lidocaine and Management of Chronic Pain and/or Neuropathic Pain The ability of a representative microneedle-integrated thick patch of the present disclosure for encapsulating a large amount of a bioactive substance (in this case the drug lidocaine) for the management of chronic pain and/or neuropathic pain was investigated. Currently available transdermal patches exhibit slow release of the drug and lower permeation rates of the drug leading to suboptimal benefits in managing chronic pain and neuropathic pain. In embodiments, the microneedle devices of the present disclosure including the microneedle-integrated thick patch device can be used alleviate pain faster in subjects suffering with chronic pain and/or neuropathic pain due to the increased permeation of a drug or drugs afforded by the use of the microneedle devices of the present disclosure.

To ensure that lidocaine could diffuse out of a microneedle-integrated thick patch of the present disclosure, an in vitro release test was conducted. First, the upper surface of a microneedle-integrated thick patch was covered with a waterproof vinyl tape (3M Vinyl Tape) to prevent diffusion of lidocaine from the upper surface of the microneedle-integrated thick patch. Then the microneedle-integrated thick patch was immersed in 15 mL of 1× phosphate buffered saline (PBS) in a falcon tube incubated at 37° C. and sampled at regular intervals. At each sampling point, all 15 mL of the release solution was withdrawn and replaced with fresh PBS. The amount of lidocaine released into PBS was determined by high performance liquid chromatography (HPLC). A positive control to determine the release of lidocaine from Lignopad® was done as well.

Referring to FIG. 20A-B, a representative microneedle-integrated thick patch of the present disclosure was used to encapsulate lidocaine in different concentrations (i.e., 2.2 weight % of lidocaine, 15 weight % of lidocaine and 21 weight % of lidocaine). Lidocaine was dissolved in prepolymer solution a particular weight %. After fabrication of the microneedle-integrated thick patch, the microneedles were weighed and the amount of lidocaine was calculated from the weight of the microneedles. As shown in FIG. 20A-B, over a period of 24 hours and 2 hours respectively the microneedle-integrated thick patch exhibited a fast initial release of the lidocaine followed by a slow and consistent release of the lidocaine.

From the in vitro release test (FIG. 20A), a total of 0.20±0.01 mg of lidocaine was released from the 2.2% w/w lidocaine patch, which constituted 15.1% of total lidocaine in the fabricated microneedle-integrated thick patch. A larger amount of lidocaine (86.24±11.61 mg) was released from the microneedle-integrated thick patch containing 21% w/w of lidocaine, which constituted nearly 100% of lidocaine encapsulated in the patch. The difference between the amount of lidocaine released from the different drug concentrations encapsulated was significant (ANOVA, $p<0.001$). Less residual drug was left in the microneedle-integrated thick patch when the concentration of lidocaine in the fabricated patch was increased, possibly due to a reduction in the polymer to drug ratio, and decreasing the possibility of drug-polymer interactions.

In embodiments, selective incorporation of lidocaine in the backing layer, microneedle shafts and/or thick backing layer patch can be achieved by using prepolymer solutions containing lidocaine to fabricate the backing layer, microneedles and/or thick backing layer patch respectively.

Enhancement of Bioactive Substance (in this Case the Drug Lidocaine) Permeation Via the Use of a Microneedle-Integrated Thick Patch The enhancement of drug permeation via the use of a microneedle-integrated thick patch of the present disclosure was evaluated. Cadaver rat skin was used to determine the permeation of lidocaine through the skin. Hair on the rat skin was removed using a hair removal cream (Veet® Sensitive Skin Hair Removal Cream). The subcutaneous fat was removed using a scalpel and hydrated in 1×PBS. The skin was divided into 6 portions: 3 replicates with Lignopad® placed on intact skin and 3 replicates using the fabricated microneedle-integrated thick patch. When applying the patches, 10 layers of Kimwipes® which mimic underlying tissues were used to support the rat skin. The microneedle-integrated thick patch was applied on the skin for 1 minute with the force of a thumb. The microneedle array was then secured onto the skin using Scotch® tape.

The rat skins with the patches were mounted on horizontal diffusion cells (TK-6H1, Shanghai Kai Kai Science and Technology Co. Ltd) with an effective exposed area of 1.131 cm$^2$. The diffusion cells were maintained at 37° C. by a circulating water jacket and the solutions were continuously stirred at 250 rpm. The receptor cells were filled with 4.5 mL of PBS with 0.005% w/v sodium azide as an anti microbial agent and samples were taken at regular intervals. 4 mL of receptor solution was withdrawn at each time interval and replaced with the same amount of fresh receptor solution. The samples were stored at 4° C. upon collection and they were centrifuged at 10 000 rpm for 5 minutes before the supernatant was withdrawn for HPLC analysis. All animal experiments were approved by IACUC, NUS.

Microneedle-integrated thick patch devices having a concentration of 2.2 weight % of lidocaine, 15 weight % of lidocaine and 21 weight % of lidocaine were were fabricated. Referring to FIG. 20C-D, the enhancement of drug permeation via the use of the microneedle-integrated thick patch was evaluated by comparing the permeation profile of lidocaine from the microneedle-integrated thick patch through rat skin with the permeation profile of lidocaine from a commercial lidocaine patch (Lignopad®).

When comparing the 21% w/w lidocaine microneedle-integrated thick patch of the present disclosure with Lignopad®, it was observed that more lidocaine permeated through the skin from the microneedle-integrated thick patch as compared to the commercially available patch (FIG. 20C). For the microneedle-integrated thick patch, a total of 25.21±3.41 mg/cm$^2$ of lidocaine permeated through skin. In contrast, a total of 19.49±8.01 mg/cm$^2$ of lidocaine from Lignopad® permeated through skin. Lidocaine was permeated within 5 minutes of placing the microneedle-integrated thick patch on the skin, as compared to Lignopad® in which lidocaine was only detected in the receptor solution after 3 hours (FIG. 20D). In embodiments, this faster initial rate of drug release can allow for a more rapid rate of pain relief as lidocaine can be delivered to pain sites faster.

According to the permeation study, the use of the microneedle-integrated thick patch of the present disclosure increased the permeation of lidocaine by 200% in the first 120 minutes, 188% in the first 180 minutes and 129% over a period of 24 hours when compared to the commercial lidocaine patch.

High Performance Liquid Chromatography Analysis of Lidocaine

The amount of lidocaine released/permeated was analyzed using an Hitachi L2000 LaChrome Elite HPLC system with a Hypersil ODS $C_{18}$ reverse column (ODS hypersil, Thermo Scientific; 4.6×250 mm, 5 μm). The mobile phase used was acetonitrile:water (70:30 v/v) with 5.5% v/v triethylamine, which was filtered through a nylon membrane filter (Whatman®, Germany) and sonicated before use. The flow rate of the pump was maintained at 0.7 mL/min and each run was 8.0 min long. 20 μL of sample was injected during each run and UV detection was performed at a wavelength of 254 nm.

Before analyzing the samples, standard lidocaine curves were plotted by preparing standard lidocaine solutions of 0.2, 1.0, 10.0 mg/mL. Injection volumes of 2, 5, 10, 15 and 20 μL were drawn from the standard solutions to obtain 3 calibration curves. The peaks obtained from the samples were then compared to the calibration curves and the amount of lidocaine present in the injected sample was extrapolated.

FTIR-ATR of PEGDA and Lidocaine

In an aim to verify if there is any interaction between the PEGDA and lidocaine, fourier transformed infrared attenuated total reflectance (FTIR-ATR) spectroscopy using PerkinElmer Spotlight 400 FTIR Imaging System was done. The spectra of the pre-polymer solution with and without lidocaine, and the spectra of the polymerized film with and without lidocaine were obtained. The films were made by exposure to high intensity UV light for 2 seconds at 11.5 cm away from the light source, followed by 4.3 seconds at 3.5 cm and 3 seconds at 11.5 cm, to mimic similar conditions used in microneedle fabrication. To analyze liquid samples, a drop of liquid was placed on top of and covering the crystal. For solid samples, the solid was placed on top of the crystal and a pressure arm was positioned over the sample to exert a force of ~80 N on the sample. No additional sample preparation was required for IR analysis.

Figure 21:
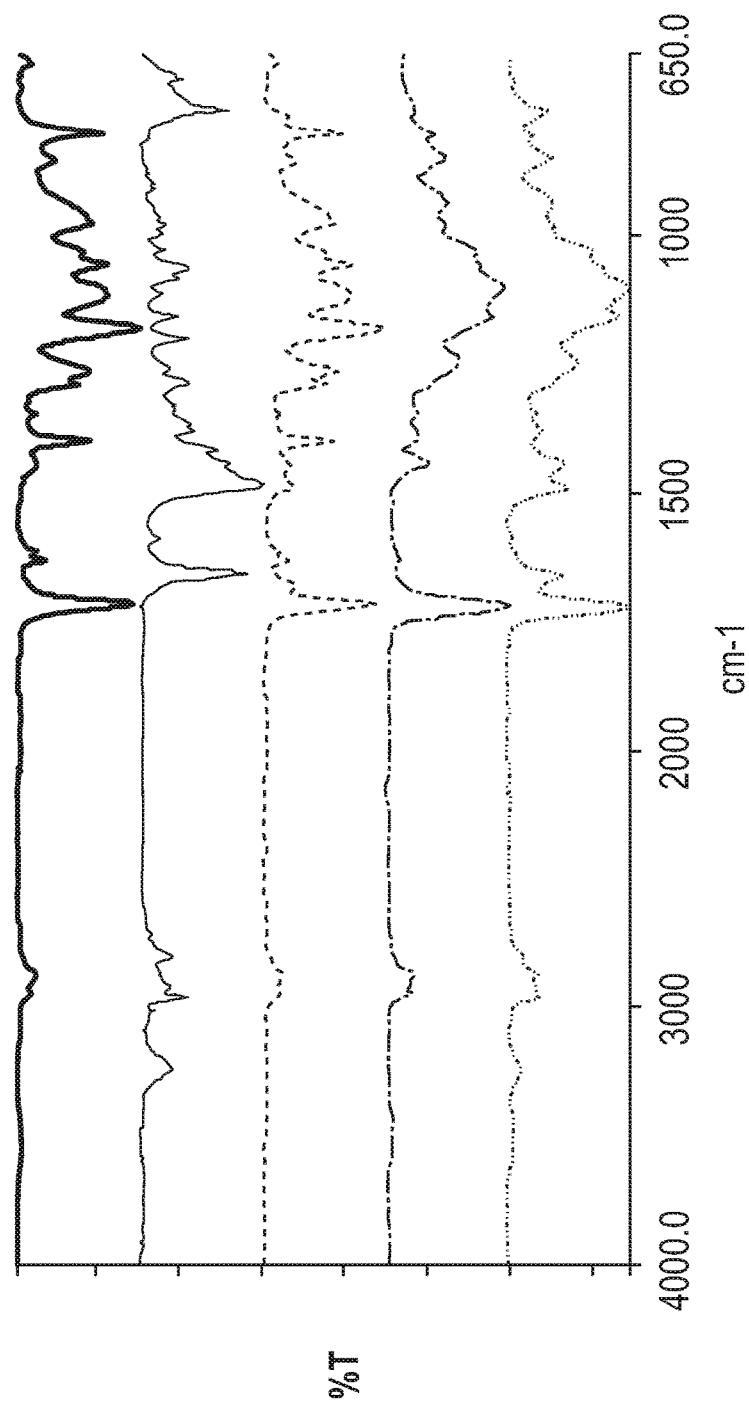
FIG. 21 is a graph showing the results of FTIR-ATR spectroscopy in accordance with an embodiment of the present disclosure of: (A) Pre-polymer solution; (B) Lidocaine powder; (C) Pre-polymer solution with 21% lidocaine dissolved in the pre-polymer solution; (D) Polymerised pre-polymer film; and (E) Polymerised pre-polymer with 21% lidocaine film.

To determine if there was any chemical interaction between PEGDA and lidocaine, the FTIR-ATR spectra were compared to see if there were any shifts or broadening of the IR stretches. From the results obtained from FTIR-ATR analysis (FIG. 21), the N—H peak from lidocaine shifted from ~3271 cm$^{-1}$ in pure lidocaine powder to ~3258 cm$^{-1}$ in lidocaine in polymerized PEGDA film and broadening of the peak was observed. Also, there was an obvious broadening of the peak at ~1660 cm$^{-1}$, which could possibly indicate the amide C=O stretch. As these observations correlate to those reported in a previous study's characterisation of lidocaine in polymers, possible hydrogen bonding might be present in the lidocaine integrated patch, which limits the release of lidocaine from the polymer and cause some lidocaine to remain in the fabricated patch even after 24 hours of application.

In addition, the spectroscopic peaks at 1635, 1621, 1409 and 810 cm$^{-1}$ corresponding to the main C=C bond signals of acryl groups in liquid PEGDA (FIG. 20A) are no longer present upon polymerization of PEGDA into the solid film (FIG. 20D).

Representative Sharp or Sharper Biocompatible Polymer Microneedle Device Fabrication and Testing Experiment The present disclosure also relates to sharp or sharper biocompatible polymer microneedles that can be used for efficient skin penetration and permeation. The present disclosure further relates to a process for fabricating sharp biocompatible polymer microneedles that can be used for efficient skin penetration and permeation. In embodiments, the sharp microneedles of the present disclosure can be used for cosmetic applications. In embodiments, the sharp microneedles of the present disclosure can be used for efficient transdermal bioactive substance (i.e., a drug(s) and/or a protein(s)) delivery.

Experiment: Representative Sharp or Sharper Biocompatible Polymeric Microneedles and a Representative Process for Fabricating Thereof In the experiment, sharp or sharper biocompatible polymeric microneedles useful for efficient skin permeation were fabricated. The process for fabricating the sharper microneedles was based on the same principles of photolithography described above wherein a photomask is used. However, the photomask used for fabricating the sharp microneedles was prepared using chromium coated glass that is optically patterned to form convex microlenses in the photomask as shown in FIG. 21(A). A prepolymer solution of PEGDA containing 0.5% of HMP was exposed to ultra violet light through the photomask thereby forming sharper microneedles as shown in FIG. 21B. The convex microlenses in the photomask cause the ultra violet light to merge due to refraction thereby causing the PEGDA polymer to form sharper microneedles as shown in FIG. 24A-C. In embodiments, the shape, length and tip diameter of microneedles can be modified by modifying the photomask to be used.

Experimental Procedures, Results and Discussion:

Materials

PEGDA (Mn=258), 2-hydroxy-2-methyl-propiophenone (HMP), bovine collagen type 1, FITC conjugate and trypan blue solution (0.4%) were purchased from Sigma-Aldrich (St. Louis, Mo.). All materials were reagent grade and were used as received.

Fabrication of a Photomask

A 4" pyrexglass wafer (Corning 7740) was first cleaned in piranha ($H_2SO_4/H_2O_2$) for 20 minutes at 120° C. as shown in FIG. 22A. Later an e-beam evaporator was used to deposit a Cr/Au layer (30 nm/1 μm) on the glass wafer. A classical photolithographic process using an AZ7220 positive photoresist was utilized to create patterns in the Cr/Au layer using a Cr/Au etchant. In order to increase the quality of the Cr/Au/photoresist masking layer, a hard baking process was performed on a hot plate at 120° C. for 30 minutes. The opposite surface of the glass wafer was temporary bonded using wax on a dummy silicon wafer in order to conserve the quality of the surface during the wet etching process. Isotropic etching of the lens or microlens was performed using an optimized HF (49%)/HCl (37%) in a 10/1 volumetric ratio using magnetic stirring for 8.5 minutes (having an etching rate of 7 μm/min). Separation of the glass wafer from the dummy silicon wafer was performed by placing on a hot plate (at 100° C.). Over-hanging photoresist and Cr/Au layers at the edges of the lenses or microlenses were removed by ultrasonication. Finally, removal of the photoresist mask and residual wax was done by cleaning in NMP (N-Methyl-2-pyrrolidone) at 80° C. in an ultrasonic tank. Microscopic analysis of the photomask dimensions was performed by directly imaging the photomask and the PDMS mold replicas copied from the microlenses with a scanning electron microscope and Nikon SMZ 1500 stereomicroscope (Nikon, Japan) respectively.

The characteristics of the photomask and the embedded microlenses affect the geometry of the microneedles significantly as the path of the UV rays are dependent on the degree of refraction on the convex surface of microlenses (FIG. 23A). Each photomask included an array of microlenses (9×9) with a constant center-to-center spacing of 1000 μm. Each photomask contained 81 microlenses to form 81 microneedles on an array. Analysis of the microlenses revealed that each microlens had a diameter of 350 μm with a flattened convex surface of diameter 130 μm, and a depth of 62.3 μm as shown in FIG. 22(B-D). To evaluate the estimated focal length of the microlens, the radius of curvature of the first surface was calculated to be 272.89 μm using the Pythagoras theorem. Considering these parameters and the refractive index of both glass (1.53627) and air (1.000) at a wavelength of 365 nm, the focal length was estimated to be 509.28 μm via the Lens maker's equation. In embodiments, the photomask of the present disclosure can have an array of microlenses of 9×9 or less (i.e., a photomask can have 81 microlenses or less). In embodiments, the photomask of the present disclosure can have an array of microlenses of 9×9 or more (i.e., a photomask can have 81 microlenses or more).

Characteristics of the thin lens in the photomask determine the degree of refraction of the UV light rays at the convex surface. The Lens makers' equation, which is used to approximate the focal length of a thin lens, was evaluated for its suitability as a predictive model for microneedle length in the inventors' fabrication process. Microneedle length measured was at least three times more than the calculated focal length regardless of UV light intensity. This indicates that the Lens makers' equation may not be an accurate predictive model. This could be due to the presence of the flattened convex surface of the microlens. The irregular convex surface could have caused spherical aberration of light rays causing the path of light rays to be significantly different from that of a conventional convex thin lens. Spherical aberration allows parallel light rays that pass through the central region of the lens to focus farther away than light rays that pass through the edges of the lens leading to differential microneedle lengths. However, it was found that the lack of a perfectly curved lens did not hinder the formation of sharp-tipped microneedles after optimization of other parameters. Thus the inventors conclude that the present geometry of the lens is suitable for their method in accordance with the present disclosure.

Fabrication of Microneedle Shafts

A photomask (1×1 cm) consisting of an array of 9×9 embedded lenses or microlenses was used for the fabrication process. A cavity, measuring 2.5×0.9 cm, was created using glass slides as shown in FIG. 22B. The number of glass sides used determines the height of the cavity (referred to as spacer thickness). Increased spacer thickness was achieved by increasing the number of glass slides stacked on either side of the glass. The photomask was positioned to ensure that the chromium coated surface faced the interior of the cavity with none of the lenses or microlenses being obscured by the sides of the cavity walls. PEGDA, containing 0.5% w/w HMP (referred to as prepolymer solution) was filled into the cavity until the chromium coated surface was in contact with the solution without any visible bubble. The setup was then irradiated with high intensity ultraviolet light of the desired intensity for 1 sec at the distance of 3.5 cm from the UV source using a UV curing station with a UV filter range of 320-500 nm (OmniCure S200-XL, EXFO Photonic Solutions Inc., Canada). The intensity of the UV light was measured with the OmniCure R2000 radiometer. A collimating adaptor (EXFO 810-00042) was used with the UV light probe. After exposure to UV light, the photomask with the array of microneedles was removed and the remaining prepolymer solution can be reused. The use of the photomask blocked the UV access in the chromium-coated regions and allowed UV light to pass through the embedded lenses or microlenses followed by subsequent refraction of light rays to a focal point that determines the height of the microneedles formed. The prepared microneedles were then imaged using Nikon SMZ 1500 stereomicroscope (Nikon, Japan) to quantify the microneedle length and tip diameter.

Effect of Intensity of UV Light

The intensity of UV light was varied between 3.14 to 15.1 W/cm$^2$ while maintaining the spacer thickness (5 mm), and keeping the distance from the UV light source (3.5 cm) constant. The average microneedle length was found to increase from 2358±144 μm to 3347±156 μm when the intensity was increased from 3.14 to 9.58 W/cm$^2$ ($p<0.05$) (FIG. 24A). However, the difference in average length measured for the microneedles formed using the intensities of 9.58 to 15.1 W/cm$^2$ was found to be insignificant ($p>0.05$). The minimum length obtained was more than three times the estimated microneedle length quantified by the focal length.

Sharpness, quantified by the tip diameter of the microneedles, reduced as the intensity was increased. The average tip diameter increased from 41.5±8.4 μm to 49.0±5.8 μm for the intensities of 3.14 to 6.44 W/cm$^2$ ($p<0.05$) as shown in FIG. 24B. However, no significant change in the tip diameter was observed for the intensities of 6.44 to 12.4 W/cm$^2$, with a maximum tip diameter of 71.6±13.7 μm obtained when an intensity of 15.1 W/cm$^2$ was used. Interestingly, a greater level of deformations on the microneedles was observed as higher intensities were used. It is noted that the microneedles' upper half became wider and more cylindrical with the lower half acquiring a more tapered formation as intensities increased. In addition, the tips of the microneedles also underwent deformations leading to more irregular structures. The microneedles fabricated at 6.44 W/cm$^2$ were observed to be more regular in shape, than that of higher intensities, without significant structural deformation thus preserving the sharpness. Hence, this intensity was chosen for fabrication of microneedles for subsequent experiments.

Effect of Spacer Distance

The spacer thickness was varied between 1050 μm to 5000 μm maintaining the intensity (6.44 W/cm$^2$) and keeping the distance the from UV light source (3.5 cm) constant. An expected increase in average length was observed for the spacer distance of 1050 to 2525 μm ($p<0.05$). An insignificant difference in average length was observed for the microneedles formed for the spacer distance of 2525 µm to 3000 µm (p>0.05).

However, the greatest microneedle length of 3347±156 µm was observed for the microneedles formed using a spacer distance of 5000 µm (p<0.05) (FIG. 24C). This trend differed from the trend observed for the tip diameter of the microneedles. The average tip diameter increased as the spacer distance was increased from 1050 µm to 3000 µm (p<0.05) with a constant tip diameter reached beyond the spacer distance of 3000 (p>0.05) (FIG. 24D).

The intensity of UV light used for the polymerization process can be important with respect to the microneedle geometric properties. One of the aims of the experiment was to fabricate sharp microneedles for efficient skin penetration with an optimum intensity that allows the inventors to achieve a balance between a long length and short tip diameter. In the new approach, an intensity of 6.44 W/cm$^2$ allowed microneedles to reach a high vertical length, with minimal structural deformation, and a desirable tip diameter that does not reduce the sharpness significantly. Although sharper microstructures without any observable deformation were obtained at lower intensities as well, the microneedles may not possess sufficient strength as a higher intensity leads to formation of more rigid microneedles which improves the penetration efficacy.

Another phenomenon observed was that the length of microneedles increased significantly with the microneedles acquiring a more cylindrical shape, compared to the hypothesized conical shape, as intensity increased. The optical nature of light may rationalize this occurrence. Due to the flat top surface of the microlens, some light rays travel beyond the focal point in a collimated manner. In addition, converged light rays may also extrapolate beyond the focal point. These particular optical movements of light rays could have led to the formation of the more cylindrical portions of the needle. However, the degree of polymerization has a limit. Based on the inverse-square law of light, UV light loses energy as the distance away from the surface of the lens increases, which might explain the tapered appearance of the microneedles observed beyond the focal point. As intensity was increased, more photons were transmitted to a further distance leading to greater uneven polymerization, evidenced by the non-uniform tapered structures and deformations formed at higher intensities.

Fabrication of Microneedle Backing Layer

Referring to FIG. 22(C), the photomask having the sharp microneedles attached thereto was placed or immersed in a well of a 24 well plate filled with prepolymer solution. In embodiments, the photomask having the sharper microneedles attached thereto can be placed or partially submerged in a well of a 12 well plate or 6 well plate filled with a prepolymer solution.

The photomask with microneedles attached thereto was placed in a well of a 24-well plate (Thermo Fisher Scientific, USA) as shown in FIG. 22C. A specified volume (300, 400 and 550 µL) of prepolymer solution was added to the well until the needles were submerged to a desired height. The volume of prepolymer solution used determines the thickness of the backing layer. The set up was then irradiated with high intensity ultraviolet light (6.44 w/cm$^2$) for a duration of 3 seconds and a distance of 10.5 cm from the UV source [EXFO OmniCure® S200-XL UV curing station (UV filter 320-500 nm) (EXFO, Photonic Solutions Inc., Canada)]. After polymerization, the microneedles with the backing layer was separated from the photomask. Microneedles of three ranges of length with minimal differences in tip diameter can be achieved via this method. The prepared microneedles with the backing layer were then imaged using Nikon AZ100 stereomicroscope (Nikon, Japan), to quantify the microneedle length, tip diameter and base diameter.

In embodiments, the ultra violet light intensity can be from about 3.14 W/cm$^2$ to about 15.1 W/cm$^2$. As shown in FIG. 22(C), during the irradiation step, a PEGDA backing layer was formed and the PEGDA macromers of the backing layer were covalently bonded to the microneedles. The prepolymer solution surrounds the submerged portion of the microneedles to form a backing layer.

Formation of a backing layer is crucial to enhance the strength of the microneedles and to enable the removal of the microneedles from the photomasks. The inventors manipulated the thickness of the backing layer by varying the volume of prepolymer solution used from 300 µL to 550 µL. Due to the affinity between the polymerized microneedles and the prepolymer solution together with the small center-to-center spacing between microneedles, capillary action was evident. This consequently led to formation of each patch of microneedle acquiring a range of length, with the tip diameter being unaffected as shown in FIG. 25(A-C). However, the range of length for each volume was significantly different from each other (p<0.05). It was observed that the average microneedle length decreased from 1224±112 µm to 583.7±105 µm as volume used to form the backing layer was increased from 300 µL to 550 µL (FIG. 25G). Similarly, base diameter reduced from 233±20 µm to 156±21 µm (p<0.05) as depicted in FIG. 25H. Previous studies have recommended equivalent diameter, rather than base diameter, for the evaluation of mechanical failure of tapered microstructures. Equivalent diameter of 111±6.6, 101±4.3 and 85±7.0 µm was calculated for the microneedles of average length 1224, 813 and 584 µm respectively, using the Equation stated below:

$$D_{equivalent} = D_{tip} + [(D_{base} - D_{tip}) \div 3]$$

The microneedles attached to the backing layer were carefully removed from the photomask and washed with deionized water to remove the uncross-linked prepolymer solution.

In embodiments, during the fabrication of the microneedles and the fabrication of the backing layer, optimization of ultra violet intensity can be performed by varying the ultra violet intensity from about 3.14 W/cm$^2$ to about 15.1 W/cm$^2$. In embodiments, during the fabrication of the microneedles and the fabrication of the backing layer, optimization of spacer length can be performed by varying the spacer from about 1050 µm to about 5000 µm.

Effect of Ultra Violet Intensity

As shown in FIG. 24(A), in embodiments, modifying the ultra violet intensity can be used to modify the microneedles to have an average length of from about 2357±143 µm to about 4035±293 µm. As shown in FIG. 24(B), in embodiments, modifying the ultra violet intensity can be used to tune the dip diameter of the microneedles to be from about 41±8 µm to about 71±13 µm. In embodiments, an ultra violet intensity of about 3.14 W/cm$^2$ can be used to provide microneedles having an average length of about 2357±143 µm. In embodiments, an ultra violet intensity of about 15.1 W/cm$^2$ can be used to provide microneedles having an average length of about 4035±293 µm. In embodiments, an ultra violet intensity of about 3.14 W/cm$^2$ can be used to provide microneedles having a tip diameter of about 41±8 µm. In embodiments, an ultra violet intensity of about 15.1 W/cm$^2$ can be used to provide microneedles having a tip diameter of about 71±13 µm.

Effect of Spacer Thickness

As shown in FIG. 24(C), in embodiments, modifying the spacer thickness can be used to modify the microneedles to have a length of from about 1117±73 µm to about 3346±155 µm. As shown in FIG. 24(D), in embodiments, modifying the spacer thickness can be used to tune the tip diameter of the microneedles to be from about 279±8 µm to about 48±5 µm.

Effect of Varying Prepolymer Solution Volume

As mentioned above, in embodiments, during the fabrication of the backing layer, the photomask having the sharper microneedles attached thereto can be placed or immersed in a well of a 16 well plate or a well of a 24 well plate filled with prepolymer solution and exposed to ultra violet light. Referring to FIGS. 25A-C and FIG. 24G, modifying the amount of prepolymer solution can be used to modify the average length of the microneedles. In embodiments, the prepolymer volume can be about 300 µL, about 400 µL or about 500 µL. In embodiments, the use of a prepolymer volume of 300 µL can result in a microneedle length of about 1224 µm as shown in FIG. 25(A). In embodiments, the use of a prepolymer volume of 400 µL can result in a microneedle length of about 813 µm as shown in FIG. 25(B). In embodiments, the use of a prepolymer volume of 500 µL can result in a microneedle length of about 583 µm as shown in FIG. 25(C). As shown in FIG. 25G, in embodiments, increasing the prepolymer solution volume can result in a decrease in microneedle length. For example, increasing the prepolymer solution from about 300 µL to about 500 µL can result in a decrease in microneedle length from about 1224 µm to about 583 µm.

Microneedle Fracture Force Testing

Microneedles of three ranges of lengths were pressed against an aluminium plate with a force applied by a digital force gauge (Dillon GL, USA). The applied force was increased until maximum resistance was observed. The force at which microneedles start to break (fracture force) was recorded after which microneedles were imaged using Nikon AZ100 stereomicroscope (Nikon, Japan), to assess the changes in the microneedle geometric characteristics.

Evaluation of the effect of the thickness of the patch on the strength of microneedles can be essential for the selection of the appropriate type of patch for maximum penetration through the skin. After subjecting each class of patch to an increasing force, it was observed that the fracture force was consistent for all three classes of patches (p<0.05) with a similar degree of breakage for each class as depicted in FIG. 25(D-F) and FIG. 25(I).

In addition, it was noticed that the microneedles in the patches formed by 300 µL and 400 µL of prepolymer solution, portrayed a certain degree of elasticity allowing the resultant microneedles after force testing to appear bent. Bent structures were not observed in the shaft with the thickest backing layer. However, tip diameter and length of the microneedles were not affected in any of the three types of microneedle shafts.

The formation of the backing layer is important to strengthen the array as a whole and to ensure reusability of the photomask. Emphasizing the importance of the backing layer, the effect of the thickness of the backing layer on the strength of the microneedle shafts and extent of penetration was studied. The initial hypothesis that increasing the backing layer thickness would also increase the amount of force required to break the needle was proven incorrect as evidenced by the indifferent fracture force of the microneedles for all three types of microneedle shafts when pressed against an aluminium block. In fact, in all three types of microneedle shafts, a significant fraction of the microneedles was intact after a force of more than 60 N was applied. However the ability to withstand high forces of compression by the different shafts may be due to different mechanisms. In the 300 µL and 400 µL patches, a significant level of elasticity was observed in the microneedles evidenced by the bent orientation of the microneedles post force testing. This feature of the longer needles could explain the ability of the lower volume shafts to withstand high level of force without much breakage as the bending posture of the microneedles allows force to be absorbed. In the 550 µL patch, the microneedles were too short to portray a significant level of flexibility similar to the other two structures but excessive force could be minimized due to the thick backing layer acting as a shock absorber.

Microneedle Penetration in Rat Skin

Microneedles of three different average lengths were inserted into excised rat abdominal skin obtained from Comparative Medicine Centre, National university of Singapore (NUS). The hair was first removed using hair removal cream Veet (Reckitt Benckiser, Poland). The skin samples were cleaned and the subcutaneous fat was removed using a scalpel. The skin was fully stretched on ten layers of Kimwipe (Kimberly-Clark, Roswell, Ga.) to mimic tissue-like mechanical support. Each microneedle shaft was inserted using the force of a thumb for 1 minute. The microneedles were then removed and the area of insertion was stained with trypan blue for 1 minute. Trypan blue, being hydrophobic in nature, specifically stains the hydrophobic perforated stratum corneum sites. Intact skin stained with trypan blue was used as a negative control. The excess stain was wiped away using Kimwipe (Kimberly-Clark, Roswell, Ga.) and ethanol (70%). The areas stained with the dye were viewed by brightfield microscopy using Eikona Image Soft Microscope (China). All animal experiments were approved by Institutional Animal Care and Use Committee (IACUC), National University of Singapore (NUS).

Microneedles of average length 1224, 813 and 584 µm were inserted in excised rat skin. Trypan blue staining method was used to demonstrate the extent of penetration by each type of microneedle shaft as shown in FIG. 26(A-C). Negligible staining on the control skin (FIG. 26D) proves that trypan blue only stains the sites of corneum perforation significantly.

The extent of penetration by the microneedle shafts of needle length 1224 and 813 µm was found to be indifferent (p>0.05) with a percentage of penetration of 73.0±2.3% and 71.6±2.5% respectively. However, a significant improvement in penetration percentage was observed for the microneedle shaft with the shortest needle length at 94.4±3.3% as shown in FIG. 26F. Elastic deformations similar to FIG. 25(E-F) were noticed in the shafts with the two longest needle lengths. Fracture of microneedle was not observed in any of the shafts tested.

Elasticity of the polymeric microneedles may also explain the varying percentage of penetration observed among the microneedle shafts. Penetration failure may be due to reduced axial load explained by buckling (bending) failure by elastic instability of the longer microneedles. Buckling has been reported as a common occurrence in polymeric microneedles by various studies. The ability for the microneedles to bend causes the actual compressive stress at the tip of the microneedle to be much lesser than the total compressive force applied by the thumb. It has been reported in literature that to avoid sudden failure of a microneedle by buckling, and to insert the microneedle into the skin successfully, a 12:1 aspect ratio of length-to-equivalent diameter or lesser is recommended. This recommendation may not be suitable for the microneedles fabricated using the inventors' method. The inventors observed that all three types of shafts fabricated obtained an aspect ratio below that of 12:1. The shaft with the longest microneedle length (1224 µm) obtained the highest aspect ratio of 11:1, while the other two shafts obtained an aspect ratio of 8:1 and 7:1 respectively. However, only the shortest shaft was able to penetrate efficiently without buckling. This shows that an aspect ratio of 7:1 or below can be an appropriate geometric prerequisite for the microneedle shafts fabricated from the inventors' photolithographical method.

Collagen Permeation Through Rat Skin

Microneedles of the longest range of length were inserted into excised rat abdominal skin. Hair and fat were removed as mentioned previously. The skin was fully stretched on a thin layer of PDMS to mimic tissue-like mechanical support. A force of 10 N was applied using the digital force gauge (Dillon GL, USA) for 2 minutes. Bovine skin collagen type 1, FITC conjugate (MW=300 kDa) of concentrations 0.025, 0.050 and 0.075% w/v was obtained by diluting the stock collagen solution (0.1% w/v) withappropriate amount of 0.1 M Tris-HCl buffer (pH 7.8) containing 0.4 M NaCl, 10 mM $CaCl_2$ and 0.25 M glucose. NaCl and $CaCl_2$ aid in stabilizing the collagen molecules and glucose is added to prevent gelation of the collagen fibers. Each collagen concentration was applied to separate skin samples at the area of insertion. The time of contact between the collagen solution and the skin was kept constant at 4 hours at room temperature, after which excess collagen on the skin surface was removed using Kimwipe (Kimberly-Clark, Roswell, Ga.). The degree of permeation of collagen through the skin was quantified by using the A-1R confocal microscope (Nikon, Japan) to observe the fluorescence intensity of collagen type 1, FITC conjugate at excitation and emission wavelengths of 490 nm and 520 nm respectively. Other parameters including high voltage (150), offset (−1), laser (7.2% of 150 mW), pinhole (1.2 A.U), optical sectioning (16.6 µm), scan size (512×512), scan speed (1 frame/sec), pixel dwell (2.2 µsec), lever average (4), zoom (5×), step size (5 µm) and intensity calculation (low=300, high=4095) were kept constant.

The ability of microneedles to increase skin permeation of bovine collagen type 1, FITC conjugate (MW=300 kDa) was assessed. The control (without collagen treatment) was found to possess a significant level of auto fluorescence which was visible up to a depth of 150 µm (FIG. 27A). This phenomenon could be due to the presence of fluorescent biomolecules such as lipofuscin and riboflavin on the rat skin which are able to emit light at similar wavelengths used in the experiment. However, this did not hinder the analysis of the degree of penetration by the needles and permeation of collagen. All three samples revealed a penetration to a depth of 250 to 300 µm confirming the increased extent of diffusion of collagen molecules through the skin up to the dermis layer as shown in FIG. 27(B-D).

Permeation study of macromolecules was performed using bovine skin collagen type 1, FITC conjugate as model drug. Fluorescence from collagen enabled easy analysis and visualization of depth of permeation. Diffusion of collagen molecules was greatly enhanced by the treatment of skin with the fabricated microneedles. Collagen molecules were able to diffuse past the epidermis and reach the dermal layer. This enables exogenous collagen to express its pharmacological function effectively which includes activating keratinocytes in the dermis layer for reepithelialization. The fact that higher concentrations of collagen did not significantly affect the diffusion rate, can be explained by the fact that epidermis and dermis layer offer a significant permeability barrier to both small molecules and macromolecules thus becoming the rate limiting step upon sufficient permeabilization of the stratum corneum. This implies that higher doses of collagen may not warrant an increased pharmacological effect when delivered transdermally.

Aspects of particular embodiments of the present disclosure address at least one aspect, problem, limitation, and/or disadvantage associated with exiting systems, apparatuses, devices, processes, and/or techniques for fabricating microneedle devices. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, apparatuses, components, processes, or alternatives thereof, may be desirably combined into other different systems, apparatuses, components, processes, and/or applications. In addition, various modifications, alterations, and/or improvements can be made to various embodiments by a person of ordinary skill in the art.

We claim:

1. A method for microneedle device fabrication comprising:
    providing a backing structure;
    contacting at least one microneedle forming biocompatible polymer with a surface of the backing structure to form a microneedle forming biocompatible polymer layer on the surface of the backing structure, the microneedle forming biocompatible polymer layer having a thickness, the microneedle forming biocompatible polymer layer covalently coupleable to the backing structure; and
    performing an exposure process comprising selectively directing electromagnetic energy into portions of each of the backing structure and the biocompatible polymer layer to form a set of microneedles within the biocompatible polymer layer covalently coupled to the surface of the backing structure,
    wherein the set of microneedles comprises crosslinked biocompatible polymer material suitable for penetration into skin in the absence of additional fabrication processes directed to forming the set of microneedles other than removal of non-crosslinked biocompatible polymer material from the set of microneedles.

2. The method of claim 1, wherein at least one of the backing structure and the microneedle forming biocompatible polymer layer carries at least one biosubstance prior to performing the exposure process, and wherein the exposure process is performed in a manner that maintains at least approximately 80% of the structural and functional integrity of the at least one biosubstance.

3. The method of claim 2, further comprising maintaining during each step of microneedle device fabrication the at least one biosubstance at a temperature at which at least approximately 80% of the structural and functional integrity of the at least one biosubstance is maintained.

4. The method of claim 2, further comprising avoiding exposing the at least one biosubstance to reactive plasma species and carbon-based chemical solvents.

5. The method of claim 2, further comprising avoiding exposing the at least one biosubstance to a solvent other than water.

6. The method of claim 2, wherein performing the exposure process comprises a set of exposure events, each exposure event comprising directing electromagnetic energy into portions of the backing structure and the microneedle forming biopolymer layer for a period of time that maintains at least approximately 80% of the structural and functional integrity of the at least one biosubstance.

7. The method of claim 1, wherein performing the exposure process comprises:
disposing a patterned film photomask at least proximate to the backing structure, the photomask defining regions through which ultraviolet light can propagate, the regions corresponding to a set of microneedle cross-sectional areas; and directing electromagnetic energy through each of the regions, portions of the backing structure, and portions of the microneedle forming biocompatible polymer layer.

8. The method of claim 1, wherein the microneedle forming biocompatible polymer comprises a poly(ethylene) glycol (PEG) based polymer.

9. The method of claim 8, wherein the backing layer comprises a poly(ethylene) glycol (PEG) based polymer.

10. The method of claim 1, wherein contacting a microneedle forming biocompatible polymer with a surface of the backing structure comprises:
providing a chamber having a set of interior surfaces, at least one interior surface of the set of interior surfaces comprising the surface of the backing structure intended for contacting the microneedle forming biocompatible polymer; and introducing the microneedle forming biocompatible polymer into the chamber.

11. The method of claim 10, wherein contacting a microneedle forming biocompatible polymer with a surface of the backing structure further comprises establishing a chamber depth corresponding to an intended length of microneedles within the set of microneedles.

12. The method of claim 10, wherein performing the exposure process comprises selectively directing electromagnetic energy into the chamber.

13. The method of claim 1, wherein providing a backing structure comprises:
providing a support member;
providing a chamber having a set of interior surfaces, at least one interior surface within the set of interior surfaces comprising a surface of the support member;
introducing at least one biocompatible polymer into the chamber;
contacting the at least one biocompatible polymer with the surface of the support member corresponding to an interior surface of the set of interior surfaces, thereby forming a biocompatible polymer layer carried by the surface of the support member; and
directing electromagnetic energy into the chamber for crosslinking portions of biocompatible polymer layer to thereby form a biocompatible backing layer carried by the surface of the support member.

14. A method for fabrication of a microneedle device, comprising:
providing a first backing structure having a front surface and a back surface;
contacting at least one microneedle forming biocompatible polymer with the front surface of the first backing structure to form a microneedle forming biocompatible polymer layer on the front surface of the first backing structure, the microneedle forming biocompatible polymer layer having a thickness, the microneedle forming biocompatible polymer layer covalently coupleable to the front surface of the first backing structure;
performing an exposure process comprising selectively directing electromagnetic energy into portions of each of the first backing structure and the biocompatible polymer layer to form a set of microneedles within the biocompatible polymer layer covalently coupled to the front surface of the first backing structure;
providing a second backing structure; and
combining the first backing structure having microneedles covalently coupled to the front surface of the first backing structure with the second backing structure, wherein the second backing structure is chemically coupled to the back surface of the first backing structure;
wherein the set of microneedles comprises crosslinked biocompatible polymer material suitable for penetration into skin in the absence of additional fabrication processes directed to forming the set of microneedles other than removal of non-crosslinked biocompatible polymer material from the set of microneedles.

15. A method for fabricating microneedles comprising:
providing a glass photomask with microlenses etched in the glass photomask;
contacting at least one microneedle forming biocompatible polymer with a surface of the glass photomask to form a microneedle forming biocompatible polymer layer on the surface of the glass photomask, the microneedle forming biocompatible polymer layer having a thickness, the microneedle forming biocompatible polymer layer covalently coupleable to a backing structure;
performing an exposure process comprising selectively directing electromagnetic energy into portions of each of the glass photomask and the biocompatible polymer layer to form a set of microneedles within the biocompatible polymer layer;
removing non-crosslinked biocompatible polymer material from the set of microneedles;
then, partially submerging the set of microneedles in a volume of prepolymer; and
directing electromagnetic energy into at least the set of microneedles and the volume of prepolymer to form a set of microneedles covalently coupled to the backing structure.

16. The method of claim 14, wherein performing the exposure process includes: disposing a patterned film photomask at least proximate to the backing structure, the photomask defining regions through which ultraviolet light can propagate, the regions corresponding to a set of microneedle cross-sectional areas; and directing electromagnetic energy through each of the regions, portions of the backing structure, and portions of the microneedle forming biocompatible polymer layer.

17. The method of claim 13, further comprising removing the backing layer and the set of microneedles carried thereby from the support member.

* * * * *